US009493479B2

(12) United States Patent
Graham et al.

(10) Patent No.: US 9,493,479 B2
(45) Date of Patent: Nov. 15, 2016

(54) SUBSTITUTED PYRIDO[1,2-A]PYRAZINES AS HIV INTEGRASE INHIBITORS

(71) Applicant: Merck Sharp & Dohme Corp., Rahway, NJ (US)

(72) Inventors: Thomas H. Graham, Scotch Plains, NJ (US); John S. Wai, Harleysville, PA (US); Andrew Stamford, Chatham, NJ (US); Wensheng Liu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/785,148

(22) PCT Filed: Apr. 11, 2014

(86) PCT No.: PCT/US2014/033720
§ 371 (c)(1),
(2) Date: Oct. 16, 2015

(87) PCT Pub. No.: WO2014/172188
PCT Pub. Date: Oct. 23, 2014

(65) Prior Publication Data

US 2016/0060272 A1 Mar. 3, 2016

Related U.S. Application Data

(60) Provisional application No. 61/812,489, filed on Apr. 16, 2013.

(51) Int. Cl.

| | |
|---|---|
| ***A61K 31/4985*** | (2006.01) |
| ***C07D 241/38*** | (2006.01) |
| ***C07D 491/147*** | (2006.01) |
| ***A61K 31/55*** | (2006.01) |
| ***C07D 471/04*** | (2006.01) |
| ***C07D 471/14*** | (2006.01) |
| ***C07D 491/14*** | (2006.01) |
| ***A61K 45/06*** | (2006.01) |
| ***C07D 491/20*** | (2006.01) |

(52) U.S. Cl.
CPC ....... *C07D 491/147* (2013.01); *A61K 31/4985* (2013.01); *A61K 31/55* (2013.01); *A61K 45/06* (2013.01); *C07D 471/04* (2013.01); *C07D 471/14* (2013.01); *C07D 491/14* (2013.01); *C07D 491/20* (2013.01)

(58) Field of Classification Search
CPC ......................... A61K 31/4985; C07D 241/38
USPC ......... 514/249, 250; 544/342, 343, 346, 349
See application file for complete search history.

(56) References Cited

U.S. PATENT DOCUMENTS 7,037,908 B2 5/2006 Naidu et al.
7,115,601 B2 10/2006 Naidu et al.
7,135,467 B2 11/2006 Walker et al.
7,157,447 B2 1/2007 Naidu et al.
7,169,780 B2 1/2007 Crescenzi et al.
7,173,022 B2 2/2007 Naidu et al.
7,176,196 B2 2/2007 Naidu et al.
7,192,948 B2 3/2007 Banville et al.
7,211,572 B2 5/2007 Miyazaki et al.
7,217,713 B2 5/2007 Crescenzi et al.
7,232,819 B2 6/2007 Di Francesco et al.
7,273,859 B2 9/2007 Naidu
7,279,487 B2 10/2007 Egbertson et al.
7,414,045 B2 8/2008 Crescenzi et al.
7,419,969 B2 9/2008 Naidu et al.
7,517,532 B2 4/2009 Wai et al.
8,410,103 B2 4/2013 Johns et al.
2004/0229909 A1 11/2004 Kiyama et al.
2005/0054645 A1 3/2005 Miyazaki et al.
2006/0276466 A1 12/2006 Naidu et al.
(Continued)

FOREIGN PATENT DOCUMENTS

WO WO2005087766 A1 9/2005
WO WO2006066414 A1 6/2006
(Continued)

OTHER PUBLICATIONS

Jordan, V. C. Nature Reviews: Drug Discovery, 2, 2003, 205.*
Dorwald, F. Zaragoza. Side Reactions in Organic Synthesis: A Guide to Successful Synthesis Design, Weinheim: WILEY-VCH Verlag GmbH & Co. KGaA, 2005, Preface.*
Hackam, et al. JAMA, 296(14), 2006, 1731-1732.*
Ester Muraglia et al, Design and Synthesis of Bicyclic Pyrimidinones as Potent and Orally Bioavailable HIV-1 Integrase Inhibits, J. Med. Chem., 2008, pp. 861-874, vol. 51, US.
Marco Ferrara et al, Synthesis of a Hexahydropyrimido[1,2-a]Azepine-2-Carboxamide Derivative Useful as an HIV Integrase Inhibitor, Tetrahedron Letters, Jul. 2007, pp. 8379-8382, vol. 48, No. 37, US.
(Continued)

*Primary Examiner* — Douglas M Willis
(74) *Attorney, Agent, or Firm* — Alysia A. Finnegan; Gloria M. Fuentes

(57) ABSTRACT

The present invention relates to 4-Pyridone Compounds of Formula (I); and pharmaceutically acceptable salts and prodrugs thereof, wherein A, $R^1$, $R^2$, and $R^3$ are as defined herein. The present invention also relates to compositions comprising at least one 4-Pyridone Compound, and methods of using the 4-Pyridone Compounds for treating or preventing HIV infection in a subject or the clinical manifestations thereof.

(I)

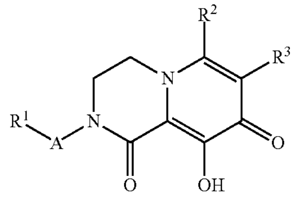

12 Claims, No Drawings

(56) References Cited

U.S. PATENT DOCUMENTS

| | | | |
|---|---|---|---|
| 2007/0049606 | A1 | 3/2007 | Banville et al. |
| 2007/0083045 | A1 | 4/2007 | Di Francesco et al. |
| 2007/0111984 | A1 | 5/2007 | Naidu et al. |
| 2007/0111985 | A1 | 5/2007 | Naidu et al. |
| 2007/0112190 | A1 | 5/2007 | Naidu |
| 2007/0123524 | A1 | 5/2007 | Crescenzi et al. |
| 2007/0142635 | A1 | 6/2007 | Askin et al. |
| 2007/0149556 | A1 | 6/2007 | Mikamiyama et al. |
| 2007/0281917 | A1 | 12/2007 | Naidu et al. |
| 2008/0004265 | A1 | 1/2008 | Walker et al. |
| 2009/0099168 | A1 | 4/2009 | Donghi et al. |

FOREIGN PATENT DOCUMENTS

| | | | |
|---|---|---|---|
| WO | WO2006103399 | A1 | 10/2006 |
| WO | WO2006116764 | A1 | 11/2006 |
| WO | WO2006121831 | A2 | 11/2006 |
| WO | WO2008048538 | A1 | 4/2008 |
| WO | WO2010042391 | A2 | 4/2010 |
| WO | WO2010042392 | A2 | 4/2010 |
| WO | WO2011045330 | A1 | 4/2011 |
| WO | WO2011121105 | A1 | 10/2011 |
| WO | WO 2014/172188 | * | 10/2014 |

OTHER PUBLICATIONS

Olaf D. Kinzel et al, The Syntheis of Tetrahydropyridopyrimidones as a New Scaffold for HIV-1 Integrase Inhibitors, Tetrahedron Letters, 2007, pp. 6552-6555, vol. 48, No. 37, US.

Ying-Jie Wang et al., Assessment of the susceptibility of mutant HIV-1 to antiviral agents, Journal of Virological Methods, 2010, pp. 230-237, 165(2).

* cited by examiner

SUBSTITUTED PYRIDO[1,2-A]PYRAZINES AS HIV INTEGRASE INHIBITORS

CROSS-REFERENCE TO RELATED APPLICATIONS

This application is a §371 National Stage Application of PCT/US2014/033720, international filing date of Apr. 11, 2014, which claims the benefit of U.S. Provisional Application No. 61/812,489, filed Apr. 16, 2013, the contents of which are hereby incorporated by reference in their entirety.

FIELD OF THE INVENTION

The present invention relates to 4-Pyridone Compounds, compositions comprising at least one 4-Pyridone Compound, and methods of using the 4-Pyridone Compounds for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

The HIV genome is made up of single-stranded RNA which comprises several genes that code for structural proteins common to all retroviruses and additional genes that code for accessory proteins specific to HIV (A. D. Frankel and J. A. T. Young, *Annu. Rev. Biochem.* 67:1-25 (1998)). Open reading frames encoding structural proteins include the pol gene (Ratner et al., *Nature* 313: 277-284 (1985)), which encodes reverse transcriptase, integrase and HIV protease, the gag gene, which encodes the core proteins of the virion (Toh et al., *EMBO J.* 4: 1267-1272 (1985); Power et al., *Science* 231: 1567-72 (1986); Pearl et al., *Nature* 329: 351-54 (1987)), and the env gene, which encodes gp120 (surface) and gp41 (TM/transmembrane). All three enzymes encoded by the pol gene have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir and integrase inhibitors such as raltegravir.

Examples of references that are related to HIV integrase inhibitors include the following:

Kinzel et al., *Tet. Letters* 2007, 48(37): 6552-6555; Ferrara et al., *Tet. Letters* 2007, 48(37): 8379-8382; and Muraglia et al., *J. Med. Chem.* 2008, 51: 861-874;

International Patent Appln. Publication Nos. WO 11/045330, WO2006/121831, WO 2006/103399, WO 11/121105, WO2005/87766, WO 2010/042391, WO 2010/042392, WO 06/116764, and WO 2008/48538;

US Patent Appln. Publication Nos. 2004/229909, 2007/0083045, 2007/0142635, 2007/0111984, 2005/0054645, 2006/0276466, 2007/0049606, 2007/0111985, 2007/0112190, 2007/0281917, 2008/0004265, 2007/0149556, and 2007/0123524; and U.S. Pat. No. 7,232,819, U.S. Pat. No. 7,169,780, U.S. Pat. No. 7,217,713, U.S. Pat. No. 7,279,487, U.S. Pat. No. 7,135,467, U.S. Pat. No. 7,037,908, U.S. Pat. No. 7,211,572, U.S. Pat. No. 7,414,045, U.S. Pat. No. 7,115,601, U.S. Pat. No. 7,157,447, U.S. Pat. No. 7,173,022, U.S. Pat. No. 7,176,196, U.S. Pat. No. 7,192,948, U.S. Pat. No. 7,273,859, and U.S. Pat. No. 7,419,969.

SUMMARY OF THE INVENTION

In one aspect, the present invention provides Compounds of Formula (I):

(I)

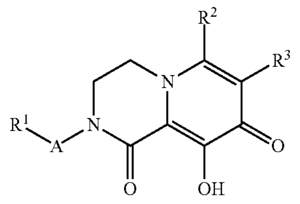

or a pharmaceutically acceptable salt or prodrug thereof, wherein:

A is a bond or $C_{1-3}$ alkylene;

$R^1$ is selected from $C_6$-$C_{10}$ aryl, 5 or 6-membered monocyclic heteroaryl and 9- to 11-membered bicyclic heteroaryl, wherein said $C_6$-$C_{10}$ aryl group, said 5 or 6-membered monocyclic heteroaryl group or said 9- to 11-membered bicyclic heteroaryl group can be optionally substituted with one or more groups, each independently selected from halo, $C_1$-$C_6$ alkyl, $C_1$-$C_6$ haloalkyl, —CN, —$N(R^4)_2$, —OH, —O—($C_1$-$C_6$ alkyl), —O—($C_1$-$C_6$ haloalkyl), —$OC(O)R^7$, —$C(O)N(R^4)_2$; —$NHC(O)R^7$ and —$C(O)OR^7$;

$R^2$ is —$C(R^7)(R^8)N(R^4)_2$ or $C_1$-$C_6$ hydroxyalkyl;

$R^3$ is selected from $C_1$-$C_6$ alkenyl, $C_1$-$C_6$ alkyl, $C_3$-$C_6$ cycloalkenyl and $C_3$-$C_7$ cycloalkyl, or $R^2$ and $R^3$, together with the carbon atoms to which they are attached, can optionally join to form a cyclic group Y;

each occurrence of $R^4$ is selected from H, $C_1$-$C_6$ alkyl, $C_3$-$C_7$ cycloalkyl, —($C_{1-3}$ alkylene)-O—($C_1$-$C_6$ alkyl), or —C(O)—$R^{10}$;

$R^7$ is H, $C_1$-$C_6$ alkyl, $C_3$-$C_7$ cycloalkyl or phenyl;

$R^8$ is H, $C_1$-$C_6$ alkyl, $C_3$-$C_7$ cycloalkyl or phenyl, or $R^7$ and $R^8$ and the common carbon atom to which they are attached, combine to form a carbonyl group;

$R^{10}$ is $C_1$-$C_6$ alkyl, $C_6$-$C_{10}$ aryl, $C_3$-$C_7$ cycloalkyl, 5 or 6-membered monocyclic heteroaryl, 9- to 11-membered bicyclic heteroaryl, 4- to 8-membered monocyclic heterocycloalkyl, or 8- to 11-membered bicyclic heterocycloalkyl;

Y is selected from 4- to 8-membered monocyclic heterocycloalkyl, 8- to 11-membered bicyclic heterocycloalkyl, 4- to 8-membered monocyclic heterocycloalkenyl and 8- to 11-membered bicyclic heterocycloalkenyl, wherein said 4- to 8-membered monocyclic heterocycloalkyl group can optionally form a spirocycle at one of its ring carbon atoms with a separate 3- to 6-membered monocyclic heterocycloalkyl group, a separate 5- or 6-membered monocyclic heterocycloalkenyl group, or a separate 6- to 10-membered bicyclic heterocycloalkyl group, and wherein any Y group can be optionally substituted on one or more ring carbon atoms with one or more groups, each independently selected from $C_1$-$C_6$ alkyl, $C_1$-$C_6$ alkenyl and —OH, —O—($C_1$-$C_6$ alkyl), —C(O)$OR^6$, —C(O)$N(R^5)_2$, $C_6$-$C_{10}$ aryl, 5- or 6-membered monocyclic heterocycloaryl, 9 to 11-membered bicyclic heterocycloaryl, and wherein Y can also be optionally substituted on one or more ring nitrogen atoms with a group, independently selected from $C_1$-$C_6$ alkyl, —C(O)—$OR^6$, —C(O)$N(R^4)_2$ and —C(O)—($C_1$-$C_3$ alkylene)-$N(R^4)_2$, wherein Y does not have the structure:

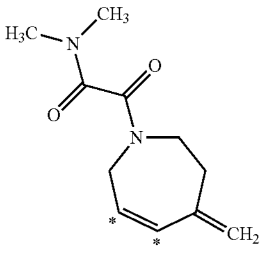

or

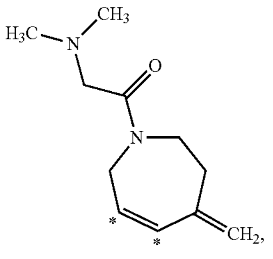

wherein the * symbols designate the point of attachment of $R^2$ and $R^3$ to the rest of the compound;

$R^6$ is selected from H, $C_1$-$C_6$ alkyl, $C_3$-$C_7$ cycloalkyl, $C_6$-$C_{10}$ aryl, 5- or 6-membered monocyclic heterocycloaryl and 9 to 11-membered bicyclic heterocycloaryl;

and each occurrence of $R^5$ is selected from H, $C_1$-$C_6$ alkyl, $C_3$-$C_7$ cycloalkyl and —($C_{1-3}$ alkylene)-O—($C_1$-$C_6$ alkyl).

The Compounds of Formula (I) (also referred to herein as the "4-Pyridone Compounds") and pharmaceutically acceptable salts and prodrugs thereof can be useful, for example, for inhibiting HIV viral replication or replicon activity, or for treating or preventing HIV infection in a subject. Without being bound by any specific theory, it is believed that the 4-Pyridone Compounds inhibit HIV viral replication by inhibiting HIV Integrase.

Accordingly, the present invention includes methods for treating or preventing HIV infection in a subject, comprising administering to the subject an effective amount of at least one 4-Pyridone Compound.

The details of the invention are set forth in the accompanying detailed description below. Illustrative methods and materials for practicing the invention described herein. Other embodiments, aspects and features of the present invention are either further described in or will be apparent from the ensuing description, examples and appended claims.

DETAILED DESCRIPTION OF THE INVENTION

The present invention relates to 4-Pyridone Compounds, compositions comprising at least one 4-Pyridone Compound, and methods of using the 4-Pyridone Compounds.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of a 4-Pyridone Compound and/or an additional therapeutic agent, or a composition thereof that is effective in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N$(alkyl)_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contains from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. With respect to the cyclic group Y, as defined in the Summary of the Invention herein, reference to a substitution with a $C_1$ alkenyl group refers to a ═$CH_2$, wherein the carbon of the $CH_2$ is bonded to a ring carbon within the cyclic group Y. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contains from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms. The term "$C_3$-$C_5$ alkylene" refers to an alkylene group having from 3 to 5 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═$CHCH_2$—, —$CH_2$CH═CH—, —$CH_2$CH═$CHCH_2$—, —CH═$CHCH_2CH_2$—, —$CH_2CH_2$CH═CH— and —$CH(CH_3)$CH═CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "$C_2$-$C_6$ alkylene" refers to an alkenylene group having from 2 to 6 carbon atoms. The term "$C_3$-$C_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein. An arylene group is divalent and either available bond on an arylene group can connect to either group flanking the arylene group. For example, the group "A-arylene-B," wherein the arylene group is:

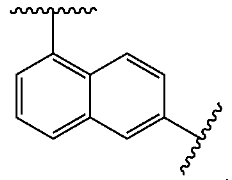

, is understood to represent both:

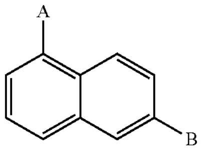

and

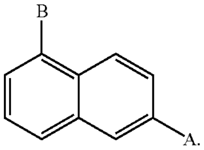

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

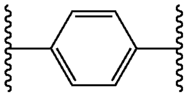

,

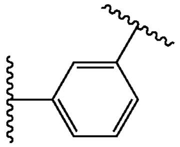

or

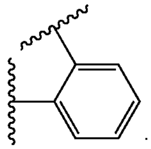

.

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from 5 to 10 ring carbon atoms. In another embodiment, a cycloalkyl contains from 3 to 7 ring atoms. In another embodiment, a cycloalkyl contains from 5 to 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

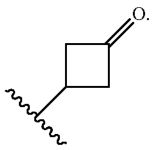 [SMILES: *C1CC(=O)C1]

The term "cycloalkenyl," as used herein, refers to a non-aromatic mono- or multicyclic ring system comprising from about 3 to about 10 ring carbon atoms and containing at least one endocyclic double bond. In one embodiment, a cycloalkenyl group is contains from about 3 to about 6 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein. A ring carbon atom of a cycloalkyl group may be functionalized as a carbonyl group. In one embodiment, a cycloalkenyl group is unsubstituted. In another embodiment, a cycloalkenyl group is cyclopentenyl. In another embodiment, a cycloalkenyl group is cyclohexenyl. The term "$C_3$-$C_6$ cycloalkenyl" refers to a cycloalkenyl group having from 3 to 6 ring carbon atoms. Unless otherwise indicated, a cycloalkenyl group is unsubstituted.

The term "halo," as used herein, means —F, —Cl, —Br or —I. In one embodiment, a halo group is —F or —Cl. In another embodiment, a halo group is —F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include $—CH_2F$, $—CHF_2$, $—CF_3$, $—CH_2Cl$ and $—CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include $—CH_2OH$, $—CH_2CH_2OH$, $—CH_2CH_2CH_2OH$ and $—CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and has from 9 to 11 ring atoms. A heteroaryl group can be optionally substituted by one or more "ring system substituents" which may be the same or different, and are as defined herein. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to 7 ring atoms. In another embodiment, a heterocycloalkyl group is monocyclic has from about 4 to about 8 ring atoms. In one embodiment, the 4- to 8-membered monocyclic heterocycloalkyl group can form a spirocycle at one of its ring carbon atoms with a separate 3- to 6-membered monocyclic heterocycloalkyl group, a separate 5- or 6-membered monocyclic heterocycloalkenyl group, or a separate 6- to 10-membered bicyclic heterocycloalkyl group. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like. The term "heterocycloalkyl" also encompasses a heterocycloalkyl group, as defined herein, which is fused to an aryl (e.g., benzene) or heteroaryl ring. A heterocycloalkyl group can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like.

A ring carbon atom of a heterocycloalkyl group may be functionalized as a carbonyl group. An illustrative example of such a heterocycloalkyl group is:

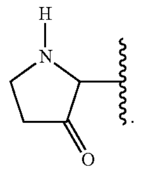 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "ring system substituent," as used herein, refers to a substituent group attached to an aromatic or non-aromatic ring system which, for example, replaces an available hydrogen on the ring system. Examples of ring system substituents, which are independently selected, include: alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, $—NO_2$, —CN, $—SF_5$, —C(O)OH, —C(O)O-alkyl, —C(O)O-aryl, —C(O)O-alkylene-aryl, —S(O)-alkyl, $—S(O)_2$-alkyl, —S(O)-aryl, $—S(O)_2$-aryl, —S(O)-heteroaryl, $—S(O)_2$-heteroaryl, —S-alkyl, —S-aryl, —S-heteroaryl, —S-alkylene-aryl, —S-alkylene-heteroaryl, $—S(O)_2$-alkylene-aryl, $—S(O)_2$-alkylene-heteroaryl, $—Si(alkyl)_2$, $—Si(aryl)_2$, $—Si(heteroaryl)_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, $—C(=N—CN)—NH_2$, $—C(=NH)—NH_2$, —C(=NH)—NH(alkyl), $—N(Y_1)(Y_2)$, -alkylene-$N(Y_1)(Y_2)$, $—C(O)N(Y_1)(Y_2)$ and $—S(O)_2N(Y_1)(Y_2)$, wherein $Y_1$ and $Y_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, $—C(CH_3)_2—$ and the like which form moieties such as, for example:

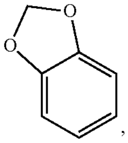
,
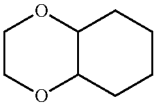
and
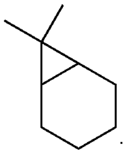
.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^1$, $R^7$, etc.) occurs more than one time in any constituent or in any formula provided herein, e.g. Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a 4-Pyridone Compound or a pharmaceutically acceptable salt of the compound. The transformation may occur by various mechanisms (e.g., by metabolic or chemical processes), such as, for example, through hydrolysis in blood. For example, if a 4-Pyridone Compound or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a 4-Pyridone Compound contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a 4-Pyridone Compound incorporates an amine functional group, a prodrug can be formed by the replacement of a hydrogen atom in the amine group with a group such as, for example, R-carbonyl-, RO-carbonyl-, NRR'-carbonyl-wherein R and R' are each independently ($C_1$-$C_{10}$)alkyl, ($C_3$-$C_7$) cycloalkyl, benzyl, a natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$) alkyl; carboxy ($C_1$-$C_6$)alkyl; amino($C_1$-$C_4$)alkyl or mono-N— or di-N,N—($C_1$-$C_6$)alkylaminoalkyl; —C($Y^4$)$Y^5$ wherein $Y^4$ is H or methyl and $Y^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.,* 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.,* 5(1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The 4-Pyridone Compounds can form salts which are also within the scope of this invention. The term "salt(s)", as employed herein, denotes acidic salts formed with inorganic and/or organic acids, as well as basic salts formed with inorganic and/or organic bases. In addition, when a 4-Pyridone Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a 4-Pyridone Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the 4-Pyridone Compounds may be atropisomers (e.g., substituted biaryls) and are considered as part of this invention. Enantiomers can also be directly separated using chiral chromatographic techniques.

It is also possible that the 4-Pyridone Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a 4-Pyridone Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the 4-Pyridone Compounds, and of the salts, solvates, hydrates, esters and prodrugs of the 4-Pyridone Compounds, are intended to be included in the present invention.

The following abbreviations are used below and have the following meanings: AcOH is acetic acid; atm is atmosphere; Bn is benzyl; BOP-Cl is Bis(2-oxo-3-oxazolidinyl) phosphonic chloride; CSA is camphorsulfonic acid; DBU is 1,8-diazabicyclo[5.4.0]undec-7-ene; DIEA, DIPEA and Hunig's base are N,N-diisopropylethylamine; DMA is dimethylacetamide; DMF is dimethylformamide; DMSO is dimethylsulfoxide; DPPF is 1,1'-bis(diphenylphosphino)ferrocene; EDCI is 1-ethyl-3-(3'-dimethylaminopropyl)carbodiimide hydrochloride; ESI is electrospray ionization; EtOAc is isethyl acetate; EtOH is ethanol; HATU is 2-(1H-7-Azabenzotriazol-1-yl)-1,1,3,3-tetramethyl uronium hexafluorophosphate; HOBT is 1-hydroxy benzotriazole; HPLC is high-performance liquid chromatography; LCMS is liquid chromatography-mass spectrometry; MeCN is acetonitrile; MeOH is methanol; MS is mass spectroscopy; NHS is normal human serum; NMR is nuclear magnetic resonance spectroscopy; Pd/C is palladium on carbon; $Pd(dppf)Cl_2$ or $PdCl_2(dppf)$ is 1,1'-bis(diphenylphosphino) ferrocene palladium dichloride; $Pd(Ph_3P)_4$ is tetrakistriphenylphosphine palladium; PLC-301 is 1,3-Bis(2,4,6-trimethylphenyl)-4,5-dihydroimidazol-2-ylidene[2-(i-propoxy)-5-(N,N-dimethylaminosulfonyl)phenyl]methylene ruthenium(II) dichloride; RP-HPLC is reverse phased high-pressure liquid chromatography; TFA is trifluoroacetic acid; TLC is thin-layer chromatography; THF is tetrahydrofuran.

The Compounds of Formula (I):

The present invention provides 4-Pyridone Compounds of Formula (I):

(I)

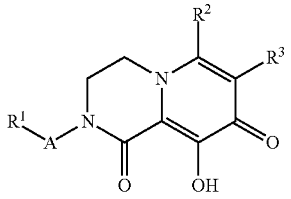

and pharmaceutically acceptable salts and prodrugs thereof, wherein A, $R^1$, $R^2$, and $R^3$ are defined above for the Compounds of Formula (I).

A first embodiment of the invention (Embodiment E1) is a compound of Formula I, or a pharmaceutically acceptable salt or prodrug thereof, wherein A is a bond, or $C_{1-3}$ alkylene, preferably $—CH_2—$, wherein all other variables are as originally defined (i.e. as defined in Formula I in the Summary of the Invention).

A second embodiment (Embodiment E2) is a compound of Formula I, or a pharmaceutically acceptable salt or prodrug thereof, wherein $R^1$ is $C_6$-$C_{10}$ aryl; wherein said aryl group can be optionally substituted with one or more groups, each independently selected from halo, $C_1$-$C_6$ alkyl, $C_1$-$C_6$ haloalkyl, —CN, $—N(R^4)_2$, —OH, —O—($C_1$-$C_6$ alkyl), —O—($C_1$-$C_6$ haloalkyl), $—OC(O)R^7$, $—C(O)N(R^4)_2$; $—NHC(O)R^7$ and $—C(O)OR^2$; and all other variables are as defined in Embodiment E1.

A third embodiment (Embodiment E3) is a compound of Formula I, or a pharmaceutically acceptable salt or prodrug thereof, wherein $R^1$ is a 5 or 6-membered monocyclic heteroaryl; wherein said 5 or 6-membered monocyclic heteroaryl group can be optionally substituted with one or more groups, each independently selected from halo, $C_1$-$C_6$ alkyl, $C_1$-$C_6$ haloalkyl, —CN, —$N(R^4)_2$, —OH, —O—($C_1$-$C_6$ alkyl), —O—($C_1$-$C_6$ haloalkyl), —$OC(O)R^2$, —$C(O)N(R^4)_2$; —$NHC(O)R^7$ and —C(O)OR7; and all other variables are as defined in Embodiment E1.

A fourth embodiment (Embodiment E4) is a compound of Formula I, or a pharmaceutically acceptable salt or prodrug thereof, wherein $R^1$ is a 9- to 11-membered bicyclic heteroaryl; wherein said 9- to 11-membered bicyclic heteroaryl group can be optionally substituted with one or more groups, each independently selected from halo, $C_1$-$C_6$ alkyl, $C_1$-$C_6$ haloalkyl, —CN, —$N(R^4)_2$, —OH, —O—($C_1$-$C_6$ alkyl), —O—($C_1$-$C_6$ haloalkyl), —$OC(O)R^7$, —$C(O)N(R^4)_2$; —$NHC(O)R^7$ and —C(O)OR7; and all other variables are as defined in Embodiment E1.

A fifth embodiment of the invention (Embodiment E5) is a compound of Formula I, or a pharmaceutically acceptable salt or prodrug thereof, wherein $R^1$ is as defined in any of Embodiments E1-E4; $R^2$ is —$C(R^7)(R^8)N(R^4)_2$; $R^7$ is H, $C_1$-$C_6$ alkyl, $C_3$-$C_7$ cycloalkyl, or phenyl; and all other variables are as defined in Embodiment E1.

A sixth embodiment of the invention (Embodiment E6) is a compound of Formula I, or a pharmaceutically acceptable salt or prodrug thereof, wherein $R^1$ is as defined in any of Embodiments E1-E4, $R^2$ is —$C(R^7)(R^8)N(R^4)_2$; $R^8$ is H, $C_1$-$C_6$ alkyl, $C_3$-$C_7$ cycloalkyl, or phenyl; and all other variables are as defined in Embodiment E1.

A seventh embodiment of the invention (Embodiment E7) is a compound of Formula I, or a pharmaceutically acceptable salt or prodrug thereof, wherein $R^1$ is as defined in any of Embodiments E1-E4, $R^2$ is —$C(R^7)(R^8)N(R^4)_2$; and $R^7$ and $R^8$ and the common carbon atom to which they are attached, combine to form a carbonyl group; and all other variables are as defined in Embodiment E1.

An eighth embodiment of the invention (Embodiment E8) is a compound of Formula I, or a pharmaceutically acceptable salt or prodrug thereof, wherein $R^1$ is as defined in any of Embodiments E1-E4, $R^2$ is —$C(R^7)(R^8)N(R^4)_2$; at least one occurrence of $R^4$ is —C(O)—$R^{10}$; $R^{10}$ is $C_1$-$C_6$ alkyl, $C_6$-$C_{10}$ aryl, $C_3$-$C_7$ cycloalkyl, 5 or 6-membered monocyclic heteroaryl, 9- to 11-membered bicyclic heteroaryl, 4- to 8-membered monocyclic heterocycloalkyl, or 8- to 11-membered bicyclic heterocycloalkyl; and all other variables are as defined in Embodiment E1.

A ninth embodiment of the invention (Embodiment E9) is a compound of Formula I, or a pharmaceutically acceptable salt or prodrug thereof, wherein $R^1$ is as defined in any of Embodiments E1-E4; $R^2$ is —$C(R^7)(R^8)N(R^4)_2$; at least one occurrence of $R^4$ is H, $C_1$-$C_6$ alkyl, $C_3$-$C_7$ cycloalkyl, or —($C_{1-3}$ alkylene)-O—($C_1$-$C_6$ alkyl), and all other variables are as defined in Embodiment E1.

A tenth embodiment of the invention (Embodiment E10) is a compound of Formula I, or a pharmaceutically acceptable salt or prodrug thereof, wherein $R^1$ is as defined in any of Embodiments E1-E4; $R^2$ is $C(O)N(R^4)_2$; at least one occurrence of $R^4$ is H, $C_1$-$C_6$ alkyl, $C_3$-$C_7$ cycloalkyl, or —($C_{1-3}$ alkylene)-O—($C_1$-$C_6$ alkyl), and all other variables are as defined in Embodiment E1.

An eleventh embodiment of the invention (Embodiment E11) is a compound of Formula I, or a pharmaceutically acceptable salt or prodrug thereof, wherein $R^1$ is as defined in any of Embodiments E1-E4; $R^2$ is $C(O)N(R^4)_2$; at least one occurrence of $R^4$ is —C(O)—$R^{10}$; $R^{10}$ is $C_1$-$C_6$ alkyl, $C_6$-$C_{10}$ aryl, $C_3$-$C_7$ cycloalkyl, 5 or 6-membered monocyclic heteroaryl, 9- to 11-membered bicyclic heteroaryl, 4- to 8-membered monocyclic heterocycloalkyl, or 8- to 11-membered bicyclic heterocycloalkyl, and all other variables are as defined in Embodiment E1.

A twelfth embodiment of the invention (Embodiment E12) is a compound of Formula I, or a pharmaceutically acceptable salt or prodrug thereof, wherein $R^1$ is as defined in any of Embodiments E1-E4; $R^2$ is $C_1$-$C_6$ hydroxyalkyl; and all other variables are as defined in Embodiment E1.

A thirteenth embodiment of the invention (Embodiment E13) is a compound of Formula I, or a pharmaceutically acceptable salt or prodrug thereof, wherein $R^1$ is as defined in any of Embodiments E1-E4; $R^2$ is —$C(O)N(CH_3)_2$, $C(O)NHCH_2CH_2OCH_3$, —$CH_2NH_2$ or —$CH_2OH$; and all other variables are as defined in Embodiment E1.

A fourteenth embodiment of the invention (Embodiment E14) is a compound of Formula I, or a pharmaceutically acceptable salt or prodrug thereof, wherein $R^1$ is as defined in any of Embodiments E1-E4; $R^2$ is as defined in any of Embodiments E5-E13; $R^3$ is $C_1$-$C_6$ alkenyl; and all other variables are as defined in Embodiment E1.

A fifteenth embodiment of the invention (Embodiment E15) is a compound of Formula I, or a pharmaceutically acceptable salt or prodrug thereof, wherein $R^1$ is as defined in any of Embodiments E1-E4; $R^2$ is as defined in any of Embodiments E5-E13; $R^3$ is $C_1$-$C_6$ alkyl, and all other variables are as defined in Embodiment E1.

A sixteenth embodiment of the invention (Embodiment E16) is a compound of Formula I, or a pharmaceutically acceptable salt or prodrug thereof, wherein $R^1$ is as defined in any of Embodiments E1-E4; $R^2$ is as defined in any of Embodiments E5-E13; $R^3$ is $C_3$-$C_6$ cycloalkenyl; and all other variables are as defined in Embodiment E1.

A seventeenth embodiment of the invention (Embodiment E17) is a compound of Formula I, or a pharmaceutically acceptable salt or prodrug thereof, wherein $R^1$ is as defined in any of Embodiments E1-E4; $R^2$ is as defined in any of Embodiments E5-E13; $R^3$ is $C_3$-$C_7$ cycloalkyl; and all other variables are as defined in Embodiment E1.

An eighteenth embodiment of the invention (Embodiment E18) is a compound of Formula I, or a pharmaceutically acceptable salt or prodrug thereof, wherein $R^1$ is as defined in any of Embodiments E1-E4; $R^2$ is as defined in any of Embodiments E5-E13; $R^3$ is isopropyl; and all other variables are as defined in Embodiment E1.

A nineteenth embodiment of the invention (Embodiment E19) is a compound of Formula I, or a pharmaceutically acceptable salt or prodrug thereof, wherein $R^1$ is as defined in any of Embodiments E1-E4; $R^2$ is as defined in any of Embodiments E5-E13; $R^3$ is —$C(CH_3)$═$CH_2$; and all other variables are as defined in Embodiment E1.

A twentieth embodiment of the invention (Embodiment E20) is a compound of Formula I, or a pharmaceutically acceptable salt or prodrug thereof, wherein $R^1$ is as defined in any of Embodiments E1-E4; $R^2$ is as defined in any of Embodiments E5-E13; $R^3$ is $CF_3$; and all other variables are as defined in Embodiment E1.

A twenty-first embodiment of the invention (Embodiment E21) is a compound of Formula I, or a pharmaceutically acceptable salt or prodrug thereof, wherein $R^1$ is as defined in any of Embodiments E1-E4; $R^2$ is as defined in any of Embodiments E5-E13; $R^3$ is —$CH_2CF_3$; and all other variables are as defined in Embodiment E1.

A twenty-second embodiment of the invention (Embodiment E22), is a compound of Formula I, or a pharmaceutically acceptable salt or prodrug thereof, wherein $R^1$ is as defined in any of Embodiments E1-E4; $R^2$ and $R^3$, together with the carbon atoms to which they are attached, join to form a cyclic group Y; wherein Y is a 4- to 8-membered monocyclic heterocycloalkyl, wherein said 4- to 8-membered monocyclic heterocycloalkyl group can optionally form a spirocycle at one of its ring carbon atoms with a separate 3- to 6-membered monocyclic heterocycloalkyl group, a separate 5- or 6-membered monocyclic heterocycloalkenyl group, or a separate 6- to 10-membered bicyclic heterocycloalkyl group; wherein Y can be optionally substituted on one or more ring carbon atoms with one or more groups, each independently selected from $C_1$-$C_6$ alkyl, $C_1$-$C_6$ alkenyl and —OH, —O—($C_1$-$C_6$ alkyl), —C(O)OR$^6$, —C(O)N(R$^5$)$_2$, $C_6$-$C_{10}$ aryl, 5- or 6-membered monocyclic heterocycloaryl, 9 to 11-membered bicyclic heterocycloaryl, and wherein Y can also be optionally substituted on one or more ring nitrogen atoms with a group, independently selected from $C_1$-$C_6$ alkyl, —C(O)—OR$^6$—C(O)N(R$^4$)$_2$ and —C(O)—($C_1$-$C_3$ alkylene)-N(R$^4$)2, wherein Y does not have the structure:

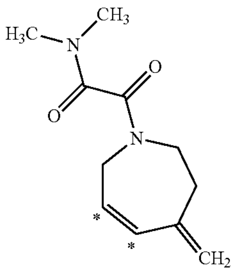

or

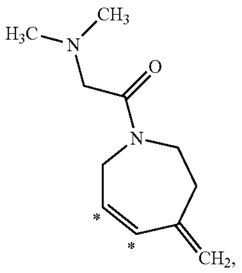

, wherein the * symbols designate the point of attachment of $R^2$ and $R^3$ to the rest of the compound; and all other variables are as defined in Embodiment E1.

A twenty-third embodiment of the invention (Embodiment E23) is a compound of Formula I, or a pharmaceutically acceptable salt or prodrug thereof, wherein $R^1$ is as defined in any of Embodiments E1-E4; $R^2$ and $R^3$, together with the carbon atoms to which they are attached, join to form a cyclic group Y; wherein Y is an 8- to 11-membered bicyclic heterocycloalkyl; wherein Y can be optionally substituted on one or more ring carbon atoms with one or more groups, each independently selected from $C_1$-$C_6$ alkyl, $C_1$-$C_6$ alkenyl and —OH, —O—($C_1$-$C_6$ alkyl), —C(O)OR$^6$, —C(O)N(R$^5$)$_2$, $C_6$-$C_{10}$ aryl, 5- or 6-membered monocyclic heterocycloaryl, 9 to 11-membered bicyclic heterocycloaryl, and wherein Y can also be optionally substituted on one or more ring nitrogen atoms with a group, independently selected from $C_1$-$C_6$ alkyl, —C(O)—OR$^6$—C(O)N(R$^4$)$_2$ and —C(O)—($C_1$-$C_3$ alkylene)-N(R$^4$)$_2$ and all other variables are as defined in Embodiment E1.

A twenty-fourth embodiment of the invention (Embodiment E24) is a compound of Formula I, or a pharmaceutically acceptable salt or prodrug thereof, wherein $R^1$ is as defined in any of Embodiments E1-E4; $R^2$ and $R^3$, together with the carbon atoms to which they are attached, join to form a cyclic group Y; wherein Y is a 4- to 8-membered monocyclic heterocycloalkenyl; wherein Y can be optionally substituted on one or more ring carbon atoms with one or more groups, each independently selected from $C_1$-$C_6$ alkyl, $C_1$-$C_6$ alkenyl and —OH, —O—($C_1$-$C_6$ alkyl), —C(O)OR$^6$, —C(O)N(R$^5$)$_2$, $C_6$-$C_{10}$ aryl, 5- or 6-membered monocyclic heterocycloaryl, 9 to 11-membered bicyclic heterocycloaryl, and wherein Y can also be optionally substituted on one or more ring nitrogen atoms with a group, independently selected from $C_1$-$C_6$ alkyl, —C(O)—OR$^6$—C(O)N(R$^4$)$_2$ and —C(O)—($C_1$-$C_3$ alkylene)-N(R$^4$)2; and all other variables are as defined in Embodiment E1.

A twenty-fifth embodiment of the invention (Embodiment E25) is a compound of Formula I, or a pharmaceutically acceptable salt or prodrug thereof, wherein $R^1$ is as defined in any of Embodiments E1-E4; $R^2$ and $R^3$, together with the carbon atoms to which they are attached, join to form a cyclic group Y; wherein Y is a 8- to 11-membered bicyclic heterocycloalkenyl; wherein Y can be optionally substituted on one or more ring carbon atoms with one or more groups, each independently selected from $C_1$-$C_6$ alkyl, $C_1$-$C_6$ alkenyl and —OH, —O—($C_1$-$C_6$ alkyl), —C(O)OR$^6$, —C(O)N(R$^5$)$_2$, $C_6$-$C_{10}$ aryl, 5- or 6-membered monocyclic heterocycloaryl, 9 to 11-membered bicyclic heterocycloaryl, and wherein Y can also be optionally substituted on one or more ring nitrogen atoms with a group, independently selected from $C_1$-$C_6$ alkyl, —C(O)—OR$^6$—C(O)N(R$^4$)$_2$ and —C(O)—($C_1$-$C_3$ alkylene)-N(R$^4$)$_2$ and all other variables are as defined in Embodiment E1.

A twenty-sixth embodiment of the invention (Embodiment E26), is a compound of Formula I, or a pharmaceutically acceptable salt or prodrug thereof, wherein $R^1$ is as defined in any of Embodiments E1-E4; $R^2$ and $R^3$, together with the carbon atoms to which they are attached, join to form a cyclopentenyl group Y, wherein Y can be optionally substituted on one or more ring carbon atoms with one or more groups, each independently selected from $C_1$-$C_6$ alkyl, $C_1$-$C_6$ alkenyl and —OH, —O—($C_1$-$C_6$ alkyl), —C(O)OR$^6$, —C(O)N(R$^5$)$_2$, $C_6$-$C_{10}$ aryl, 5- or 6-membered monocyclic heterocycloaryl, 9 to 11-membered bicyclic heterocycloaryl, and wherein Y can also be optionally substituted on one or more ring nitrogen atoms with a group, independently selected from $C_1$-$C_6$ alkyl, —C(O)—OR$^6$—C(O)N(R$^4$)$_2$ and —C(O)—($C_1$-$C_3$ alkylene)-N(R$^4$)$_2$ and all other variables are as defined in Embodiment E1.

A twenty-seventh embodiment of the invention (Embodiment E27) is a compound of Formula I, or a pharmaceutically acceptable salt or prodrug thereof, wherein $R^1$ is as defined in any of Embodiments E1-E4; $R^2$ and $R^3$, together with the carbon atoms to which they are attached, join to form a cyclohexenyl group Y, wherein Y can be optionally substituted on one or more ring carbon atoms with one or more groups, each independently selected from $C_1$-$C_6$ alkyl, $C_1$-$C_6$ alkenyl and —OH, —O—($C_1$-$C_6$ alkyl), —C(O)OR$^6$, —C(O)N(R$^5$)$_2$, $C_6$-$C_{10}$ aryl, 5- or 6-membered monocyclic heterocycloaryl, 9 to 11-membered bicyclic heterocycloaryl, and wherein Y can also be optionally substituted on one or more ring nitrogen atoms with a group, independently selected from $C_1$-$C_6$ alkyl, —C(O)—OR$^6$—C(O)N(R$^4$)$_2$ and —C(O)—($C_1$-$C_3$ alkylene)-N(R$^4$)$_2$, and all other variables are as defined in Embodiment E1.

A twenty-eighth embodiment of the invention (Embodiment E28) is a compound of Formula I, or a pharmaceutically acceptable salt or prodrug thereof, wherein $R^1$ is as defined in any of Embodiments E1-E4; $R^2$ and $R^3$, together with the carbon atoms to which they are attached, join to form a cyclopentyl group Y, wherein Y can be optionally substituted on one or more ring carbon atoms with one or more groups, each independently selected from $C_1$-$C_6$ alkyl, $C_1$-$C_6$ alkenyl, —OH, —O—($C_1$-$C_6$ alkyl), —C(O)OR$^6$, —C(O)N(R$^5$)$_2$, $C_6$-$C_{10}$ aryl, 5- or 6-membered monocyclic heterocycloaryl, 9 to 11-membered bicyclic heterocycloaryl, and wherein Y can also be optionally substituted on one or more ring nitrogen atoms with a group, independently selected from $C_1$-$C_6$ alkyl, —C(O)—$OR^6$—C(O)N($R^4$)$_2$ and —C(O)—($C_1$-$C_3$ alkylene)-N($R^4$)$_2$, and all other variables are as defined in Embodiment E1.

A twenty-ninth embodiment of the invention (Embodiment E29), is a compound of Formula I, or a pharmaceutically acceptable salt or prodrug thereof, wherein $R^1$ is as defined in any of Embodiments E1-E4; $R^2$ and $R^3$, together with the carbon atoms to which they are attached, join to form a cyclic group Y having the structure:

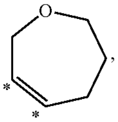,
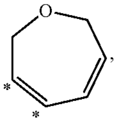,
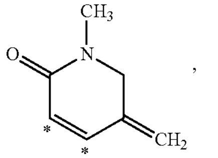,
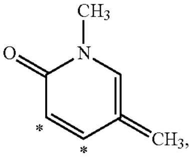
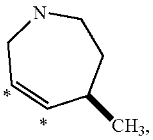
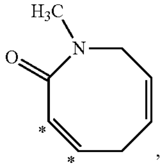,
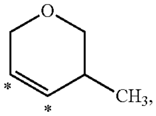
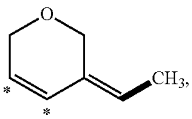
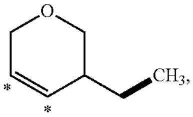
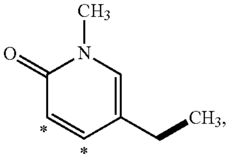
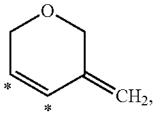
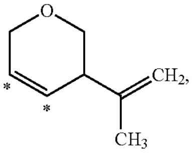
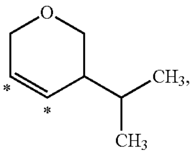
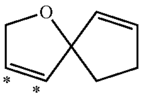,
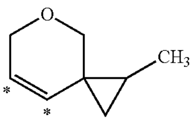
,
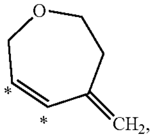
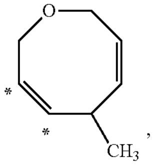,
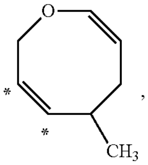
,
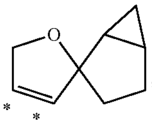,
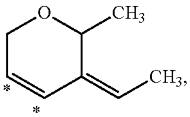, -continued

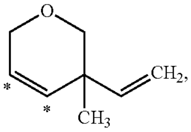
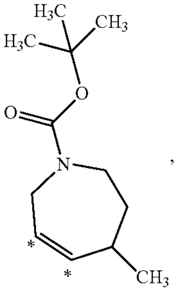,
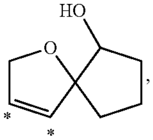,
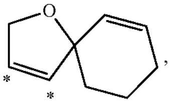,
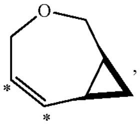,
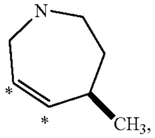
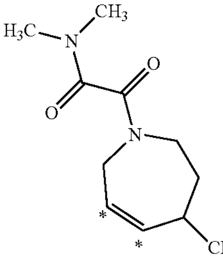,
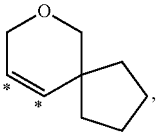,
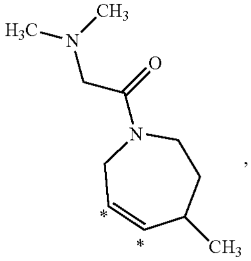,
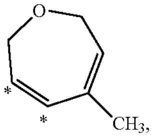 or
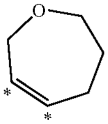

wherein the * symbols designate the point of attachment of $R^2$ and $R^3$ to the rest of the compound; and all other variables are as defined in Embodiment E1.

The invention also provides further embodiments of Embodiment E1 through Embodiment E29, which is a compound of Formula I, or a pharmaceutically acceptable salt thereof.

One class of compounds of the invention (alternatively referred to as Class C-1) includes compounds of Formula (Ia):

(Ia)

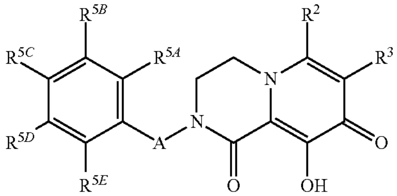

or pharmaceutically acceptable salts thereof, wherein:

A is $C_{1-3}$ alkylene;

$R^{5A}$, $R^{5B}$, $R^{5C}$, $R^{5D}$, and $R^{5E}$ are each independently selected from H, $C_1$-$C_6$ alkyl, halo, $C_1$-$C_6$ haloalkyl, 3 to 7-membered cycloalkyl, —$OR^4$, —$N(R^4)_2$, —CN, —C(O)$R^4$, —C(O)$OR^4$, —C(O)$N(R^4)_2$ and —NHC(O)$R^4$;

$R^2$ is as defined in Embodiment E1 or as defined in any of Embodiments E5 through E13; and $R^3$ is as defined in Embodiment E1 or as defined in any of Embodiments E5 through E13;

or $R^2$ and $R^3$, together with the carbon atoms to which they are attached, optionally join to form a cyclic group Y, wherein Y is as defined in Embodiment E1 or as defined in any of Embodiments E22 though E29.

In one embodiment of Class C-1, A is $CH_2$; and all other variables are as defined in Class C-1 or as defined in any embodiment herein.

In another embodiment of Class C-1, up to 2 of $R^{5A}$, $R^{5B}$, $R^{5C}$, $R^{5D}$, and $R^{5E}$ are independently selected from H and halo and $R^2$ and $R^3$ are as defined in Class-C-1 or $R^2$ and $R^3$, together with the carbon atoms to which they are attached, optionally join to form a cyclic group Y, wherein Y is as defined in Embodiment E1 or as defined in any of Embodiments E22 though E29.

In yet another embodiment of Class C-1, $R^{5A}$, $R^{5E}$ are H; $R^{5B}$, $R^{5C}$, and $R^{5D}$, are each independently selected from H, F, and Cl; $R^2$ and $R^3$ are as defined in Class C-1 or $R^2$ and $R^3$, together with the carbon atoms to which they are attached, optionally join to form a cyclic group Y, wherein Y is as defined in Embodiment E1 or as defined in any of Embodiments E22 though E29.

Another class of compounds of the invention (alternatively referred to as Class C-2) includes compounds of Formula (Ib):

(Ib)

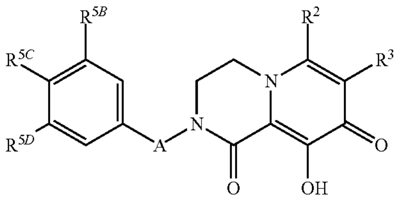

or a pharmaceutically acceptable salt thereof, wherein:

$R^{5B}$, $R^{5C}$, and $R^{5D}$, are each independently selected from H, F, and Cl;

$R^2$ is as defined in Embodiment E1 or as defined in any of Embodiments E5 through E13; and $R^3$ is as defined in Embodiment E1 or as defined in any of Embodiments E5 through E13;

or $R^2$ and $R^3$, together with the carbon atoms to which they are attached, optionally join to form a cyclic group Y, wherein Y is as defined in Embodiment E1 or as defined in any of Embodiments E22 though E29.

One embodiment of the invention is a compound of Class C-1 or Class C-2 or a pharmaceutically acceptable salt thereof, wherein the definitions of $R^{5B}$, $R^{5C}$, and $R^{5D}$ are selected from the group consisting of sets (a) to (c) as follows:

(a) $R^{5B}$ is H, $R^{5C}$ is F, and $R^{5D}$ is Cl;

(b) $R^{5B}$ is Cl, $R^{5C}$ is F, and $R^{5D}$ is H; and (c) $R^{5B}$ is H, $R^{5C}$ is F, and $R^{5D}$ is H;

wherein $R^2$ and $R^3$ are as defined in Class C-1; or $R^2$ and $R^3$, together with the carbon atoms to which they are attached, optionally join to form a cyclic group Y, wherein Y is as defined in Class C-1.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, nucleoside reverse transcriptase inhibitors and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, nucleoside reverse transcriptase inhibitors and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt. It is understood that references to compounds would include the compound in its present form as well as in different forms, such as polymorphs, solvates and hydrates, as applicable.

It is further to be understood that the embodiments of compositions and methods provided as (a) through (k) above include all embodiments of the compounds, including such embodiments that result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Uses of the 4-Pyridone Compounds:

The 4-Pyridone Compounds and pharmaceutical compositions comprising said 4-Pyridone Compounds are useful in human and veterinary medicine for treating or preventing HIV infection and/or the clinical manifestations thereof in a subject. The 4-Pyridone Compounds and compositions of the invention can be useful for treating a subject suffering from infection related to any HIV genotype. In a specific embodiment, the 4-Pyridone Compounds are inhibitors of HIV-1. In one embodiment, the clinical manifestation of the HIV infection has progressed to AIDS. In accordance with the invention, the 4-Pyridone Compounds can be administered to a subject in need of treatment or prevention of HIV infection, or the clinical symptoms thereof.

The 4-Pyridone Compounds can be useful in (1) the inhibition of HIV; (2) the treatment of HIV infection, (3) reduction of the likelihood, severity, or progression of symptoms of HIV infection; (4) the inhibition of HIV viral replication; (5) the inhibition of HIV viral production; and/or (6) reduction in the likelihood, severity, or progression of AIDS. For example, the 4-Pyridone Compounds are useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject comprising administering to the subject an effective amount of at least one 4-Pyridone Compound or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In another specific embodiment, the present invention provides methods for treating AIDS in a subject comprising administering to the subject an effective amount of at least one 4-Pyridone Compound or a pharmaceutically acceptable salt or prodrug thereof.

The 4-Pyridone Compounds are also useful in the preparation and execution of screening assays for antiviral compounds. For example the 4-Pyridone Compounds are useful for identifying resistant HIV cell lines harboring mutations, which are excellent screening tools for more powerful antiviral compounds. Furthermore, the 4-Pyridone Compounds are useful in establishing or determining the binding site of other antivirals to the HIV Integrase by competitive inhibition.

Combination Therapy:

The invention also relates to methods for treating or preventing HIV infection or AIDS comprising administering to a patient an effective amount of a 4-Pyridone compound, a pharmaceutically acceptable carrier, and one or more additional therapeutic agents which are not 4-Pyridone Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one 4-Pyridone Compound (which may include two or more different 4-Pyridone Compounds), or a pharmaceutically acceptable salt or prodrug thereof, and (ii) at least one additional therapeutic agent that is other than a 4-Pyridone Compound, wherein the amounts administered are together effective to treat or prevent a viral infection or the clinical symptoms thereof.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 4-Pyridone Compound and an additional therapeutic agent may be present in fixed amounts (dosage amounts) in a single dosage unit (e.g., a capsule, a tablet and the like).

In one embodiment, the at least one 4-Pyridone Compound is administered during a time when the additional therapeutic agent(s) exert their prophylactic or therapeutic effect, or vice versa.

In another embodiment, the at least one 4-Pyridone Compound and the additional therapeutic agent(s) are administered in doses commonly employed when such agents are used as monotherapy for treating a viral infection.

In another embodiment, the at least one 4-Pyridone Compound and the additional therapeutic agent(s) are administered in doses lower than the doses commonly employed when such agents are used as monotherapy for treating a viral infection.

In still another embodiment, the at least one 4-Pyridone Compound and the additional therapeutic agent(s) act synergistically and are administered in doses lower than the doses commonly employed when such agents are used as monotherapy for treating a viral infection.

In one embodiment, the at least one 4-Pyridone Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

The at least one 4-Pyridone Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

As noted herein, the present invention is also directed to use of a compound of Formula I or a salt or prodrug thereof with one or more anti-HIV agents. An "anti-HIV agent" is any agent that is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, dolutegravir, darunavir, atazanavir, emtricitabine, tenofovir, elvitegravir, rilpivirine and lopinavir.

In another embodiment, the compound of formula (I) is used in combination with a single anti-HIV drug which is raltegravir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In yet another embodiment, the compound of formula (I) is used in combination with a single anti-HIV drug which is dolutegravir.

In another embodiment, the compound of formula (I) is used in combination with a single anti-HIV drug which is elvitegravir.

In one embodiment, the compound of formula (I) is used in combination with two anti-HIV drugs which are lamivudine and abacavir.

In another embodiment, the compound of formula (I) is used in combination with two anti-HIV drugs which are darunavir and raltegravir.

In another embodiment, the compound of formula (I) is used in combination with two anti-HIV drugs which are emtricitabine and tenofovir.

In still another embodiment, the compound of formula (I) is used in combination with two anti-HIV drugs which are atazanavir and raltegravir.

In another embodiment, the compound of formula (I) is used in combination with two anti-HIV drugs which are ritonavir and lopinavir.

In another embodiment, the compound of formula (I) is used in combination with two anti-HIV drugs which are lamivudine and raltegravir.

In one embodiment, the compound of formula (I) is used in combination with three anti-HIV drug which are abacavir, lamivudine and raltegravir.

In another embodiment, the compound of formula (I) is used in combination with three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV agents selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of the clinical manifestation of HIV infection, e.g. AIDS, in a subject in need thereof, which comprises administering to the subject (i) a compound of formula (I) or a pharmaceutically acceptable salt thereof and (ii) one or more additional anti-HIV agents selected from lamivudine, abacavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of HIV and/or the clinical symptoms thereof, e.g. AIDS. The HIV antiviral agents and other agents will typically be employed in these combinations in their conventional dosage ranges and regimens as reported in the art, including, for example, the dosages described in the *Physicians' Desk Reference*, Thomson P D R, Thomson P D R, $57^{th}$ edition (2003), the $58^{th}$ edition (2004), the $59^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the 4-Pyridone Compound(s) and the other agent(s) can be administered simultaneously (i.e., in the same composition or in separate compositions one right after the other) or sequentially. This is particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Compositions and Administration:

When administered to a subject, the 4-Pyridone Compounds can be administered as a component of a composition that comprises a pharmaceutically acceptable carrier or vehicle. The present invention provides pharmaceutical compositions comprising an effective amount of at least one 4-Pyridone Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with an oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 4-Pyridone Compounds are administered orally.

In another embodiment, the one or more 4-Pyridone Compounds are administered intravenously.

In one embodiment, a pharmaceutical preparation comprising at least one 4-Pyridone Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the 4-Pyridone Compound(s) by weight or volume. In various embodiments, the present compositions can contain, in one embodiment, from about 1% to about 70% or from about 5% to about 60% of the 4-Pyridone Compound(s) by weight or volume.

The compounds of Formula I can be administered orally in a dosage range of 0.001 to 1000 mg/kg of mammal (e.g., human) body weight per day in a single dose or in divided doses. One exemplary dosage range is 0.01 to 500 mg/kg body weight per day orally in a single dose or in divided doses. Another exemplary dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 4-Pyridone Compounds will be regulated according to the judgment of the attending clinician considering such factors as age, condition and size of the subject as well as severity of the symptoms being treated.

Kits:

In one aspect, the present invention provides a kit comprising a therapeutically effective amount of at least one 4-Pyridone Compound, or a pharmaceutically acceptable salt or prodrug of said compound and a pharmaceutically acceptable carrier, vehicle or diluent.

In another aspect the present invention provides a kit comprising an amount of at least one 4-Pyridone Compound, or a pharmaceutically acceptable salt or prodrug of said compound and an amount of at least one additional therapeutic agent, e.g. the therapeutic agents listed above, wherein the amounts of the two or more active ingredients result in a desired therapeutic effect. In one embodiment, the one or more 4-Pyridone Compounds and the one or more additional therapeutic agents are provided in the same container. In one embodiment, the one or more 4-Pyridone Compounds and the one or more additional therapeutic agents are provided in separate containers.

Non-limiting examples of the Compounds of Formula (I) include compounds of formulas 1-5, 1-6, 2-8, 2-9, and 3-5 as set forth below, and pharmaceutically acceptable salts thereof.

Methods for Making the Compounds of Formula (I)

The Compounds of Formula (I) may be prepared from known or readily prepared starting materials, following methods known to one skilled in the art of organic synthesis and/or using techniques exemplified herein. Methods useful for making the Compounds of Formula (I) are set forth in the Examples below and generalized in Schemes 1-4 below. Alternative synthetic pathways and analogous structures will be apparent to those skilled in the art of organic synthesis.

Scheme 1 shows a method useful for making the compounds of: (i) formula 1-5, which corresponds to the compounds of formula (I), wherein A is —$CH_2$, $R^1$ is 3-chloro-4-fluorophenyl, and $R^2$ and $R^3$ combine to form a 6 to 8-membered oxygen-containing heterocycloalkenyl group and (ii) formula 1-6, which correspond to the compounds of formula (I), wherein A is —$CH_2$—; $R^1$ is 3-chloro-4-fluorophenyl; and $R^2$ and $R^3$ combine to form a 6 to 8-membered oxygen-containing heterocycloalkyl group.

Scheme 1

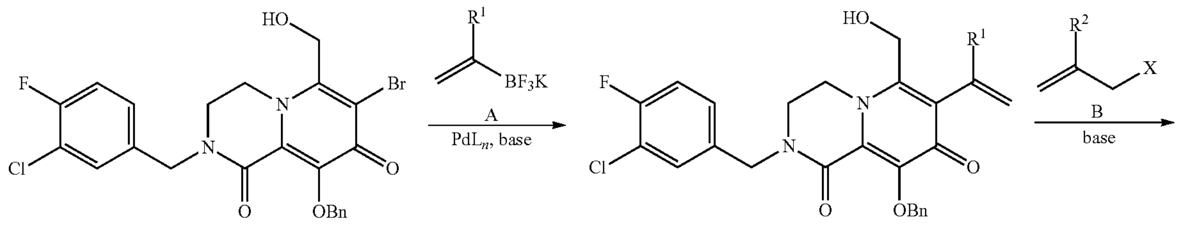

1-1

1-2

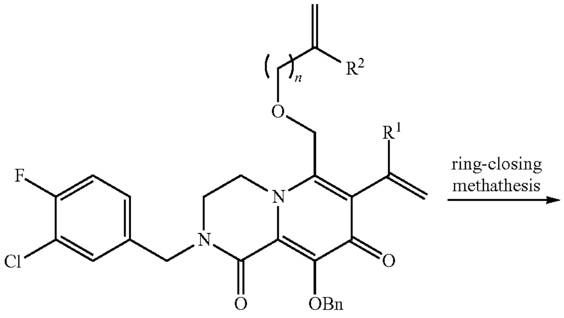

1-3

-continued

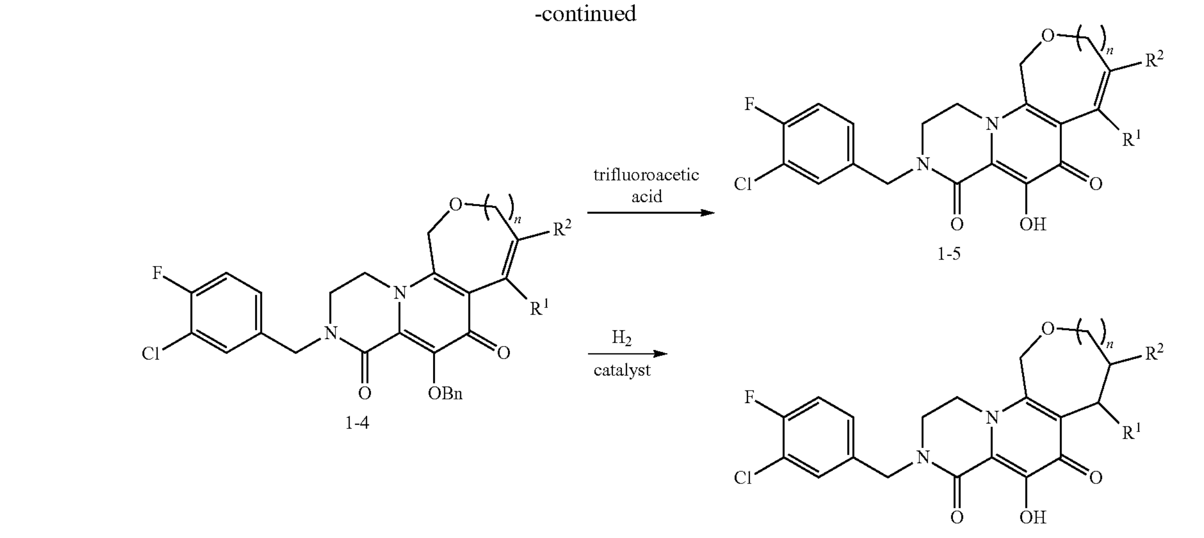

1-4

1-5

1-6

Wherein X is halo and n, $R^1$, $R^2$ and $R^3$ are as defined above for the compounds of formula (I).

A compound of formula 1-1 can undergo a palladium-catalyzed coupling with a vinyl boron compound of formula A to provide the compounds of formula 1-2. A compound of formula 1-2 can then be coupled with a substituted allyl halide of formula B to provide the compounds of formula 1-3. A compound of formula 1-3 can then undergo a ring metathesis process to provide the tricyclic compounds of formula 1-4. Removal of the benzyl protecting group from 1-4 using TFA provides the compounds of formula 1-5, which correspond to the compounds of formula (I), wherein A is —$CH_2$—; $R^1$ is 3-chloro-4-fluorophenyl; and $R^2$ and $R^3$ combine to form a 6 to 8-membered oxygen-containing heterocycloalkenyl group. Alternatively, removal of the benzyl protecting group from 1-4 using a catalytic hydrogenation provides the compounds of formula 1-6, which correspond to the compounds of formula (I), wherein A is —$CH_2$—; $R^1$ is 3-chloro-4-fluorophenyl; and $R^2$ and $R^3$ combine to form a 6 to 8-membered oxygen-containing heterocycloalkyl group.

Scheme 2 shows a method useful for making the compounds of: (ii) formula 2-7, which correspond to the compounds of formula (I), wherein A is —$CH_2$—; $R^1$ is 3-chloro-4-fluorophenyl; and $R^2$ and $R^3$ combine to form a 6 to 8-membered cyclic amido group which is substituted with a vinyl group; (ii) formula 2-8, which correspond to the compounds of formula (I), wherein A is —$CH_2$—; $R^1$ is 3-chloro-4-fluorophenyl; and $R^2$ and $R^3$ combine to form a 6 to 8-membered cyclic amido group which is substituted with an alkyl group.

Scheme 2

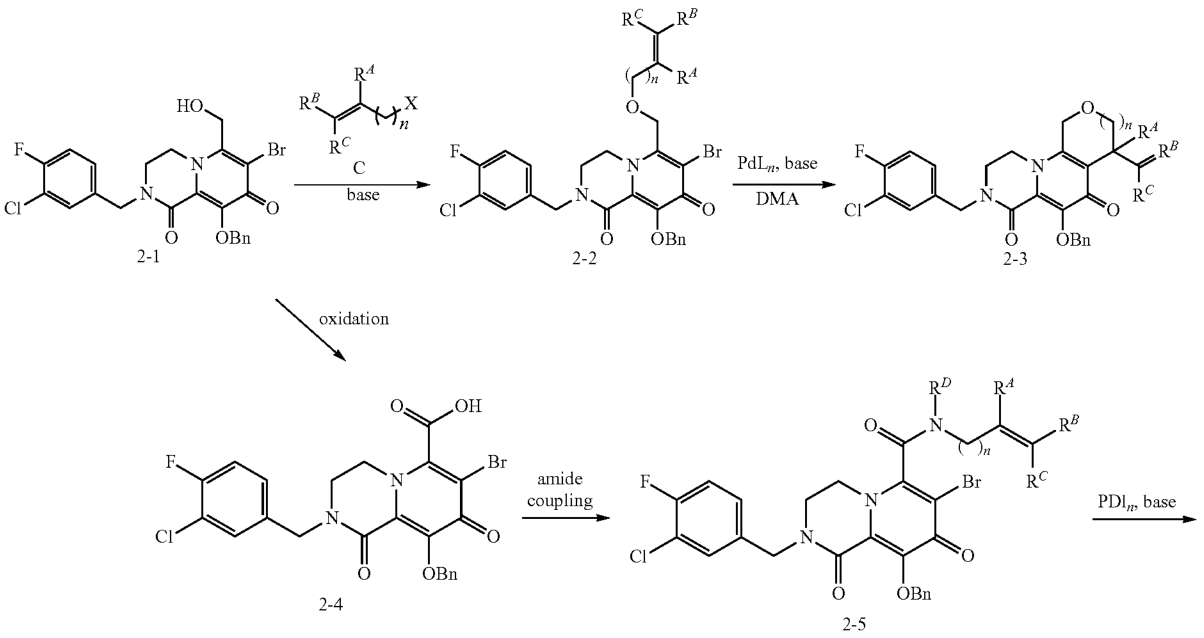

2-1

2-2

2-3

2-4

2-5

-continued

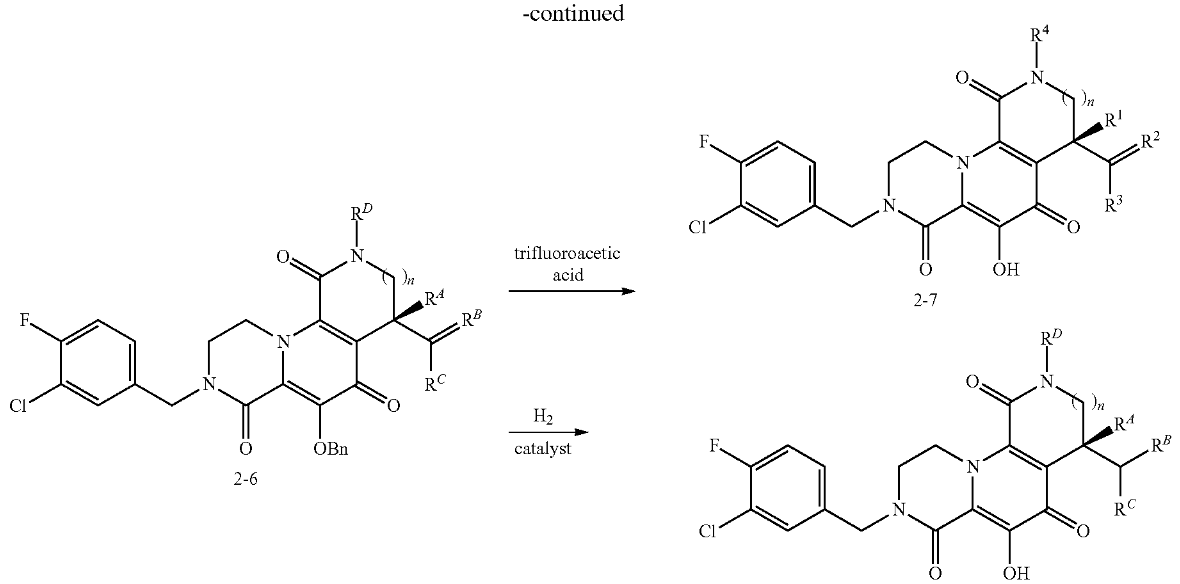

2-6 2-7 2-8

Wherein X is halo and n, $R^1$, $R^2$ and $R^3$ are as defined above for the compounds of formula (I).

A compound of formula 2-1 can be coupled with a substituted allyl halide of formula C to provide the compounds of formula 2-2. A compound of formula 2-2 can then undergo a palladium-catalyzed ring closure process to provide the tricyclic compounds of formula 2-3.

Alternatively, a compound of formula 2-1 can be oxidized to provide the carboxylic acid compounds of formula 2-4, which can then undergo an amide coupling with an appropriate amine to provide the amides of formula 2-5. A compound of formula 2-5 can then undergo a palladium-catalyzed ring closure process to provide the tricyclic compounds of formula 2-6. Removal of the benzyl protecting group from 2-6 using TFA provides the compounds of formula 2-7, which correspond to the compounds of formula (I), wherein A is —$CH_2$—; $R^1$ is 3-chloro-4-fluorophenyl; and $R^2$ and $R^3$ combine to form a 6 to 8-membered cyclic amido group which is substituted with a vinyl group. Alternatively, removal of the benzyl protecting group from 2-6 using a catalytic hydrogenation provides the compounds of formula 2-8, which correspond to the compounds of formula (I), wherein A is —$CH_2$—; $R^1$ is 3-chloro-4-fluorophenyl; and $R^2$ and $R^3$ combine to form a 6 to 8-membered cyclic amido group which is substituted with an alkyl group.

Scheme 3 shows a method useful for making the compounds of formula 3-5, which correspond to the compounds of formula (I), wherein A is —$CH_2$—; $R^1$ is 3-chloro-4-fluorophenyl; $R^2$ is amido and $R^3$ is defined above for the compounds of formula (I).

Scheme 3

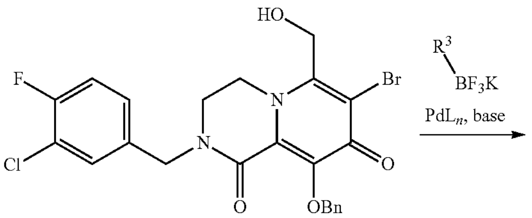

3-1

-continued

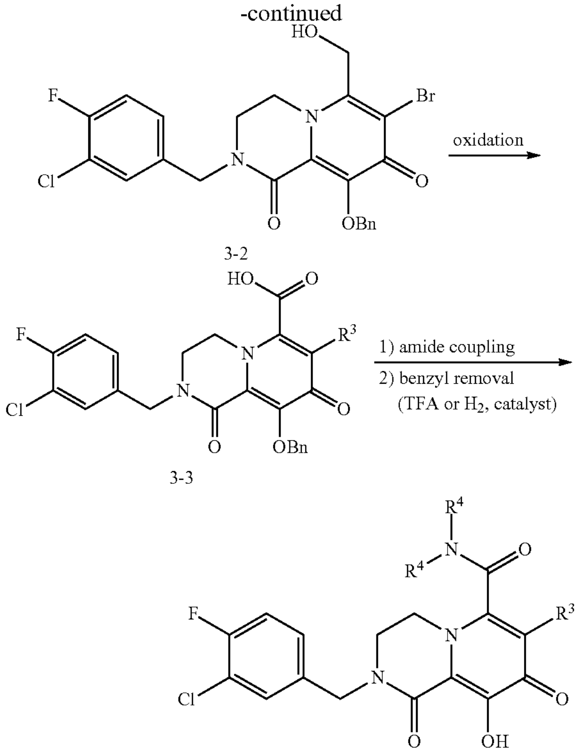

3-2 3-3 3-4

Wherein $R^1$, $R^2$ and $R^3$ are as defined above for the compounds of formula (I).

A compound of formula 3-1 can undergo a palladium-catalyzed coupling with a vinyl boron compound of formula $R^3$—$BF_3K$ to provide the compounds of formula 3-2, which can be oxidized to provide the compounds of formula 3-3. A compound of formula 3-3 can then undergo an amide coupling with an appropriate amine, followed by benzyl group removal (using TFA or catalytic hydrogenation) to provide the amides of formula 3-4, which correspond to the compounds of formula (I), wherein A is —$CH_2$—; $R^1$ is 3-chloro-4-fluorophenyl; $R^2$ is —C(O)N($R^4$) and $R^3$ is defined above for the compounds of formula (I).

Scheme 4 shows an alternate method useful for making the compounds of formula 3-4, which correspond to the compounds of formula (I), wherein A is —$CH_2$—; $R^1$ is 3-chloro-4-fluorophenyl; $R^2$ is —C(O)N($R^4$) and $R^3$ is defined above for the compounds of formula (I).

Scheme 4

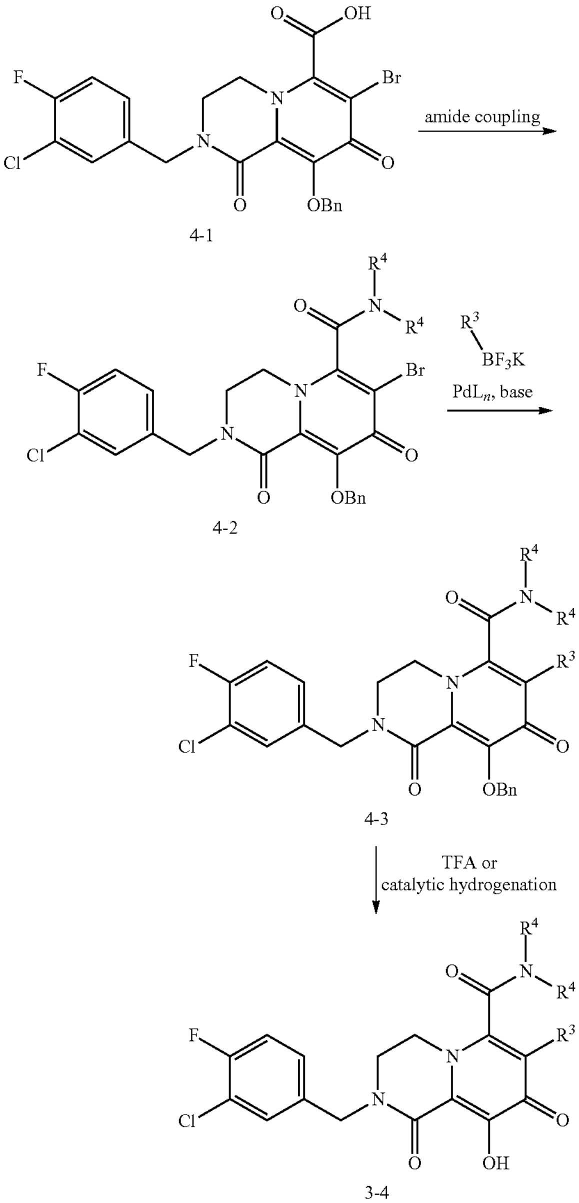

4-1

4-2

4-3

3-4

Wherein $R^1$, $R^2$ and $R^3$ are as defined above for the compounds of formula (I).

A compound of formula 4-1 can undergo an amide coupling with an appropriate amine to provide the amides of formula 4-2. A compound of formula 4-2 can undergo a palladium-catalyzed coupling with a vinyl boron compound of formula $R^3$—$BF_3K$ to provide the compounds of formula 4-3. Benzyl group removal provides compounds of formula 3-4, which correspond to the compounds of formula (I), wherein A is —$CH_2$—; $R^1$ is 3-chloro-4-fluorophenyl; $R^2$ is —C(O)N($R^4$)$_2$ and $R^3$ is defined above for the compounds of formula (I).

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well-known in the art of organic chemistry. A summary of many of these methods can be found in Greene & Wuts, *Protecting Groups in Organic Synthesis*, John Wiley & Sons, 3$^{rd}$ edition (1999). Additionally, one skilled in the relevant art will recognize that in some cases the order of reactions may differ from that presented herein to avoid functional group incompatibilities and thus adjust the synthetic route accordingly.

Compounds of formulas 1-5, 1-6, 2-7, 2-8, and 3-4 may be further elaborated using methods that would be well-known to those skilled in the art of organic synthesis or, for example, the methods described in the Examples below, to make the full scope of the Compounds of Formula (I).

The starting materials used and the intermediates prepared using the methods set forth in Schemes 1-4 may be isolated and purified if desired using conventional techniques, including but not limited to filtration, distillation, crystallization, chromatography and alike. Such materials can be characterized using conventional means, including physical constants and spectral data.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

EXAMPLES

General Methods

Reactions sensitive to moisture or air were performed under nitrogen using anhydrous solvents and reagents. The progress of reactions was determined by either analytical thin layer chromatography (TLC) performed with E. Merck precoated TLC plates, silica gel 60E-254, layer thickness 0.25 mm or liquid chromatography-mass spectrum (LC-MS). Analytical HPLC/MS—Standard Method: Mass analysis was performed with electrospray ionization in positive ion detection mode. For HPLC/MS data, the three HPLC conditions used were as follows: 1) LC2 (Waters C18 XTerra™ 3.5 μm 2.1×20 mm column with gradient 10:90-98:2 v/v $CH_3CN/H_2O$+v 0.05% TFA over 1.25 min then hold at 98:2 v/v $CH_3CN/H_2O$+v 0.05% TFA for 0.75 min; flow rate 1.5 mL/min, UV wavelength 254 nm); and 2) LC4 (Waters C18 XTerra 3.5 μm 2.1×20 mm column with gradient 10:90-98:2 v/v $CH_3CN/H_2O$+v 0.05% TFA over 3.25 min then hold at 98:2 v/v $CH_3CN/H_2O$+v 0.05% TFA for 0.75 min; flow rate 1.5 mL/min, UV wavelength 254 nm).

Preparative reverse phase high performance liquid chromatography (RP-HPLC) used for the purification of samples was performed using a Gilson™ RP-HPLC system with a Waters Sunfire C18 ODB, 5 uM, 19 mm×100 mm, 25 mL/min gradient elution 10:90 to 75:25 $CH_3CN/H_2O$+v 0.05% TFA over 10 min unless indicated otherwise. Concentration of solutions was carried out on a rotary evaporator under reduced pressure or by lyophilization. Flash chromatography was performed on pre-packed silica gel columns using a commercial MPLC system.

Example 1

Preparation of Compounds 1, 2, and 3

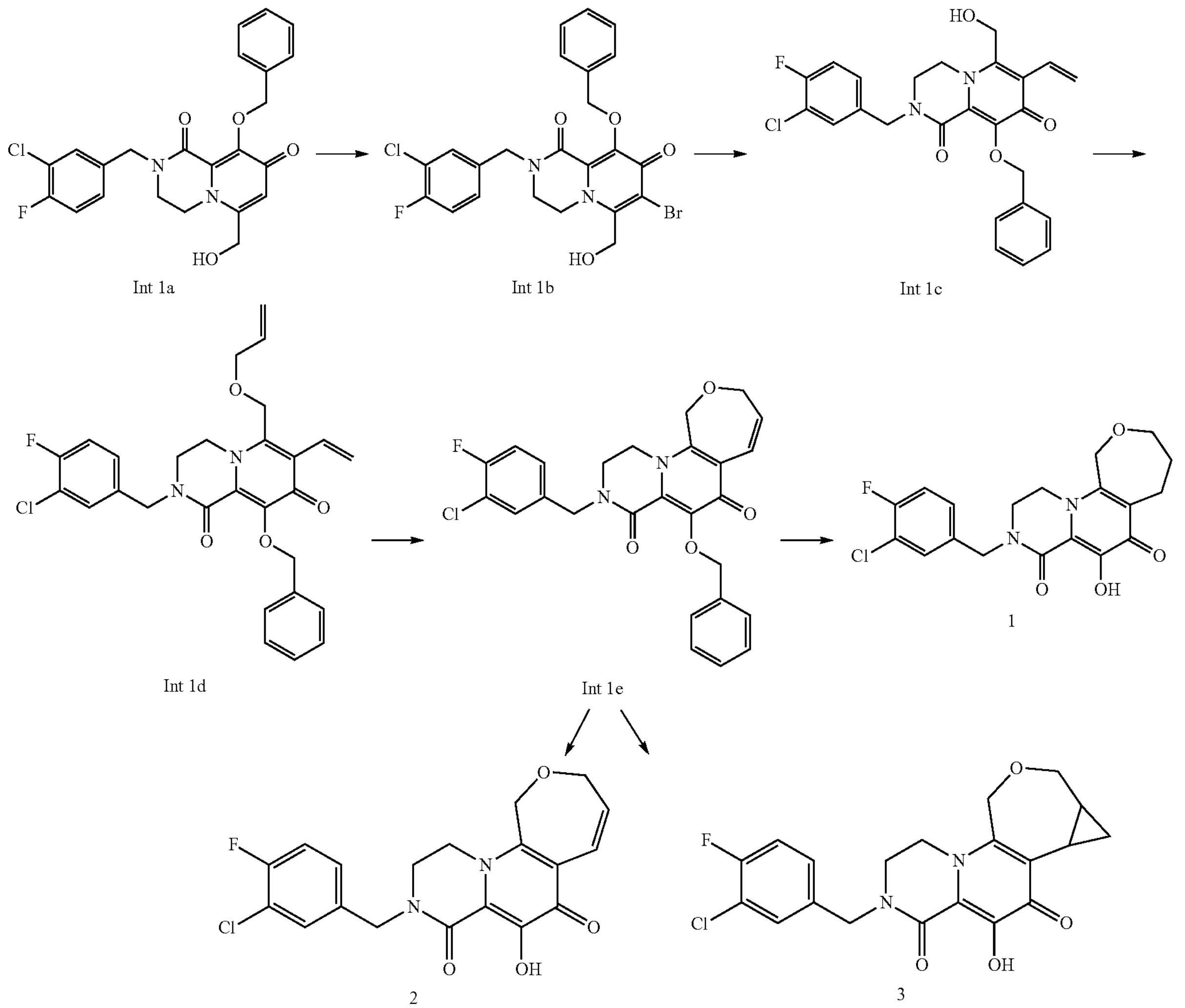

Int 1a, Int 1b, Int 1c, Int 1d, Int 1e, 1, 2, 3

Step A—Preparation of Intermediate Compound Int 1a {9-(benzyloxy)-2-(3-chloro-4-fluorobenzyl)-6-(hydroxymethyl)-3,4-dihydro-1H-pyrido[1,2-a]pyrazine-1,8(2H)-dione}

Step 1:

Into a 20-L 4-necked round-bottom flask purged and maintained with an inert atmosphere of nitrogen, was placed a solution of 3-(benzyloxy)-6-[(oxan-2-yloxy)methyl]-4-oxo-4H-pyran-2-carboxylic acid (1.10 kg, 3.05 mol, 1.00 equiv) (prepared according to US Patent Publication No. 2007/155744 A1) in dichloromethane (9.9 L), tert-butyl-N-(2-[3-chloro-4-fluorophenyl)methyl]aminoethyl)carbamate (1.11 kg, 3.66 mol, 1.20 equiv), DIEA (802.38 g, 6.21 mol, 2.03 equiv). The solution was first cooled to 0° C., then HATU was added (1265.60 g, 3.33 mol, 1.09 equiv). The resulting solution was stirred overnight at room temperature. The reaction was then quenched by the addition of water (2 L). The resulting solution was extracted with dichloromethane (3×3 L). The organic layers were combined, dried and concentrated under vacuum. The residue was purified using flash column chromatography on silica gel and eluted with dichloromethane/methanol (5:1) resulting in 1.57 kg (80%) of tert-butyl-N-(2-[1-[3-(benzyloxy)-6-[(oxan-2-yloxy)methyl]-4-oxo-4H-pyran-2-yl]-N-[(3-chloro-4-fluorophenyl)methyl]formamido]ethyl)carbamate as a solid that was used without further purification.

Step 2:

Into a 20-L 4-necked round-bottom flask purged and maintained with an inert atmosphere of nitrogen, was placed the product from Step 1 (1.57 kg, 2.43 mol, 1.00 equiv), and HCl/dioxane (4M, 7850 mL). The resulting solution was stirred overnight at room temperature. The solids were collected by filtration and then washed with ether. This resulted in 1.08 kg (89%) of N-(2-aminoethyl)-3-(benzyloxy)-N-[(3-chloro-4-fluorophenyl)methyl]-6-(hydroxymethyl)-4-oxo-4H-pyran-2-carboxamide hydrochloride as a solid.

Step 3:

Into three 20-L 4-necked round-bottom flasks purged and maintained with an inert atmosphere of nitrogen, was placed a solution of the product from Step 2 (360 g, 723.85 mmol, 1.00 equiv) in ethanol (14.4 L) and aqueous sodium carbonate (3.6 L). The resulting solution was stirred for 3 hours at 50° C. The reaction mixture was cooled to 10° C. The solids were collected by filtration, washed with $H_2O$, and air-dried to afford Int 1a. LC-MS-(ES, m/z) 443 $[M+H]^+$. $^1$NMR-(400 MHz, DMSO-d6, ppm): δ 7.61 (1H, m), 7.52 (2H, m), 7.27-7.44 (5H, m), 6.40 (1H, s), 5.67 (1H, m), 5.09 (2H, s), 4.67 (2H, s), 4.44 (2H, d, J=8 Hz), 4.05 (2H, m), 3.60 (2H, m).

Step B—Preparation of Intermediate Compound Int 1b {9-(benzyloxy)-7-bromo-2-(3-chloro-4-fluorobenzyl)-6-(hydroxymethyl)-3,4-dihydro-1H-pyrido[1,2-a]pyrazine-1,8(2H)-dione}

Into a 20-L 4-necked round-bottom flask purged and maintained with an inert atmosphere of nitrogen, was placed a solution of Int 1a (550 g, 1.24 mol, 1.00 equiv) in N-methyl pyrrolidinone (8250 mL), N-bromosuccinimide (243.6 g, 1.37 mol, 1.10 equiv). The resulting solution was stirred for 3 hours at room temperature. The reaction was then quenched by the addition of water/ice. The solids were collected by filtration, washed with water, and air-dried to afford Int 1b as a solid. LC-MS (ES, m/z) 521 $[M+H]^+$ $^1$H NMR (300 MHz, DMSO-d6, ppm): δ 7.61-7.51 (3H, m), 7.45-7.28 (5H, m), 5.86 (1H, s), 5.08 (2H, s), 4.85 (2H, s), 4.67 (2H, s), 4.31 (2H, s), 3.64 (2H, s).

Step C—Preparation of Intermediate Compound Int 1c {9-(benzyloxy)-2-(3-chloro-4-fluorobenzyl)-6-(hydroxymethyl)-7-vinyl-3,4-dihydro-1H-pyrido[1,2-a]pyrazine-1,8(2H)-dione}

A solution of Int 1b (20 mg, 0.038 mmol), potassium vinyltrifluoroborate (16.94 mg, 0.126 mmol), potassium carbonate (21.19 mg, 0.153 mmol) and $PdCl_2$(DPPF)-Dichloromethane (3.13 mg, 3.83 μmol) in DMF (1 ml) was sub-surface sparged with nitrogen at room temperature for 2 minutes. The vial was capped and heated without stirring at 100° C. for 4 hours and then cooled to room temperature. Direct purification by preparative RP-HPLC afforded Int 1c. (ESI-MS) m/z 469.05; $R_t$ 1.1 min (LC2)

Step D—Preparation of Intermediate Compound Int d {6-((allyloxy)methyl)-9-(benzyloxy)-2-(3-chloro-4-fluorobenzyl)-7-vinyl-3,4-dihydro-1H-pyrido[1,2-a]pyrazine-1,8(2H)-dione}

A solution of Int 1c (25 mg, 0.053 mmol) and 3-iodoprop-1-ene (26.9 mg, 0.160 mmol) in DMSO (0.5 ml) was treated with potassium hydroxide (8.97 mg, 0.160 mmol). The mixture was stirred at room temperature for 12 hours, quenched with glacial AcOH (0.1 mL) and purified using preparative RP-HPLC to afford Int 1d. (ESI-MS) m/z 509.10; $R_t$ 1.3 min (LC2)

Step E—Preparation of Intermediate Compound Int 1e {7-(benzyloxy)-9-(3-chloro-4-fluorobenzyl)-10,11-dihydro-1H-oxepino[4',3':5,6]pyrido[1,2-a]pyrazine-6,8(3H,9H)-dione}

Int 1d (20 mg, 0.039 mmol) (0325085-0154) in anhydrous dichloromethane (4.0 ml) was sub-surface sparged with nitrogen for 2 minutes and Zhan catalyst PLC-301 (2 mg) was added. Sparging was continued for an additional 2 minutes; then the vial was capped and stirred at 50° C. for 2 hours. The mixture was concentrated in vacuo and the residue was purified using preparative RP-HPLC to afford Int 1e. (ESI-MS) m/z 481.03; $R_t$ 1.2 min (LC2)

Step F—Preparation of Compound 1 {9-(3-chloro-4-fluorobenzyl)-7-hydroxy-4,5,10,11-tetrahydro-1H-oxepino[4',3':5,6]pyrido[1,2-a]pyrazine-6,8(3H,9H)-dione}

A vial containing a solution of Int 1e (5.0 mg, 10.40 μmol) and Pd/C (11.06 mg, 10.40 μmol) in ethyl acetate (1.0 ml) was stirred under hydrogen (1 atm) for 1 hour. The mixture was filtered and the filtrate was concentrated in vacuo. Purification by preparative RP-HPLC afforded Compound 1. (ESI-MS) m/z 393.0; $R_t$ 1.6 min (LC4)

Step G—Preparation of Compound 2 {9-(3-chloro-4-fluorobenzyl)-7-hydroxy-10,11-dihydro-1H-oxepino[4',3':5,6]pyrido[1,2-a]pyrazine-6,8(3H,9H)-dione}

A vial containing a solution of Int 1e (5.0 mg, 10.40 μmol), dichloromethane (0.5 ml) and trifluoroacetic acid (0.5 ml) was stirred at room temperature for 18 hours. The mixture was concentrated and the residue was purified using preparative RP-HPLC to afford Compound 2. (ESI-MS) m/z 391.0; Rt 1.5 min (LC4)

Step H—Preparation of Compound 3 {2-(3-chloro-4-fluorobenzyl)-11-hydroxy-3,4,8,8a,9,9a-hexahydrocyclopropa[5',6]oxepino[4',3':5,6]pyrido[1,2-a]pyrazine-1,10(2H,6H)-dione}

A vial containing a solution of Int 1e (18 mg, 0.037 mmol) in dichloromethane (2.0 ml) was cooled to 0° C. and treated with trifluoroacetic acid (0.014 ml, 0.187 mmol), diiodomethane (0.015 ml, 0.187 mmol) and diethylzinc (0.187 ml, 0.187 mmol). The mixture was allowed to warm to room temperature and stirred for 12 hours, then quenched with saturated aqueous $NH_4Cl$. The aqueous layer was separated and discarded. The organic layer was concentrated. Purification of the residue by preparative RP-HPLC afforded Compound 3. (ESI-MS) m/z 405.11; Rt 1.5 min (LC4)

Example 2

Preparation of Compound 4

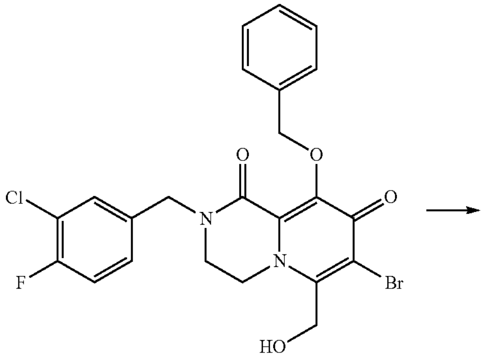

Int 1b

-continued

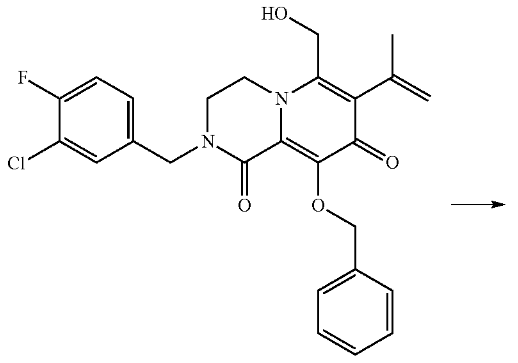

Int 2a

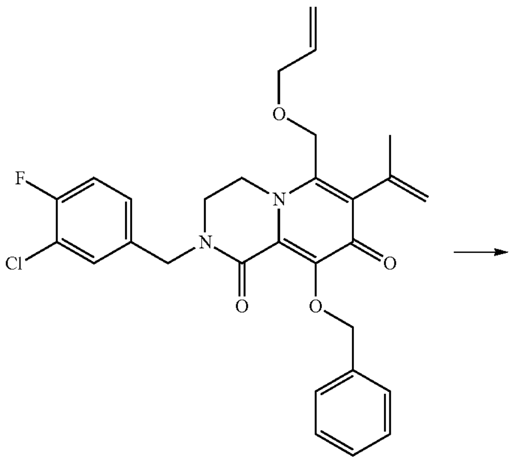

Int 2b

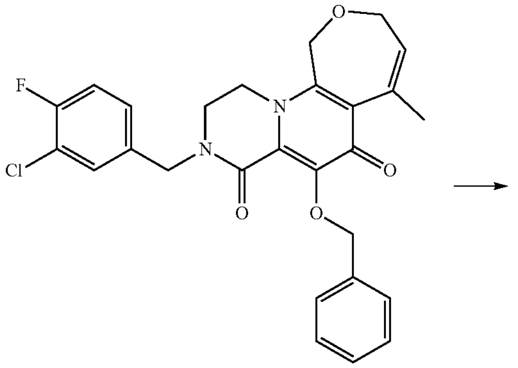

Int 2c

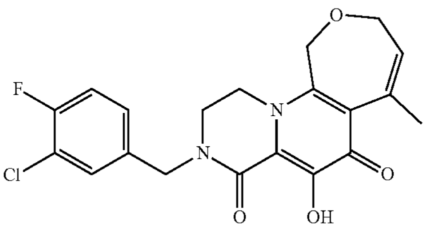

4

Step A—Preparation of Intermediate Compound Int 2a {9-(benzyloxy)-2-(3-chloro-4-fluorobenzyl)-6-(hydroxymethyl)-7-(prop-1-en-2-yl)-3,4-dihydro-1H-pyrido[1,2-a]pyrazine-1,8(2H)-dione}

A solution of Int 1b (250 mg, 0.479 mmol), potassium trifluoro(prop-1-en-2-yl)borate (213 mg, 1.437 mmol), potassium carbonate (199 mg, 1.437 mmol) and PdCl2 (dppf)-dichloromethane adduct (39.1 mg, 0.048 mmol) in DMF (1.0 ml) was sparged with nitrogen (subsurface) at room temperature for 2 minutes. The vial was capped and heated at 105° C. for 4 hours, then cooled to room temperature. Product mass was determined to be (m/z=483.06, Rt 1.8 min, LC4) and debenzyl product (m/z=393.02, Rt 1.5 min, LC4). The product was filtered, diluted with DMSO, and neutralized with glacial AcOH (0.1 mL) and water (0.1 mL). Purification by preparative RP-HPLC afforded Int 2a. (ESI-MS) m/z 483.22; $R_t$ 1.7 min (LC4)

Step B—Preparation of Intermediate Compound Int 2b {6-((allyloxy)methyl)-9-(benzyloxy)-2-(3-chloro-4-fluorobenzyl)-7-(prop-1-en-2-yl)-3,4-dihydro-1H-pyrido[1,2-a]pyrazine-1,8(2H)-dione}

A solution of Int 2a (100 mg, 0.207 mmol) and 3-iodo-prop-1-ene (174 mg, 1.035 mmol) in toluene (1.0 ml) was treated at room temperature with tetrabutylammonium hydrogen sulfate (14.06 mg, 0.041 mmol), sodium hydroxide (828 mg, 10.35 mmol) and water (1 mL). It was then stirred at room temperature for 16 hours. Water was added and the mixture was extracted with ethyl acetate. The combined organic layers were washed with brine, dried ($Na_2SO_4$), and filtered and the filtrate was concentrated in vacuo. Purification via flash column chromatography on silica gel (0 to 10% methanol/dichloromethane) afforded Int 2b. (ESI-MS) m/z 523.24; $R_t$ 1.2 min (LC2)

Step C—Preparation of Intermediate Compound Int 2c {6-(benzyloxy)-8-(3-chloro-4-fluorobenzyl)-4-methyl-9,10-dihydropyrano[4,3':5,6]pyrido[1,2-a]pyrazine-5,7(1H, 8H)-dione}

A solution of Int 2b (52 mg, 0.099 mmol) in dichloromethane (4.0 ml) was subsurface sparged (nitrogen) and treated with Hoveyda-Grubbs $2^{nd}$ generation catalyst (6.23 mg, 9.94 μmol). Sparging continued for 2 minutes; then the vial was capped and heated at 50° C. for 12 hours, then the mixture was cooled to room temperature. Purification via flash column chromatography on silica gel (0 to 10% methanol/Dichloromethane) followed by purification by preparative RP-HPLC afforded Int 2c. (ESI-MS) m/z, 495.07; $R_t$ 1.2 min (LC2)

Step D—Preparation of Compound 4 {9-(3-chloro-4-fluorobenzyl)-7-hydroxy-5-methyl-10,11-dihydro-1H-oxepino[4',3':5,6]pyrido[1,2-a]pyrazine-6,8(3H, 9H)-dione}

A solution of Int 2c (5.0 mg, 10.10 μmol) and Pd/C (10% dry powder) (10.75 mg, 10.10 μmol) in methanol was stirred at room temperature under hydrogen (1 atm) for 4 hours. The mixture was filtered and the filtrate was concentrated in vacuo. Purification of the residue by preparative RP-HPLC afforded Compound 4. (ESI-MS) m/z, 405.10; $R_t$ 1.7 min (LC4)

Example 3

Preparation of Compound 5

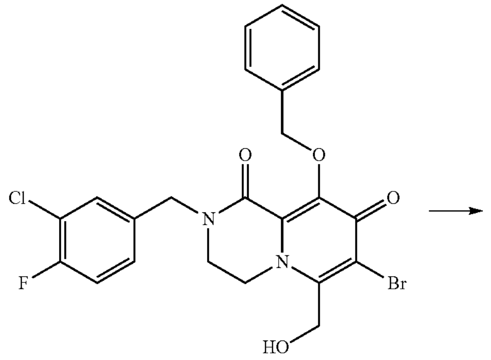

Int 1b

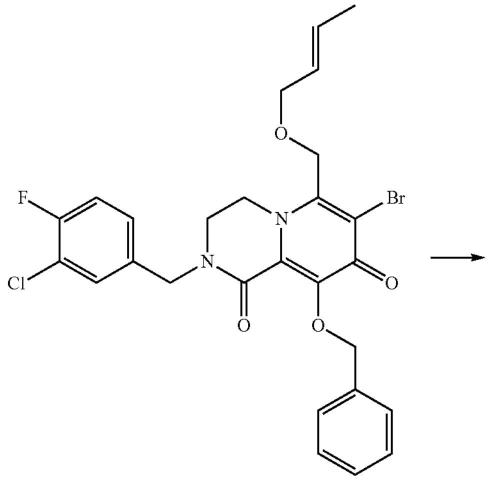

Int 3a

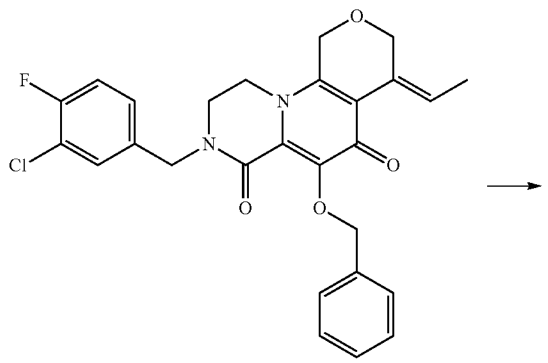

Int 3b

-continued

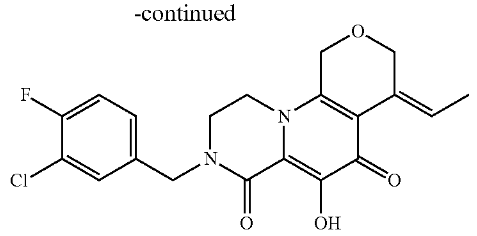

5

Step A—Preparation of Intermediate Compound Int 3a {(E)-9-(benzyloxy)-7-bromo-6-((but-2-en-1-yloxy)methyl)-2-(3-chloro-4-fluorobenzyl)-3,4-dihydro-1H-pyrido[1,2-a]pyrazine-1,8(2H)-dione}

To a solution of Int 1b (100 mg, 0.192 mmol) and tetra-N-butylammonium hydrogen sulfate (6.51 mg, 0.019 mmol) in toluene (1.0 ml) and water (1.000 ml) at room temperature was added sodium hydroxide (0.101 ml, 1.917 mmol) and crotyl bromide (103 mg, 0.767 mmol). The mixture was stirred at room temperature for 24 hours; then poured into water and extracted with ethyl acetate. The combined organic layers were washed with brine, dried ($Na_2SO_4$), filtered and the filtrate was concentrated in vacuo. Purification of the residue using flash column chromatography on silica gel (0 to 10% methanol/dichloromethane) afforded Int 3a. (ESI-MS) m/z, 577.07, 575.08; $R_t$ 2.3 min (LC4)

Step B—Preparation of Intermediate Compound Int 3b {6-(benzyloxy)-8-(3-chloro-4-fluorobenzyl)-4-vinyl-3,4,9,10-tetrahydropyrano[4,3':5,6]pyrido[1,2-a]pyrazine-5,7(1H, 8H)-dione}

A solution of Int 3a (80 mg, 0.139 mmol) in DMA (2 ml) was sparged with nitrogen for 2 minutes at room temperature, then $Pd(Ph_3P)_4$ (32.1 mg, 0.028 mmol) and triethylamine, were added and the reaction was sparged with nitrogen for 2 minutes, capped and heated at 110° C. for 3 hours. The mixture was cooled to room temperature and filtered. Direct purification by preparative RP-HPLC afforded Int 3b. (ESI-MS) m/z 495.04; $R_t$ 1.9 min (LC4)

Step C—Preparation of Compound 5 {(Z)-8-(3-chloro-4-fluorobenzyl)-4-ethylidene-6-hydroxy-3,4,9,10-tetrahydropyrano[4',3':5,6]pyrido[1,2-a]pyrazine-5,7(1H,8H)-dione}

A solution of Int 3b (31 mg, 0.063 mmol) in trifluoroacetic acid (2.0 ml) was stirred at room temperature for 12 hours. The mixture was then concentrated in vacuo and the residue was purified using preparative RP-HPLC to afford Compound 5. (ESI-MS) m/z 405.00; $R_t$ 1.6 min (LC4)

The following compounds of the present invention were made using the methods described in the Examples above and substituting the appropriate reactants and/or reagents. Saturated Compounds 6, 7, 25 and 27 were prepared by catalytic hydrogenation in a similar manner to Compound 1. Compounds 6 and 7, obtained as a mixture from the catalytic hydrogenation reaction, were separated using preparation HPLC.

| Compd # | Structure | Starting Material | Parent ion m/z (ESI-MS) |
|---|---|---|---|
| 6 | 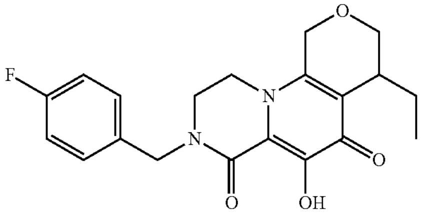 [SMILES: CCC1COCc2c1c(=O)c(O)c1n2CCN(Cc2ccc(F)cc2)C1=O] | Int 3b | 373 |
| 7 | 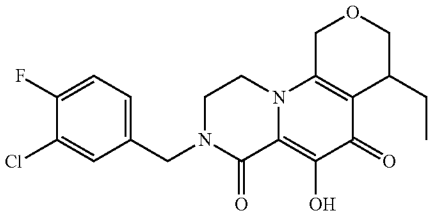 [SMILES: CCC1COCc2c1c(=O)c(O)c1n2CCN(Cc2ccc(F)c(Cl)c2)C1=O] | Int 3b | 407 |
| 25 | 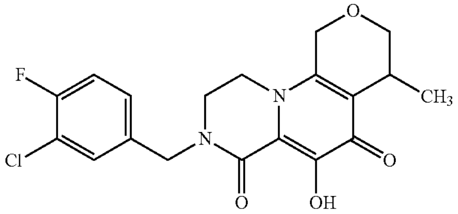 [SMILES: CC1COCc2c1c(=O)c(O)c1n2CCN(Cc2ccc(F)c(Cl)c2)C1=O] | Int 6b | 393 |
| 26 | 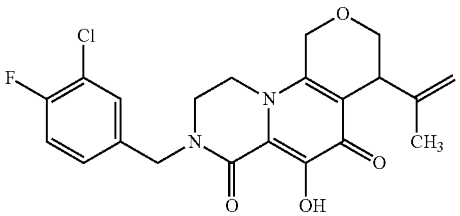 [SMILES: C=C(C)C1COCc2c1c(=O)c(O)c1n2CCN(Cc2ccc(F)c(Cl)c2)C1=O] | Int 1b | 419 |
| 27 | 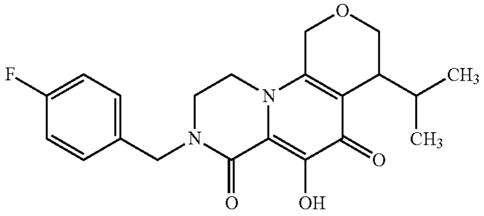 [SMILES: CC(C)C1COCc2c1c(=O)c(O)c1n2CCN(Cc2ccc(F)cc2)C1=O] | Int 1b | 387 |
Example 4
Preparation of Compound 8
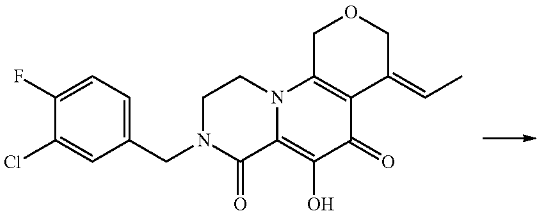
5
-continued
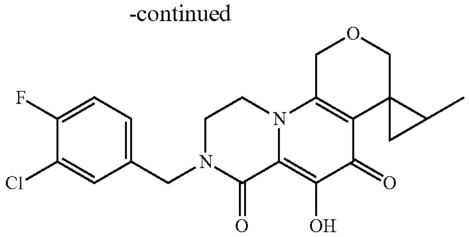
8
Preparation of Compound 8 {8'-(3-chloro-4-fluorobenzyl)-6'-hydroxy-2-methyl-9',10'-dihydro-1'H-spiro[cyclopropane-1,4'-pyrano[4',3':5,6]pyrido[1,2-a]pyrazine]-5',7'(3'H,8'H)-dione}
A solution of Compound 5 (10 mg, 0.025 mmol) and diiodomethane (0.020 ml, 0.247 mmol) in dichloromethane (1.0 ml) was cooled to 0° C. under nitrogen and treated dropwise with diethylzinc (1 M in hexanes) (0.247 ml, 0.247 mmol). The resulting suspension was stirred at 0° C. for 30 minutes then at room temperature for 15 minutes, then cooled to 0° C. and treated dropwise with 2 M aqueous $NaHSO_4$ (0.25 mL). The mixture was warmed to room temperature, and water (1.0 mL) was added. After vigorous agitation, the layers were separated and the aqueous layer was discarded. The organic layer was concentrated. The residue was purified using preparative RP-HPLC to afford Compound 8. (ESI-MS) m/z 419.07; $R_t$ 1.7 min (LC4)

Example 5

Preparation of Compound 9

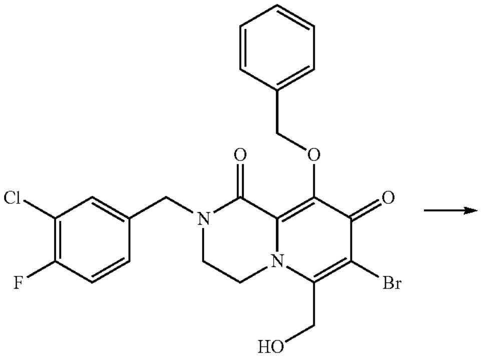

Int 1b

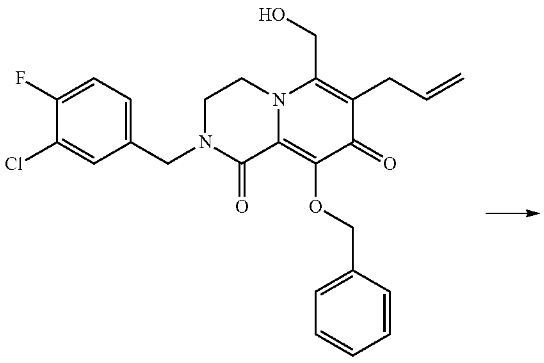

Int 5a

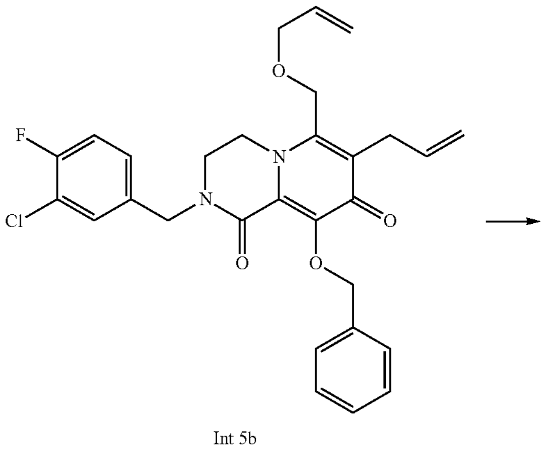

Int 5b

-continued

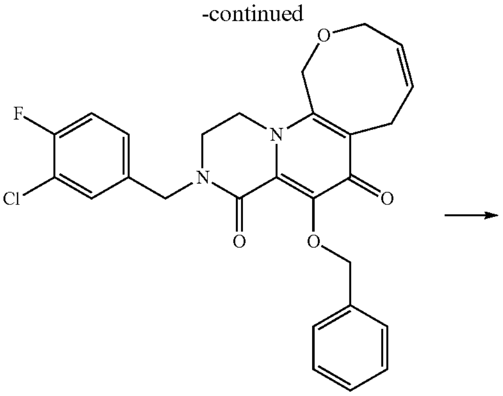

Int 5c

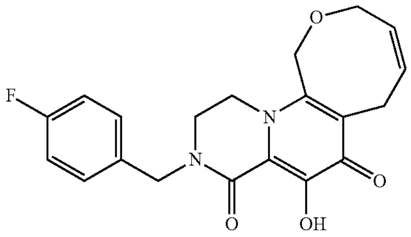

9

Step A—Preparation of Intermediate Compound Int 5a {7-allyl-9-(benzyloxy)-2-(3-chloro-4-fluorobenzyl)-6-(hydroxymethyl)-3,4-dihydro-1H-pyrido[1,2-a]pyrazine-1,8(2H)-dione}

A solution of Int 1b (250 mg, 0.479 mmol), allyl tri-N-butyltin (0.297 ml, 0.958 mmol) and $Pd(Ph_3P)_4$ (27.7 mg, 0.024 mmol) in THF (2.0 ml) was sparged with nitrogen (subsurface) at room temperature for 2 minutes. The vial was capped and heated at 100° C. for 8 hours. The resulting clear, yellow solution was cooled to room temperature. Purification by preparative RP-HPLC afforded Int 5a. (ESI-MS) m/z 483.19; $R_t$ 1.7 min (LC4)

Step B—Preparation of Intermediate Compound Int 5b {7-allyl-6-((allyloxy)methyl)-9-(benzyloxy)-2-(3-chloro-4-fluorobenzyl)-3,4-dihydro-1H-pyrido[1,2-a]pyrazine-1,8(2H)-dione}

A solution of Int 5a (44 mg, 0.091 mmol) and tetrabutylammonium hydrogen sulfate (6.19 mg, 0.018 mmol) in toluene (0.5 ml) and water (0.250 ml) was treated with NaOH (50 wt %) (0.241 ml, 4.56 mmol) and allyl bromide (0.079 ml, 0.911 mmol). The mixture was vigorously stirred for 16 hours at room temperature, followed by an aqueous workup (Ethyl acetate extraction) and purification via flash column chromatography on silica gel (0 to 10% methanol/CH2Cl2) to afford Int 5b. (ESI-MS) m/z 523.11; $R_t$ 2.1 min (LC4)

Step C—Preparation of Intermediate Compound Int 5c {(Z)-8-(benzyloxy)-10-(3-chloro-4-fluorobenzyl)-6, 10,11,12-tetrahydrooxocino[4,3':5,6]pyrido [1,2-a]pyrazine-7,9(1H,3H)-dione}

A solution of Int 5b (30 mg, 0.057 mmol) in dichloromethane (6.0 ml) was sub-surface sparged with nitrogen, treated with Zhan catalyst PLC-301, capped and heated at 50° C. for 6 hours. The mixture was cooled to room temperature and concentrated in vacuo. Purification of the residue using flash column chromatography on silica gel (0 to 10% methanol/$CH_2Cl_2$) followed by purification by preparative RP-HPLC afforded Int 5c. (ESI-MS) m/z 495.05; Rt 1.9 min (LC4)

Step D—Preparation of Compound 9 {10-(4-fluorobenzyl)-8-hydroxy-3,4,5,6,11,12-hexahydrooxocino[4,3':5,6]pyrido[1,2-a]pyrazine-7, 9(1H, 1 OH)-dione}

A solution of Int 5c (4.86 mg, 0.012 mmol) and Pd/C (10%, 1 mg) in methanol (1 ml) was stirred under hydrogen (1 atm) for 12 hours. The mixture was filtered using a PTFE-membrane syringe filter and the filtrate was concentrated. Purification by preparative RP-HPLC afforded Compound 9 (ESI-MS) m/z 373.15; Rt 1.1 min (LC2)

Example 6

Preparation of Compound 11

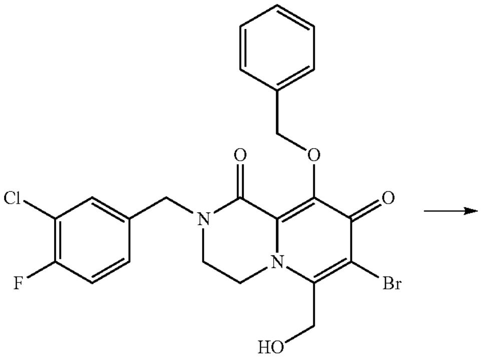

Int 1b

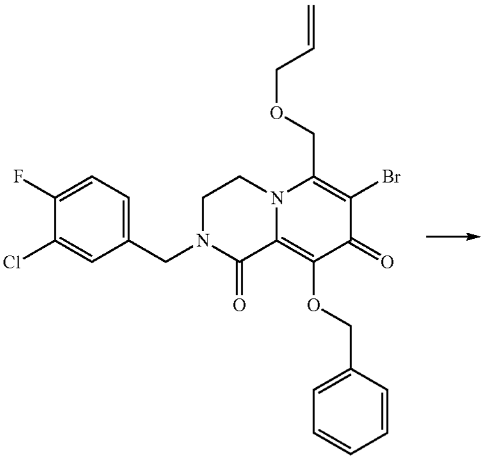

Int 6a

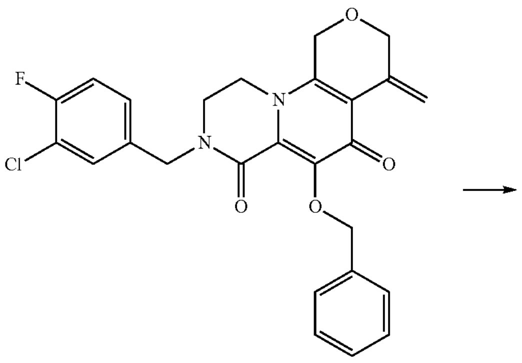

Int 6b

-continued

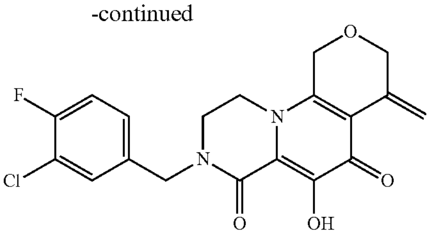

11

Step A—Preparation of Intermediate Compound Int 6a {6-((allyloxy)methyl)-9-(benzyloxy)-7-bromo-2-(3-chloro-4-fluorobenzyl)-3,4-dihydro-1H-pyrido[1,2-a]pyrazine-1,8(2H)-dione}

A solution of Int 1b (1000 mg, 1.917 mmol) in toluene (5.0 ml) and water (2.5 ml) was treated with tetrabutylammonium hydrogen sulfate (65.1 mg, 0.192 mmol), allyl bromide (0.829 ml, 9.58 mmol) and sodium hydroxide (50% wt, aq) (2.53 ml, 47.9 mmol). The mixture was vigorously stirred for 24 hours. Additional allyl bromide (2nd charge) (0.829 ml, 9.58 mmol) was added and stirred for an additional 24 hours. The mixture was then poured into water (100 mL) and extracted with ethyl acetate (3×50 mL). The combined organic layers were washed with brine, dried ($Na_2SO_4$), and filtered and the filtrate was concentrated in vacuo. Purification via flash column chromatography on silica gel (0 to 10% methanol/dichloromethane) afforded Int 6a. (ESI-MS) m/z 563.02, 561.04; $R_t$ 2.2 min (LC4)

Step B—Preparation of Intermediate Compound Int 6b {6-(benzyloxy)-8-(3-chloro-4-fluorobenzyl)-4-methylene-3,4,9,10-tetrahydropyrano[4',3':5,6]pyrido[1,2-a]pyrazine-5,7(1H,8H)-dione}

A solution of Int 6a (100 mg, 0.178 mmol) in DMA (2 ml) was sparged with nitrogen for 2 minutes, treated at room temperature with $Pd(Ph_3P)_4$ (41.1 mg, 0.036 mmol) and triethylamine, sparged with nitrogen for 2 minutes, capped and heated at 110° C. for 16 hours (overnight). The mixture was cooled to room temperature and the solution was filtered. Direct purification of the filtrate using preparative RP-HPLC afforded Int 6b. (ESI-MS) m/z 481.19; $R_t$ 1.2 min (LC2)

Step C—Preparation of Compound 11 {8-(3-chloro-4-fluorobenzyl)-6-hydroxy-4-methylene-3,4,9,10-tetrahydropyrano[4',3':5,6]pyrido[1,2-a]pyrazine-5,7(1H,8H)-dione}

A solution of Int 6b (15 mg, 0.031 mmol) was stirred at room temperature in trifluoroacetic acid (1.0 ml) for 12 hours. The mixture was concentrated and the residue was purified using preparative RP-HPLC to afford Compound 11. (ESI-MS) m/z 391.06; $R_t$ 1.7 min (LC4)

The following compound of the present invention was made using the methods described in the Example above and substituting the appropriate reactants and/or reagents.

| Compd # | Structure | Starting Material | Parent ion m/z (ESI-MS) |
|---|---|---|---|
| 28 | 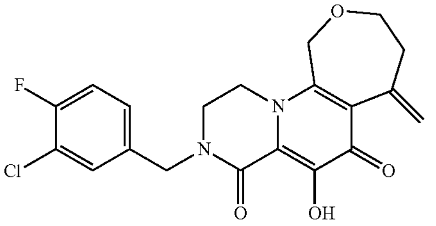 [SMILES: C=C1CCOCc2c1c(=O)c(O)c1n2CCN(Cc2ccc(F)c(Cl)c2)C1=O] | Int 1b | 405 |

Example 7

Preparation of Compound 12

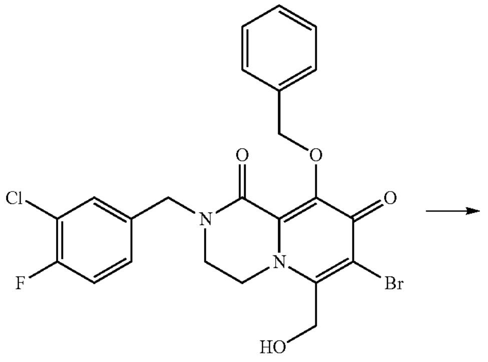

Int 1b

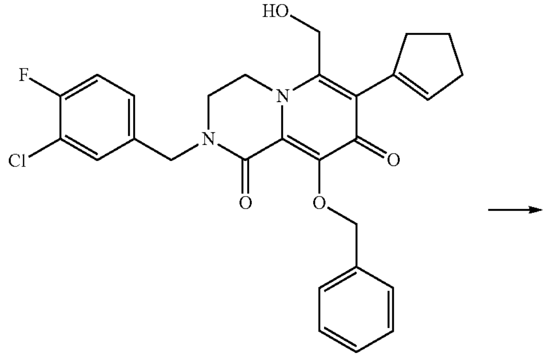

Int 7a

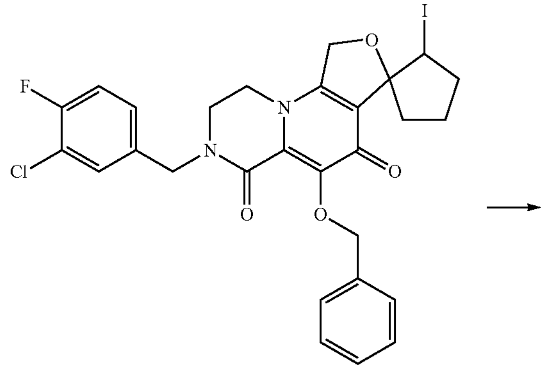

Int 7b

-continued

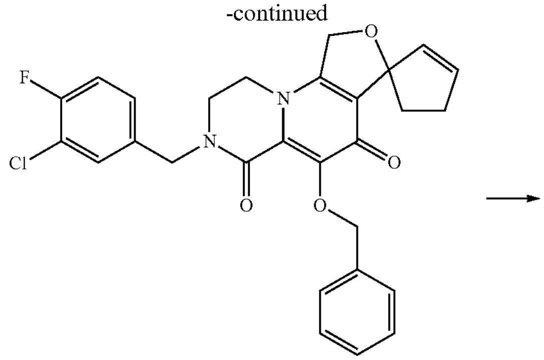

Int 7c

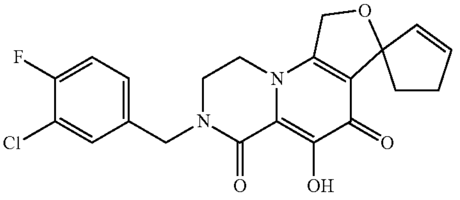

12

Step A—Preparation of Intermediate Compound Int 7a {9-(benzyloxy)-2-(3-chloro-4-fluorobenzyl)-7-(cyclopent-1-en-1-yl)-6-(hydroxymethyl)-3,4-dihydro-1H-pyrido[1,2-a]pyrazine-1,8(2H)-dione}

A solution of Int 1b (2000 mg, 3.83 mmol) and cyclopenten-1-ylboronic acid (1073 mg, 9.58 mmol) in acetonitrile (15 ml) and water (1.5 ml) was sub-surface sparged with nitrogen, and treated with $PdCl_2$(dppf)-dichloromethane adduct (157 mg, 0.192 mmol) and Hunig's Base (2.008 ml, 11.50 mmol). The resulting suspension was capped and heated at 100° C. for 4 hours. The resulting homogenous solution was cooled to room temperature and filtered. Purification by preparative RP-HPLC afforded Int 7a. (ESI-MS) m/z 509.18; $R_t$ 1.1 min (LC2)

Step B—Preparation of Intermediate Compound Int 7b {5'-(benzyloxy)-7'-(3-chloro-4-fluorobenzyl)-2-iodo-8',9'-dihydrospiro[cyclopentane-1,3'-furo[3',4':5,6]pyrido[1,2-a]pyrazine]-4',6'(1'H,7'H)-dione}

A solution of Int 7a (40 mg, 0.079 mmol) in acetonitrile (2.0 ml) was treated at room temperature with sodium carbonate (33.3 mg, 0.314 mmol) and iodine (19.95 mg, 0.079 mmol). The mixture was stirred at room temperature for 16 hours, treated with 2-methyl-1-butene (0.10 mL), stirred at room temperature for 30 minutes, and then filtered. Purification by preparative RP-HPLC afforded Int 7b. (ESI-MS) m/z 635.2; $R_t$ 1.2 min (LC2)

Step C—Preparation of Intermediate Compound Int 7c {5'-(benzyloxy)-7'-(3-chloro-4-fluorobenzyl)-8, 9'-dihydrospiro[cyclopent[2]ene-1,3'-furo[3',4':5,6] pyrido[1,2-a]pyrazine]-4',6'(1'H,7'H)-dione}

A solution of Int 7b (10 mg, 0.016 mmol) in DMF (0.5 ml) was treated at room temperature with DBU (0.024 ml, 0.158 mmol). The mixture was capped and heated at 90° C. for 20 hours, then cooled to room temperature. Glacial AcOH was added to neutralize the DBU. Direct purification by preparative RP-HPLC afforded Int 7c. (ESI-MS) m/z 507.21; $R_t$ 1.2 min (LC2)

Step D—Preparation of Compound 12 {7'-(3-chloro-4-fluorobenzyl)-5'-hydroxy-8',9'-dihydrospiro [cyclopent[2]ene-1,3'-furo[3',4':5,6]pyrido[1,2-a] pyrazine]-4',6'(1'H,7'H)-dione}

A solution of Int 7c (7.60 mg, 0.015 mmol) in trifluoroacetic acid (0.5 ml) was stirred at room temperature for 16 hours, then concentrated. Purification by preparative RP-HPLC afforded Compound 12. (ESI-MS) m/z 417.04; $R_t$ 1.7 min (LC4)

Example 8

Preparation of Compound 13

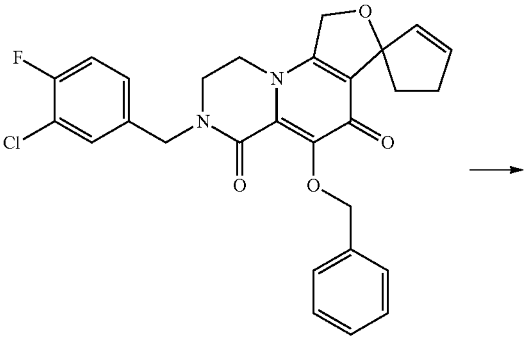

Int 7c

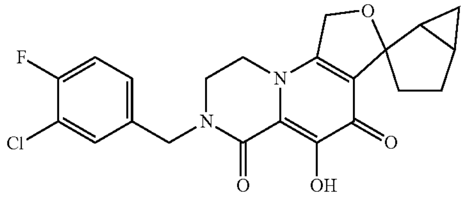

13

Compound 13—{7'-(3-chloro-4-fluorobenzyl)-5'-hydroxy-8',9'-dihydrospiro[bicyclo[3.1.0]hexane-2, 3'-furo[3',4': 5,6]pyrido[1,2-a]pyrazine]-4,6'(1'H, 7'H)-dione}

In a 1 dram vial with a teflon septa, a solution of Int 7c (15 mg, 0.030 mmol) in dichloromethane (1.0 ml) was cooled to 0° C. under nitrogen and treated with diiodomethane (0.012 ml, 0.148 mmol) and trifluoroacetic acid (0.011 ml, 0.148 mmol). The mixture was then treated dropwise with a solution of diethylzinc (1M in hexanes) (0.148 ml, 0.148 mmol). The mixture was stirred at room temperature for 12 hours. 2M aqueous $NaHSO_4$ (1 mL) was carefully added at room temperature. Brine (1 mL) was added and the mixture was vigorously agitated for 1 hour. The aqueous was removed and discarded. The organic was concentrated in vacuo. The residue was purified by preparative RP-HPLC to afford Compound 13. (ESI-MS) m/z 431.07; $R_t$ 1.7 min (LC4)

Example 9

Preparation of Compound 14

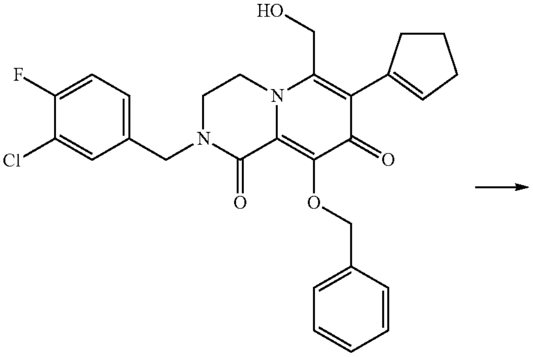

Int 7a

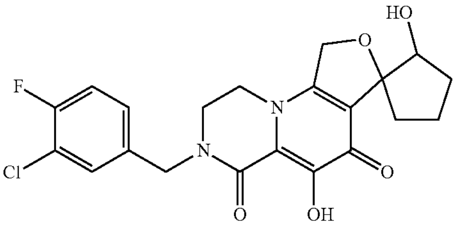

14

Compound 14-{7'-(3-chloro-4-fluorobenzyl)-2,5'-dihydroxy-8',9'-dihydrospiro[cyclopentane-1,3'-furo [3',4':5,6]pyrido[1,2-a]pyrazine]-4',6'(1'H,7'H)-dione}

Step 1:

A solution of Int 7a (145 mg, 0.285 mmol) in 2-propanol (2.0 ml) and water (0.2 ml) was treated with magnesium monoperoxyphthalate hexahydrate (282 mg, 0.570 mmol). The mixture was stirred at room temperature for 14 hours, and diluted with DMSO (2.0 mL). Purification by preparative RP-LC afforded 9-(benzyloxy)-7-(6-oxabicyclo[3.1.0] hexan-1-yl)-2-(3-chloro-4-fluorobenzyl)-6-(hydroxymethyl)-3,4-dihydro-1H-pyrido[1,2-a]pyrazine-1,8(2H)-dione.

Step 2:

A solution of the product from Step 1 (50 mg, 0.095 mmol) in dichloromethane (1.0 ml) was treated at room temperature with camphor sulfonic acid (25.0 mg, 0.108 mmol), capped and heated at 40° C. for 16 hours and then concentrated. The residue was dissolved in trifluoroacetic acid (1.0 mL) and stirred at room temperature for 16 hours.

The mixture was concentrated and the residue was purified using preparative RP-HPLC to afford Compound 14. (ESI-MS) m/z 435.11; $R_t$ 1.7 min (LC4)

Example 10

Preparation of Compound 15

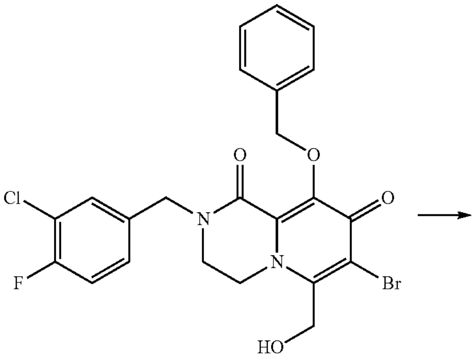

Int 1b

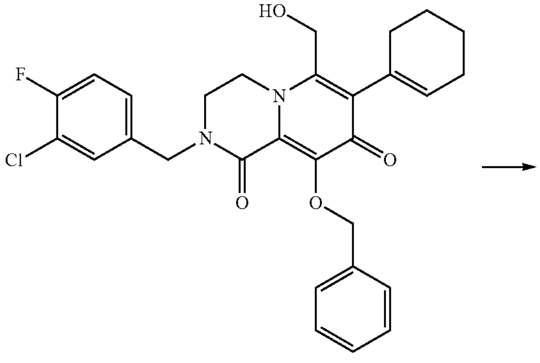

Int 10a

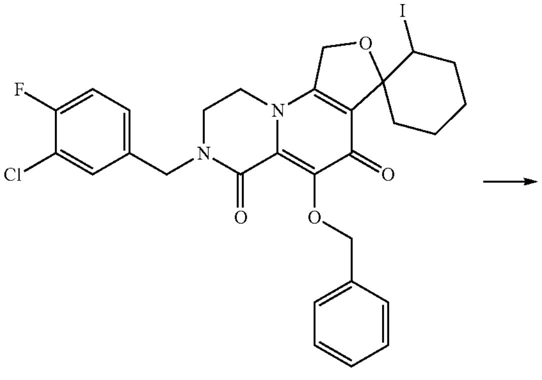

Int 10b

-continued

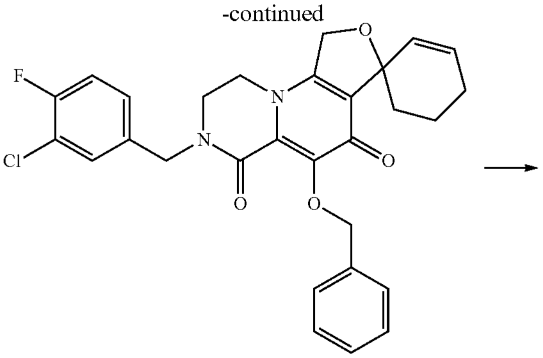

Int 10c

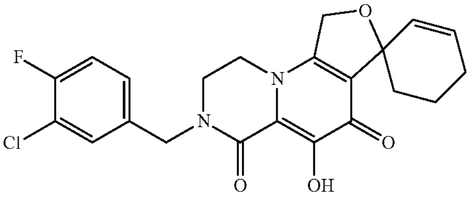

15

Step A—Preparation of Intermediate Compound Int 10a {9-(benzyloxy)-2-(3-chloro-4-fluorobenzyl)-7-(cyclohex-1-en-1-yl)-6-(hydroxymethyl)-3,4-dihydro-1H-pyrido[1,2-a]pyrazine-1,8(2H)-dione}

A solution of Int 1b (500 mg, 0.958 mmol) and 1-cyclohexen-1-yl-boronic acid (362 mg, 2.87 mmol) in acetonitrile (6 ml) and water (0.2 ml) was sub-surface sparged with nitrogen, treated with $PdCl_2$(dppf)-DichloromethaneAdduct (39.1 mg, 0.048 mmol) and Hunig's Base (0.669 ml, 3.83 mmol). Sparging continued for 2 minutes, then the vial was capped and heated at 95° C. for 4 hours. The mixture was then cooled to room temperature. Purification by preparative RP-LC afforded Int 10a. (ESI-MS) m/z 523.02; $R_t$ 1.8 min (LC4)

Step B—Preparation of Int 10b {5'-(benzyloxy)-7'-(3-chloro-4-fluorobenzyl)-2-iodo-8',9'-dihydrospiro[cyclohexane-1,3'-furo[3',4':5,6]pyrido[1,2-a]pyrazine]-4',6'(1'H,7'H)-dione}

A solution of Int 10a (100 mg, 0.191 mmol) in acetonitrile (2.0 ml) was treated with sodium carbonate (81 mg, 0.765 mmol) and iodine (72.8 mg, 0.287 mmol). The mixture was stirred at room temperature for 12 hours and then treated with 2-methyl-2-butene (0.05 mL). The mixture was filtered and the filtrate was concentrated. The residue was purified using preparative RP-HPLC to afford Int 10b. (ESI-MS) m/z 649.20; $R_t$ 1.24 min (LC2).

Step C—Preparation of Intermediate Compound Int 10c {5'-(benzyloxy)-7'-(3-chloro-4-fluorobenzyl)-8',9'-dihydrospiro[cyclohex[2]ene-1,3'-furo[3',4':5,6]pyrido[1,2-a]pyrazine]-4',6'(1'H,7'H)-dione}

A solution of Int 10b (18 mg, 0.028 mmol) in N,N-Dimethylformamide (0.5 ml) was treated with DBU (0.042 ml, 0.277 mmol) and heated at 95° C. for 24 hours. The mixture was cooled to room temperature, neutralized with glacial AcOH (0.1 mL), and purified using preparative RP-HPLC (Akzo-Nobel Kromasil 100-5C18 column {21.2 mm×10 cm}, 10% to 75% MeCN/water+0.05% trifluoroacetic acid over 10 min, 25 mL/min, UV 254 nM). The fractions were lyophilized to afford Int 10c. (ESI-MS) m/z 521.23; $R_t$ 2.1 min (LC4)

Step D—Preparation of Compound 15 {7'-(3-chloro-4-fluorobenzyl)-5'-hydroxy-8',9'-dihydrospiro[cyclohex[2]ene-1,3'-furo[3',4':5,6]pyrido[1,2-a]pyrazine]-4',6'(1'H,7'H)-dione}

A solution of Int 10c (6 mg, 0.012 mmol) in trifluoroacetic acid (1.0 ml) was stirred at room temperature for 12 hours, and then concentrated. The residue was dissolved in 5% aqueous DMSO and purified using preparative RP-HPLC to afford Compound 15. (ESI-MS) m/z 431.12; $R_t$ 1.8 min (LC4)

Example 11

Preparation of Compound 16

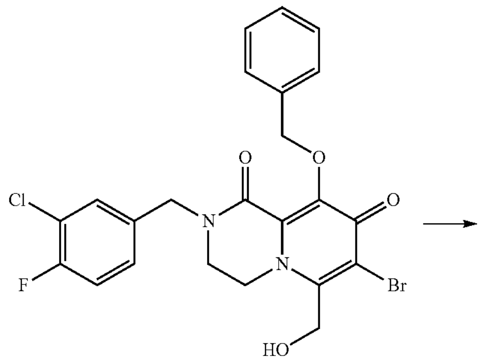

Int 1b

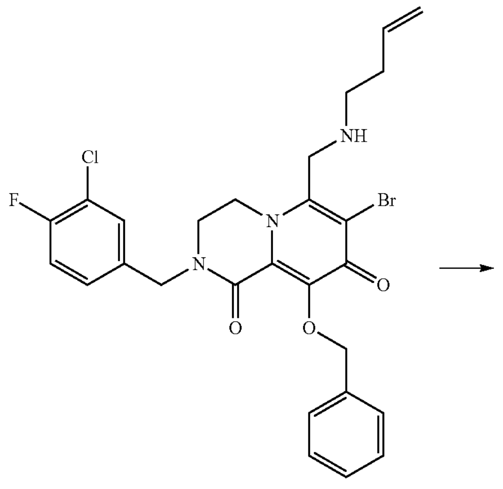

Int 11a

-continued

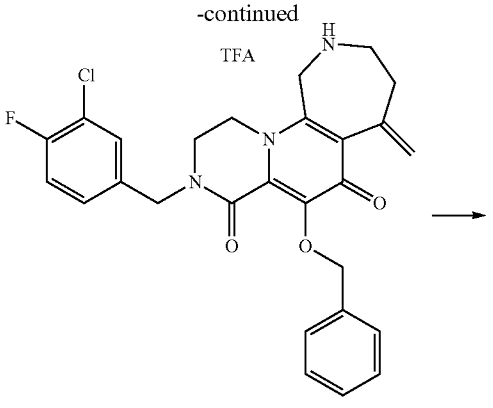

Int 11b

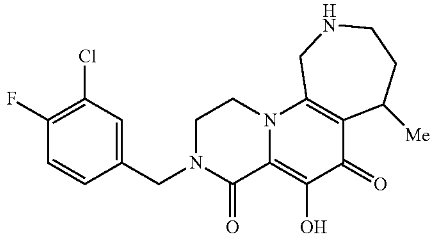

16

Step A—Preparation of Intermediate Compound Int 11a {9-(benzyloxy)-7-bromo-6-((but-3-en-1-ylamino)methyl)-2-(3-chloro-4-fluorobenzyl)-3,4-dihydro-1H-pyrido[1,2-a]pyrazine-1,8(2H)-dione trifluoroacetate salt}

A solution of Int 1b (1000 mg, 1.92 mmol) in dichloromethane (10.0 ml) was treated at room temperature with 2,4,6-trimethylpyridine (1.016 ml, 7.67 mmol) and thionyl chloride (0.280 ml, 3.83 mmol). The mixture was stirred at room temperature for 4 hours and concentrated. The residue was dissolved in DMF (10 mL) and treated with potassium carbonate (1060 mg, 7.67 mmol) and but-3-en-1-amine (545 mg, 7.67 mmol). The mixture was heated at 80° C. for 1 hour and then cooled to room temperature and allowed to stir for 14 hours. The solution was filtered through a pad of celite and the filtrate was treated with glacial AcOH (0.5 mL). Purification by preparative RP-HPLC afforded Int 11a. (ESI-MS) m/z 574.18, 576.16; $R_t$ 1.1 min (LC2)

Step B—Preparation of Intermediate Compound Int 11b {7-(benzyloxy)-9-(3-chloro-4-fluorobenzyl)-5-methylene-2,3,4,5,10,11-hexahydropyrazino[1,2':1,6]pyrido[2,3-c]azepine-6,8(1H,9H)-dione trifluoroacetate salt}

A solution of Int 11a (332 mg, 0.578 mmol) in N,N-dimethylacetamide (4.0 ml) was sub-surface sparged with nitrogen gas, and treated with $Pd(Ph_3P)_4$ (66.7 mg, 0.058 mmol) and triethylamine (0.402 ml, 2.89 mmol). The vial was capped and heated at 100° C. for 16 hours, cooled to room temperature and filtered. The filtrate was neutralized with glacial AcOH (0.5 mL) and purified using preparative RP-HPLC to afford Int 11b. (ESI-MS) m/z 494.18; $R_t$ 1.1 min (LC2).

Step C—Preparation of Compound 16 {9-(3-chloro-4-fluorobenzyl)-7-hydroxy-5-methyl-2,3,4,5,10,11-hexahydropyrazino[1',2':1,6]pyrido[2,3-c]azepine-6,8(1H,9H)-dione trifluoroacetate salt}

A mixture of Int 11b (100 mg, 0.164 mmol) in ethanol was treated at room temperature with platinum (IV) oxide (7.5 mg, 0.2 equiv) and stirred at room temperature under hydrogen (1 atm) for 36 hours. The mixture was filtered and the filtrate was concentrated in vacuo. The residue was purified using preparative RP-HPLC to afford Compound 16. (ESI-MS) m/z 406.13; $R_t$ 1.3 min (LC4).

Example 12

Preparation of Compounds 17 and 18

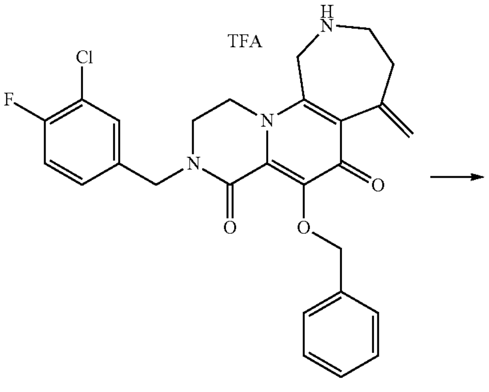

Int 11b

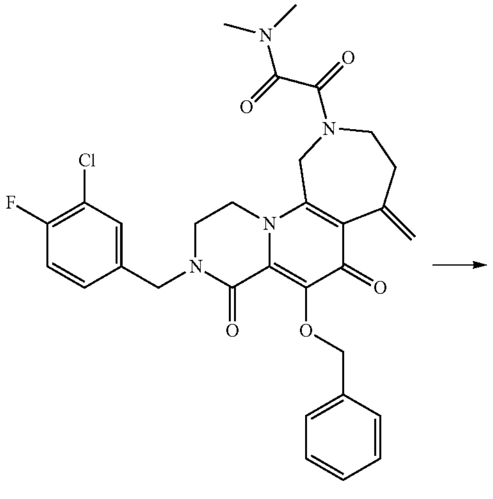

Int 12a

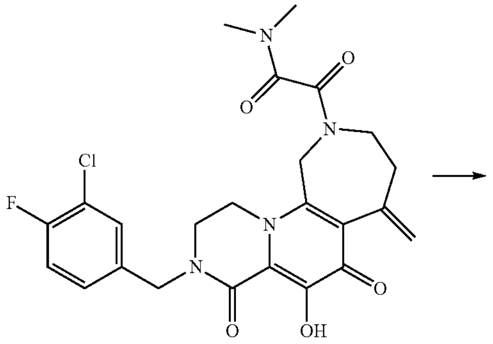

17

-continued

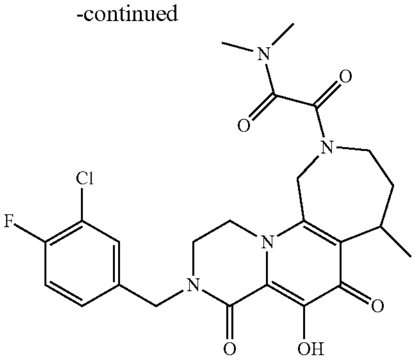

18

Step A—Preparation of Intermediate Compound Int 12a {2-(7-(benzyloxy)-9-(3-chloro-4-fluorobenzyl)-5-methylene-6,8-dioxo-4, 5,8,9,10,11-hexahydropyrazino[1',2':1,6]pyrido[2,3-c]azepin-2 (1H,3H,6H)-yl)-N,N-dimethyl-2-oxoacetamide}

A solution of Int 11b (50 mg, 0.082 mmol) and N,N-dimethyloxamic acid (19.26 mg, 0.164 mmol) in DMF (1.0 ml) was treated at room temperature with HATU (62.5 mg, 0.164 mmol) and N-methylmorpholine (0.036 ml, 0.329 mmol). The mixture was stirred at room temperature for 16 hours, treated with glacial AcOH (0.05 ml) and purified using preparative RP-HPLC to afford Int 12a. (ESI-MS) m/z 593.24; $R_t$ 1.8 min (LC4)

Step B—Preparation of Compound 17 {2-(9-(3-chloro-4-fluorobenzyl)-7-hydroxy-5-methylene-6,8-dioxo-4, 5,8,9,10,11-hexahydropyrazino[1',2':1,6]pyrido[2,3-c]azepin-2(1H,3H,6H)-yl)-N,N-dimethyl-2-oxoacetamide}

A solution of Int 12a (48 mg, 0.081 mmol) was stirred with trifluoroacetic acid (0.5 ml) for 24 hours. The mixture was concentrated and the residue was purified using preparative RP-HPLC to afford Compound 17. (ESI-MS) m/z 503.17; $R_t$ 1.5 min (LC4)

Step C—Preparation of Compound 18 {2-(9-(3-chloro-4-fluorobenzyl)-7-hydroxy-5-methyl-6,8-dioxo-4, 5,8,9,10,11-hexahydropyrazino[1',2':1,6]pyrido[2,3-c]azepin-2(1H,3H,6H)-yl)-N,N-dimethyl-2-oxoacetamide}

Compound 17 (18.1 mg, 0.036 mmol) and Pd/C (dry powder, Strem) (8.0 mg, 7.52 μmol) in 1 dram vial were flushed with hydrogen and stirred at room temperature under hydrogen (1 atm) for 24 hours. The mixture was filtered and the filtrate was concentrated in vacuo. The residue was purified using preparative RP-HPLC to afford Compound 18. (ESI-MS) m/z 505.14; $R_t$ 1.6 min (LC4)

The following compounds of the present invention were made using the methods described in Example 12 above and substituting the appropriate reactants and/or reagents.

| Compd # | Structure | Starting Material | Parent ion m/z (ESI-MS) |
|---|---|---|---|
| 29 | 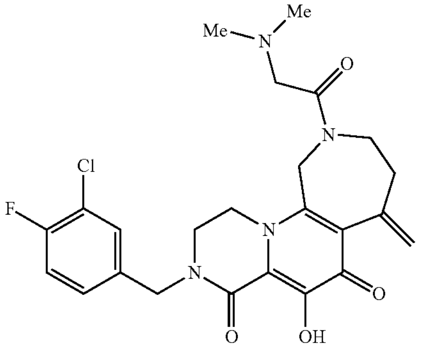 [SMILES: C=C1CCN(C(=O)CN(C)C)Cc2c1c(=O)c(O)c1n2CCN(Cc2ccc(F)c(Cl)c2)C1=O] | Int 11b | 489 |
| 30 | 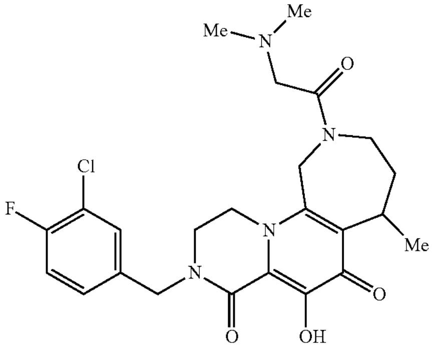 [SMILES: CC1CCN(C(=O)CN(C)C)Cc2c1c(=O)c(O)c1n2CCN(Cc2ccc(F)c(Cl)c2)C1=O] | Int 11b | 491 |
Example 13
Preparation of Compound 19
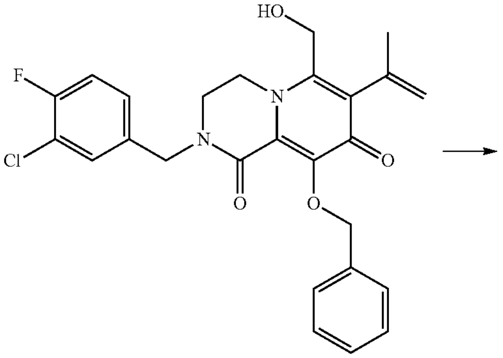
Int 2a
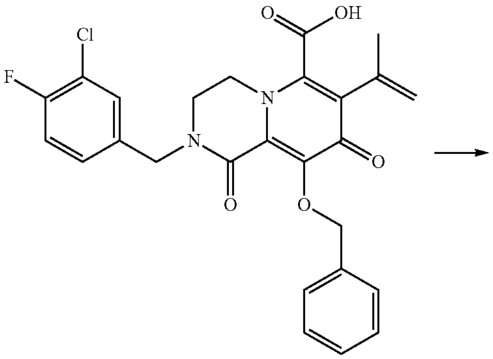
Int 13a
-continued
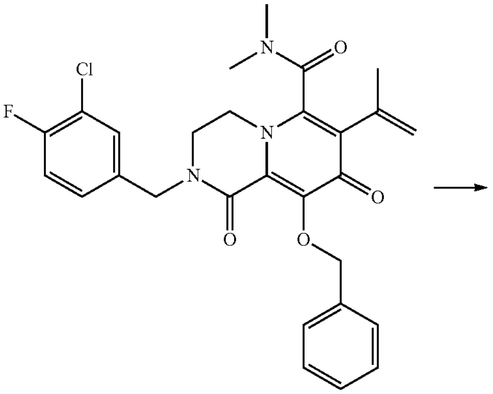
Int 13b
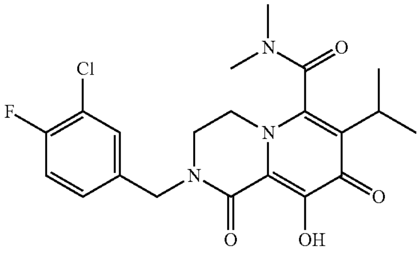
19

Step A—Preparation of Intermediate Compound Int 13a {9-(benzyloxy)-2-(3-chloro-4-fluorobenzyl)-1,8-dioxo-7-(prop-1-en-2-yl)-2,3,4,8-tetrahydro-1H-pyrido[1,2-a]pyrazine-6-carboxylic acid}

Step 1:

To a solution of Int 2a (100 mg, 0.207 mmol) and triethylamine (0.173 mL, 1.242 mmol) in $CHCl_3$ (5 mL) and DMSO (5 mL) was added pyridine sulfur trioxide complex (1.65 mg, 1.035 mmol) at 0° C. The reaction mixture was stirred and warmed gradually to room temperature over 6 hours. The reaction solution was washed with water (100 mL) and extracted with dichloromethane (100 mL×3). The combined organic layer was washed with water (3×50 mL) and brine (50 mL). The organic layer was dried over anhydrous $Na_2SO_4$. After filtration and concentration, the crude 9-(benzyloxy)-2-(3-chloro-4-fluorobenzyl)-1,8-dioxo-7-(prop-1-en-2-yl)-2,3,4,8-tetrahydro-1H-pyrido[1,2-a]pyrazine-6-carbaldehyde was used without further purification. (ESI-MS) m/z 499.12 (Mass+18); $R_t$ 1.70 min (LC4).

Step 2:

To a solution of the product from Step 1 (100 mg, 0.207 mmol) in Acetone (5 mL) was added Sulfamic Acid (56.3 mg, 0.580 mmol). Sodium Chlorite (41.2 mg, 0.456 mmol) in water (5 mL) was added to the reaction solution at room temperature and stirred for 6 hours. After removing acetone, the reaction mixture was filtered and the filter cake was washed with water (3×10 mL) and air-dried to afford Int 13a (ESI-MS) m/z 497.05; $R_t$ 1.67 min (LC4).

Step B—Preparation of Intermediate Compound Int 13b {9-(benzyloxy)-2-(3-chloro-4-fluorobenzyl)-N,N-dimethyl-1,8-dioxo-7-(prop-1-en-2-yl)-2,3,4,8-tetrahydro-1H-pyrido[1,2-a]pyrazine-6-carboxamide}

To a solution of Int 13a (355.2 mg, 0.715 mmol) and DIPEA (0.562 mL, 3.22 mmol) in dichloromethane (13 mL) at 0° C. was added BOP-Cl (728 mg, 2.86 mmol) with stirring. The reaction mixture was stirred at 0° C. for 1 hour. Dimethylamine hydrochloride (236 mg, 2.86 mmol) was added to the reaction mixture and gradually warmed to room temperature with stirring overnight. After concentration, the residue was purified using preparative RP-HPLC to afford Int 13b. (ESI-MS) m/z 524.13; $R_t$ 1.82 min (LC4).

Step C—Preparation of Compound 19 {2-(3-chloro-4-fluorobenzyl)-9-hydroxy-7-isopropyl-N,N-dimethyl-1,8-dioxo-2,3,4,8-tetrahydro-1H-pyrido[1,2-a]pyrazine-6-carboxamide}

To a solution of Int 13b (94 mg, 0.217 mmol) in ethyl acetate (5 mL) was added platinum (II) oxide (4.57 mg, 0.022 mmol). The reaction mixture was bubbled with nitrogen for 3 minutes. Hydrogen was introduced to the reaction with a balloon. The reaction was stirred overnight. After filtration and concentration of the filtrate, the residue was purified using preparative RP-HPLC. Fractions were lyophilized to afford Compound 19. (ESI-MS) m/z 436.09; $R_t$ 1.59 min (LC4).

Example 14

Preparation of Compound 20

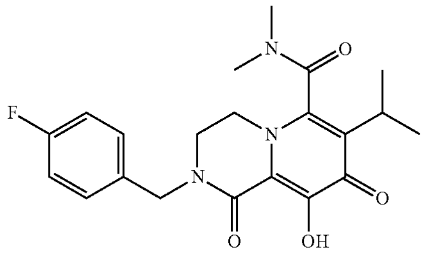

Compound 20—{2-(4-fluorobenzyl)-9-hydroxy-7-isopropyl-N,N-dimethyl-1,8-dioxo-2,3,4,8-tetrahydro-1H-pyrido[1,2-a]pyrazine-6-carboxamide}

To a solution Int 13b (94 mg, 0.217 mmol) in methanol (2 mL) was added 5% Pd/C (20 mg, 9.4 umol). The reaction mixture was bubbled with nitrogen for 3 minutes. Hydrogen was introduced to the reaction with a balloon. The reaction was stirred overnight. After filtration and concentration, the residue was purified using preparative RP-HPLC to afford Compound 20. (ESI-MS) m/z 402.08; $R_t$ 1.41 min (LC4).

Example 15

Preparation of Compounds 21 and 22

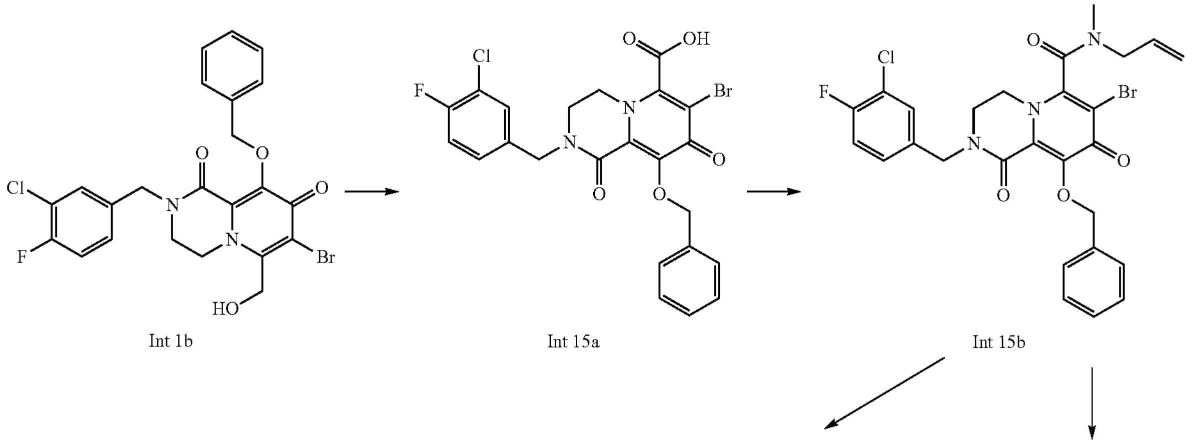

Int 1b

Int 15a

Int 15b

-continued

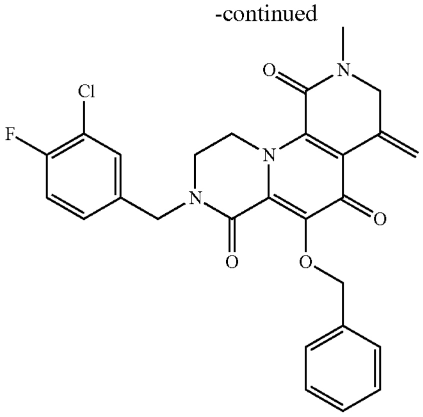

Int 15c

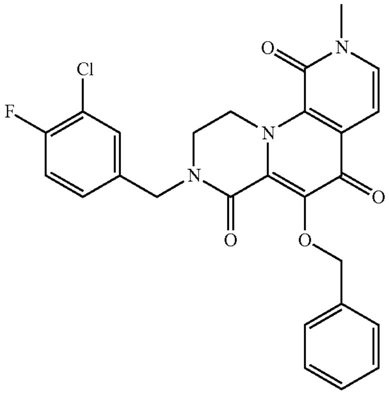

Int 15d

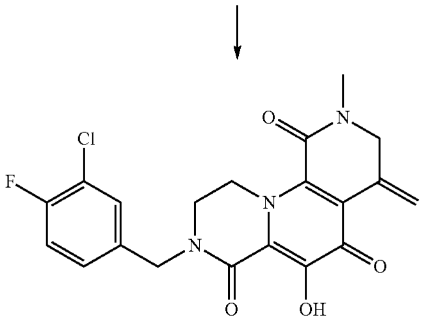

21

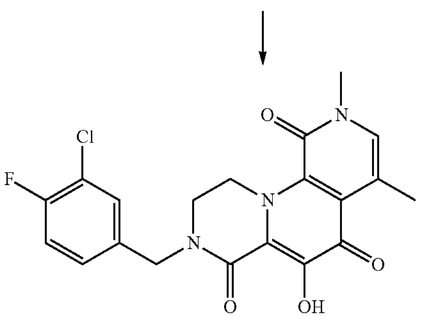

22

Step A—Preparation of Intermediate Compound Int 15a {9-(benzyloxy)-7-bromo-2-(3-chloro-4-fluorobenzyl)-1,8-dioxo-2,3,4,8-tetrahydro-1H-pyrido[1,2-a]pyrazine-6-carboxylic acid}

Step 1:

To a solution of Int 1b (100 mg, 0.192 mmol) and triethylamine (0.160 mL, 1.150 mmol) in $CHCl_3$ (1 mL) and DMSO (1.000 mL) was added pyridine sulfur trioxide (153 mg, 0.958 mmol) at 0° C. The reaction mixture was warmed slowly to room temperature and stirred for 4 hours. The mixture was washed with brine and water. The organic layer was dried over $Na_2SO_4$. After drying under reduced pressure, the crude 9-(benzyloxy)-7-bromo-2-(3-chloro-4-fluorobenzyl)-1,8-dioxo-2,3,4,8-tetrahydro-1H-pyrido[1,2-a]pyrazine-6-carbaldehyde, was directly used without further purification.

Step 2:

The product from Step 1 (100 mg) was stirred with sulfamic acid (26.1 mg, 0.268 mmol) and sodium chlorite (19.07 mg, 0.211 mmol) in Acetone (1.000 mL) and water (1.000 mL) at room temperature for 45 minutes. The acetone was removed under reduced pressure. The residue was purified using preparative RP-HPLC to afford Int 15a. (ESI-MS) m/z 536.93, 538.91; $R_t$ 1.8 min (LC4)

Step B—Preparation of Intermediate Compound Int 15b {N-allyl-9-(benzyloxy)-7-bromo-2-(3-chloro-4-fluorobenzyl)-N-methyl-1,8-dioxo-2,3,4,8-tetrahydro-1H-pyrido[1,2-a]pyrazine-6-carboxamide}

To a solution of Int 15a (84 mg, 0.157 mmol), N-methylprop-2-en-1-amine (0.018 mL, 0.188 mmol) and triethylamine (0.044 mL, 0.314 mmol) in dichloromethane (1 mL) was added BOP-Cl (47.9 mg, 0.188 mmol). The reaction mixture was stirred at room temperature overnight. After concentration, the residue was purified using preparative RP-HPLC to afford Int 15b. (ESI-MS) m/z 589.96; $R_t$ 2.14 min (LC4).

Step C—Preparation of Intermediate Compound Int 15c {6-(benzyloxy)-8-(3-chloro-4-fluorobenzyl)-2-methyl-4-methylene-3,4,9,10-tetrahydro-1H-pyrazino[1,2-a][1,7]naphthyridine-1,5,7(2H,8H)-trione} and Intermediate Compound Int 15d {6-(benzyloxy)-8-(3-chloro-4-fluorobenzyl)-2,4-dimethyl-9,10-dihydro-1H-pyrazino[1,2-a][1,7]naphthyridine-1,5,7(2H,8H)-trione}

A solution of Int 15b (74 mg, 0.126 mmol), $Pd(OAc)_2$ (2.82 mg, 0.013 mmol) and tri-o-tolylphosphine (7.65 mg, 0.025 mmol) in triethylamine (5 mL) was heated at 120° C. for 1.5 hours. DMA (1 mL) was added to improve the solubility of the reactants. After filtration and concentration, the residue was purified using preparative RP-HPLC to afford Int 15c (ESI-MS) m/z 417.99; $R_t$ 1.68 min (LC4) and Int 15d (ESI-MS) m/z 417.99; $R_t$ 1.77 min (LC4).

Step D—Preparation of Compound 21 {8-(3-chloro-4-fluorobenzyl)-6-hydroxy-2-methyl-4-methylene-3,4,9,10-tetrahydro-1H-pyrazino[1,2-a][1,7]naphthyridine-1,5,7(2H,8H)-trione}

To a solution of Int 15c (10 mg, 0.020 mmol) in dichloromethane (1 ml) was added trifluoroacetic acid (200 μl, 2.60 mmol) and stirred for 1 hour. The reaction mixture was concentrated. The residue was purified using preparative RP-HPLC to afford Compound 21. (ESI-MS) m/z 418.0; $R_t$ 1.68 min (LC4).

Step E—Preparation of Compound 22 {8-(3-chloro-4-fluorobenzyl)-6-hydroxy-2,4-dimethyl-9,10-dihydro-1H-pyrazino[1,2-a][1,7]naphthyridine-1,5,7(2H,8H)-trione}

To a solution of Int 15d (10 mg, 0.020 mmol) in dichloromethane (1 ml) was added trifluoroacetic acid (200 μl, 2.60 mmol) and stirred for 1 hour. The reaction mixture was concentrated. The residue was purified using preparative RP-HPLC to afford Compound 22. (ESI-MS) m/z 418.0; $R_t$ 1.77 min (LC4).

Example 16

Preparation of Compound 23

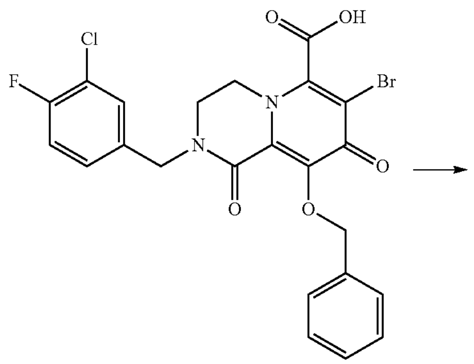

Int 15a

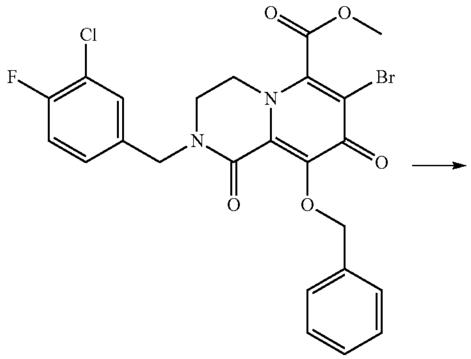

Int 16a

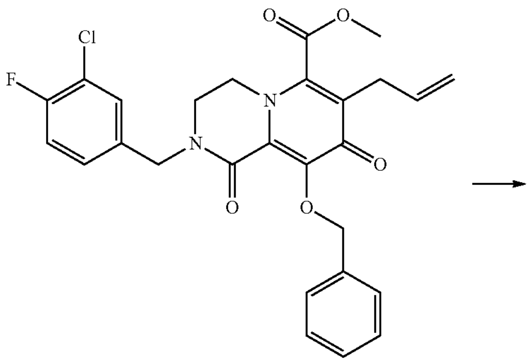

Int 16b

-continued

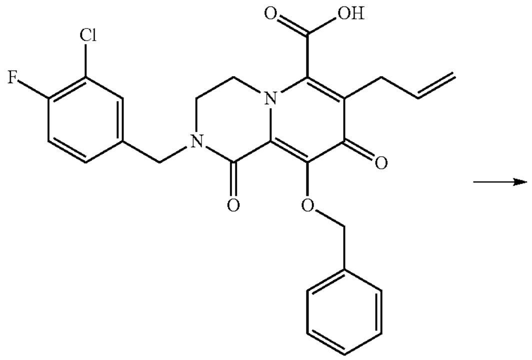

Int 16c

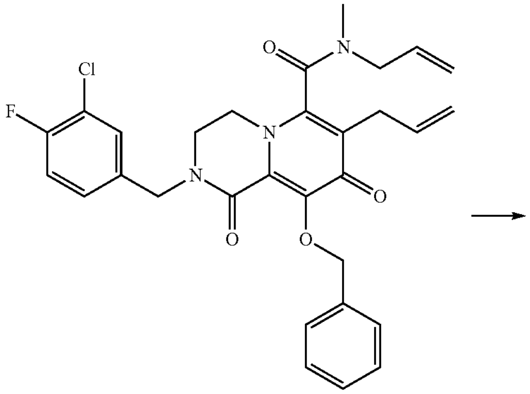

Int 16d

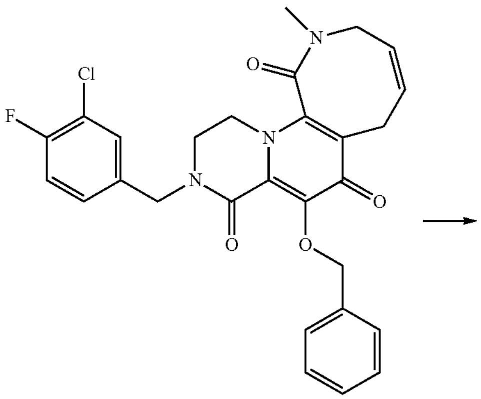

Int 16e

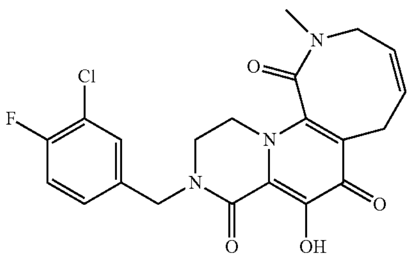

23

Step A—Preparation of Intermediate Compound Int 16a {9-(benzyloxy)-7-bromo-2-(3-chloro-4-fluorobenzyl)-1,8-dioxo-2,3,4,8-tetrahydro-1H-pyrido[1,2-a]pyrazine-6-carboxylate}

A suspension of Int 15a (2.35 g, 4.39 mmol) in toluene (50 mL) and methanol (5 mL) was cooled to 0° C. and treated with trimethylsilyl diazomethane in hexane (10.97 ml, 2M, 21.93 mmol). The reaction was warmed to room temperature and stirred for 30 minutes. The mixture was treated with glacial acetic acid (1 mL) and concentrated to afford Int 16a. (ESI-MS) m/z 549.03; $R_t$ 2.01 min (LC4).

Step B—Preparation of Intermediate Compound Int 16b {methyl 7-allyl-9-(benzyloxy)-2-(3-chloro-4-fluorobenzyl)-1,8-dioxo-2,3,4,8-tetrahydro-1H-pyrido[1,2-a]pyrazine-6-carboxylate}

A mixture of Int 16a (24 mg, 0.044 mmol), allyl tri-n-butylstannane (27.1 μL, 0.087) and $Pd(Ph_3P)_4$ (5.04 mg, 4.37 μmol) in dioxane (500 μL) was heated at 120° C. under nitrogen for 16 hours. The mixture was cooled to room temperature and filtered. The filtrate was concentrated and the residue was purified using preparative RP-HPLC to afford Int 16b. (ESI-MS) m/z 511.18; $R_t$ 1.91 min (LC4).

Step C—Preparation of Intermediate Compound Int 16c {7-allyl-9-(benzyloxy)-2-(3-chloro-4-fluorobenzyl)-1,8-dioxo-2,3,4,8-tetrahydro-1H-pyrido[1,2-a]pyrazine-6-carboxylic acid}

To a solution of Int 16b (25 mg, 0.049 mmol) in methanol (100 μL) and THF (100 μL) was added aqueous LiOH (500 μL, 2M, 1 mmol). The reaction was warmed to 60° C. for 2 hours. The reaction mixture was cooled to room temperature and quenched with aqueous HCl (2M, 1 mL). After concentration, the residue was purified using preparative RP-HPLC to afford Int 16c. (ESI-MS) m/z 497.23; $R_t$ 1.60 min (LC4).

Step D—Preparation of Intermediate Compound Int 16d {N,7-diallyl-9-(benzyloxy)-2-(3-chloro-4-fluorobenzyl)-N-methyl-1,8-dioxo-2,3,4,8-tetrahydro-1H-pyrido[1,2-a]pyrazine-6-carboxamide}

To a solution of Int 16c (24.31 mg, 0.049 mmol) and N-Allylmethylamine (0.022 mL, 0.220 mmol) in dichloromethane (1 mL) at 0° C. was added BOP-Cl (18.68, 0.073 mmol). The reaction was warmed to room temperature and stirred for 3 hours. After concentration, the residue was purified using preparative RP-HPLC to afford Int 16d. (ESI-MS) m/z 550.22; $R_t$ 1.88 min (LC4).

Step E—Preparation of Intermediate Compound Int 16e {(Z)-8-(benzyloxy)-10-(3-chloro-4-fluorobenzyl)-2-methyl-2,3,11,12-tetrahydro-1H-pyrazino[1',2':1,6]pyrido[2,3-c]azocine-1,7,9(6H,10H)-trione}

A solution of Int 16d (5 mg, 9.09 μmmol) in anhydrous dichloromethane (1 mL) was sub-surface sparged with nitrogen for 2 minutes. Zhan catalyst PLC-301 (2 mg) was added to the solution. The reaction vial was capped and warmed to 50° C. with stirring for 2 hours. After concentration, the residue was purified using preparative RP-HPLC to afford Int 16e. (ESI-MS) m/z 522.08; $R_t$ 1.84 min (LC4).

Step F—Preparation of Compound 23 {(Z)-10-(3-chloro-4-fluorobenzyl)-8-hydroxy-2-methyl-2,3,11,12-tetrahydro-1H-pyrazino[1',2':1,6]pyrido[2, 3-c]azocine-1,7,9(6H,10H)-trione}

To a solution of Int 16e (3 mg, 5.75 μmol) in dichloromethane (1 ml) was added trifluoroacetic acid (20 μL, 0.260 mmol) and the mixture was stirred at room temperature for 2 hours. After concentration, the residue was purified using preparative RP-HPLC to afford Compound 23. (ESI-MS) m/z 431.99; $R_t$ 1.58 min (LC4).

Example 17

Preparation of Compound 24

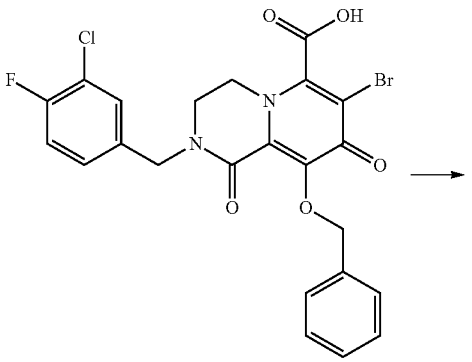

Int 15a

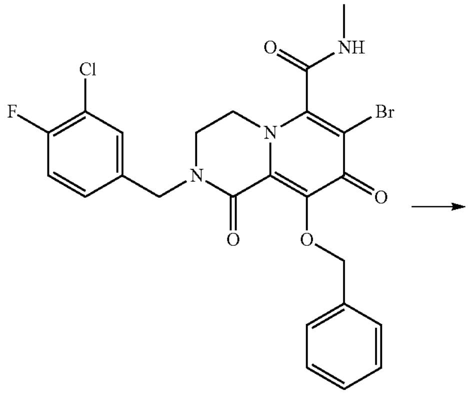

Int 17a

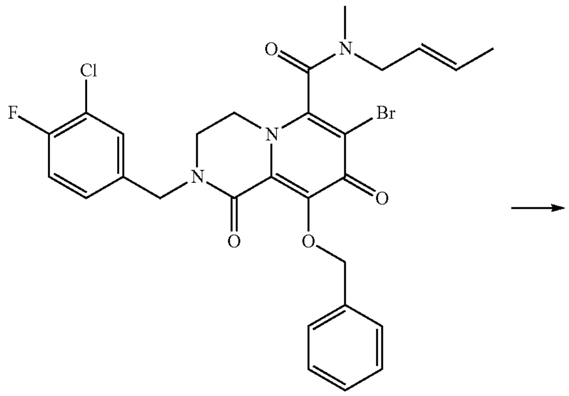

Int 17b

-continued

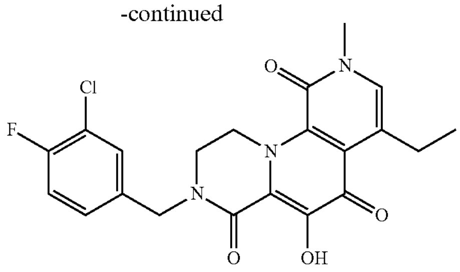

24

Step A—Preparation of Intermediate Compound Int 17a {9-(benzyloxy)-7-bromo-2-(3-chloro-4-fluorobenzyl)-N-methyl-1,8-dioxo-2,3,4,8-tetrahydro-1H-pyrido[1,2-a]pyrazine-6-carboxamide}

To a solution of Int 15a (50 mg, 0.093 mmol), HOBT (21.44 mg, 0.140 mmol) and methylamine hydrochloride (9.45 mg, 0.140 mmol) and DIPEA (0.073 mL, 0.420 mmol) in dichloromethane (1 mL) was added EDCI (26.8 mg, 0.140 mmol). The reaction mixture was stirred at room temperature overnight. After concentration, the residue was purified using preparative RP-HPLC to afford Int 17a. (ESI-MS) m/z 548.13; $R_t$ 1.70 min (LC4).

Step B—Preparation of Intermediate Compound Int 17b {(E)-9-(benzyloxy)-7-bromo-N-(but-2-en-1-yl)-2-(3-chloro-4-fluorobenzyl)-N-methyl-1,8-dioxo-2,3,4,8-tetrahydro-1H-pyrido[1,2-a]pyrazine-6-carboxamide}

A solution of Int 17a (40 mg, 0.073 mmol) and cesium carbonate (95 mg, 0.292 mmol) was stirred in DMF (1 mL) for 5 minutes. Crotyl bromide (23.15 mg, 0.146 mmol) was added to the reaction solution and stirred at 50° C. for 3 hours. The reaction mixture was neutralized with aqueous HCl (2M, 5 mL) and extracted with ethyl acetate. The combined organic layer was washed with water and concentrated. The residue was purified using preparative RP-HPLC to afford Int 17b. (ESI-MS) m/z 602.08; $R_t$ 2.06 min (LC4).

Step C—Preparation of Compound 24 {8-(3-chloro-4-fluorobenzyl)-4-ethyl-6-hydroxy-2-methyl-9,10-dihydro-1H-pyrazino[1,2-a][1,7]naphthyridine-1,5,7(2H,8H)-trione}

A solution of Int 17b (50 mg, 0.083 mmol), $Pd(Ph_3P)_4$ (47.9 mg, 0.041 mmol) and triethylamine (0.116 mL, 0.829 mmol) in DMA (1 mL) was sub-surface sparged with nitrogen for 2 minutes. The reaction mixture was warmed to 135° C. for 2 hours. After filtration and concentration, the residue was purified using preparative RP-HPLC to afford Compound 24. (ESI-MS) m/z 432.01; $R_t$ 1.90 min (LC4).

Example 18

Preparation of Compounds 31 and 32

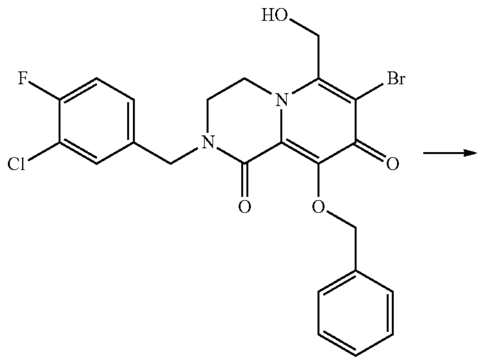

Int 1b

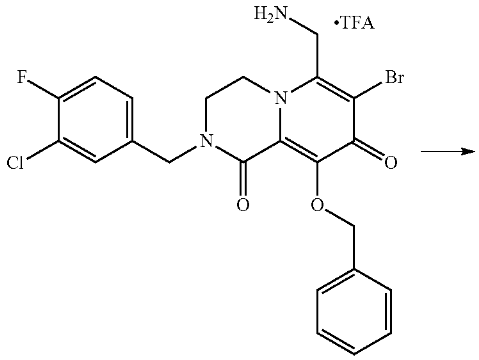

Int 18a

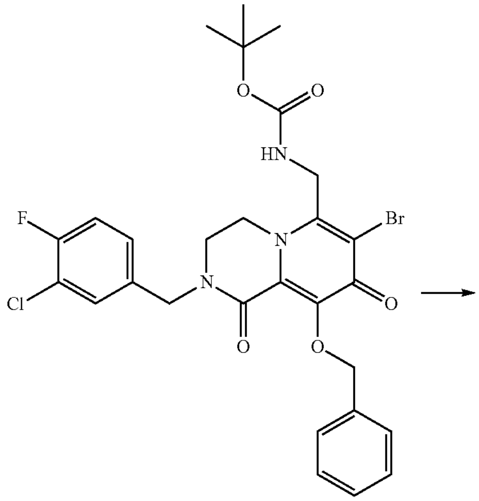

Int 18b

-continued

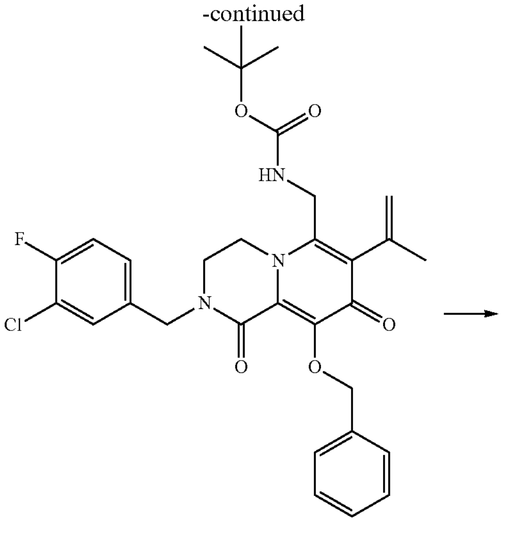

Int 18c

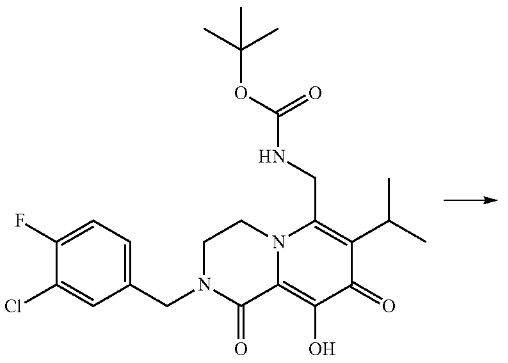

31

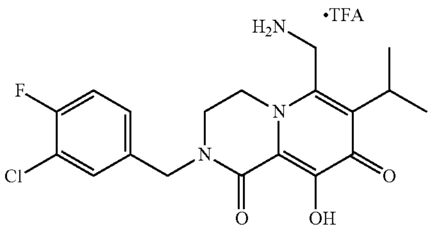

32

Step A—Preparation of Intermediate Compound Int 18a {6-(aminomethyl)-9-(benzyloxy)-7-bromo-2-(3-chloro-4-fluorobenzyl)-3,4-dihydro-1H-pyrido[1,2-a]pyrazine-1,8(2H)-dione trifluoroacetate salt}

A solution of Int 1b (200 mg, 0.383 mmol) in dichloromethane (4.0 ml) was treated at room temperature with 2,4,6-trimethylpyridine (0.152 ml, 1.150 mmol) and thionyl chloride (0.056 ml, 0.767 mmol). The mixture was stirred at room temperature for 12 hours then concentrated. The dark brown residue was dissolved with 2-propanol (4.0 mL) and treated with 30% aqueous $NH_4OH$ (2.0 mL). The mixture was heated at 50° C. for 3 hours, then cooled to room temperature. Most of the 2-propanol was removed in vacuo and the resulting solution was neutralized with glacial AcOH and diluted with 1:1 acetonitrile/water. Purification using preparative mass-guided RP-HPLC afforded Int 18a. (ESI-MS) m/z 519.97, 521.93; Rt 1.05 min (LC2).

Step B—Preparation of Intermediate Compound Int 18b {tert-butyl((9-(benzyloxy)-7-bromo-2-(3-chloro-4-fluorobenzyl)-1,8-dioxo-2,3,4,8-tetrahydro-1H-pyrido[1,2-a]pyrazin-6-yl)methyl)carbamate}

A solution of Int 18a (67 mg, 0.106 mmol) in dichloromethane (1.0 ml) was treated at room temperature with triethylamine (0.029 ml, 0.211 mmol) and $BOC_2O$ (0.054 ml, 0.232 mmol). The mixture was stirred at room temperature for 16 hours and then directly purified via flash column chromatography on silica gel (0 to 10% methanol/dichloromethane) to afford Int 18b. (ESI-MS) m/z 620.18, 622.16; Rt 2.13 min (LC4).

Step C—Preparation of Intermediate Compound Int 18c {tert-butyl((9-(benzyloxy)-2-(3-chloro-4-fluorobenzyl)-1,8-dioxo-7-(prop-1-en-2-yl)-2,3,4,8-tetrahydro-1H-pyrido[1,2-a]pyrazin-6-yl)methyl)carbamate}

A solution of Int 18b (60 mg, 0.097 mmol), potassium isopropenyltrifluoroborate (31.5 mg, 0.213 mmol) and $PdCl_2(dppf)$-$CH_2Cl_2$ adduct (7.89 mg, 9.66 μmol) in acetonitrile (1.0 ml) and water (0.1 ml) was treated at room temperature with diisopropylethylamine (0.051 ml, 0.290 mmol). The mixture was sub-surface sparged with nitrogen for 1 minute, capped and heated at 100° C. for 2 hours. After cooling to room temperature, the mixture was neutralized with glacial AcOH and filtered. The filtrate was purified using RP-HPLC to afford Int 18c. (ESI-MS) m/z 582.2; Rt 2.1 min (LC4).

Step D—Preparation of Compound 31 {tert-butyl ((2-(3-chloro-4-fluorobenzyl)-9-hydroxy-7-isopropyl-1,8-dioxo-2,3,4,8-tetrahydro-1H-pyrido[1,2-a]pyrazin-6-yl)methyl)carbamate}

A solution of Int 18c (50 mg, 0.086 mmol) in ethanol (2.0 ml) and 1,2-dichloroethane (1.0 ml) was treated at room temperature with platinum(IV) oxide (19.5 mg, 0.086 mmol), stirred under hydrogen (1 atm) for 4 hours, and filtered. The filtrate was concentrated. The residue was purified using RP-HPLC to afford Compound 31. (ESI-MS) m/z 494.2; Rt 1.9 min (LC4).

Step E—Preparation of Compound 32 {6-(aminomethyl)-2-(3-chloro-4-fluorobenzyl)-9-hydroxy-7-isopropyl-3,4-dihydro-1H-pyrido[1,2-a]pyrazine-1,8(2H)-dione trifluoroacetate salt}

A solution of Compound 31 (29 mg, 0.059 mmol) in trifluoroacetic acid (1.0 ml) was stirred at room temperature for 16 hours, concentrated and the residue was purified using preparative RP-HPLC to afford Compound 32. (ESI-MS) m/z 394.1; Rt 1.7 min (LC4).

Example 19

Preparation of Compound 10

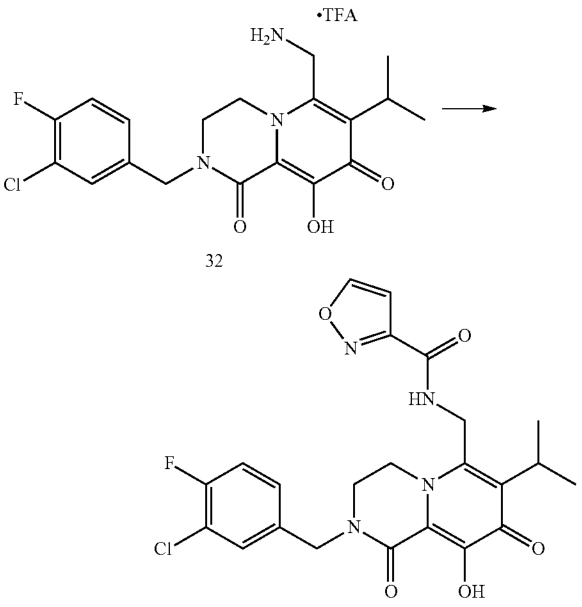

Preparation of Intermediate Compound 10 {N-((2-(3-chloro-4-fluorobenzyl)-9-hydroxy-7-isopropyl-1,8-dioxo-2,3,4,8-tetrahydro-1H-pyrido[1,2-a]pyrazin-6-yl)methyl)isoxazole-3-carboxamide}

In a 4 ml vial was placed Compound 32 (0.025 g, 0.049 mmol), isoxazole-3-carboxylic acid (8.4 mg, 0.074 mmol), HATU (0.028 g, 0.074 mmol), N,N-dimethylamide (0.50 ml) and triethylamine (0.021 ml, 0.148 mmol). The vial was capped and placed on a shaker at room temperature overnight. The mixture was then treated with aqueous 50% w/w NaOH (100 μL) and 2-propanol (200 μL), heating at 80° C. for 1 hour, cooled to room temperature and purified using RP-HPLC to afford Compound 10. (ESI-MS) m/z 489.1; Rt 1.2 min (LC4)

Example 20

Assay for Inhibition of HIV Replication

The ViKinG (Viral Kinetics GFP Reporter) assay is an in vitro kinetic assay that employs the MT4-gag-GFP reporter cell line (Wang et al., "Assessment of the susceptibility of mutant HIV-1 to antiviral agents." *J Virological Methods* 165:230-37 (2010)) to quantify the number of new cells infected in each round of replication. The purpose of the ViKinG assay is to identify agents that inhibit HIV progression. Briefly, HIV infection results in tat transactivation of the stably expressed HIV LTR promoter to drive gagGFP expression. Thus, an increase in the number of GFP-MT4 cells results following HIV infection. Compounds dose dependently inhibit the number of GFP cells.

MT4-GFP cells (250,000 cells/m1) were bulk-infected with HIV-1 (NL4-3 strain) at low multiplicity of infection (MOT) in RPMI+10% FBS for 24 hours. Cells were then washed once in RPMI+10% FBS and resuspended RPMI+10% or 50% normal human serum (NHS). Test compounds were serial-diluted in DMSO on an ECHO® liquid handling platform (Labcyte Corp., Sunnyvale, Calif.), along with a triple drug control (integrase, protease and NNRTI compounds). The infected MT4-GFP cells were added to a 384-well poly-D-lysine coated black plate with clear bottom in which the diluted test compounds were placed. The cells were seeded at 8,000 cells per well and the final DMSO concentration was 0.4%. The infected cells (Green GFP cells) were quantified at both 24 and 48 hours post incubation using Acumen® eX3 (TTP Labtech Ltd., Hertfordshire, United Kingdom). Viral reproductive ratio ($R_0$) was determined using the number of infected cells at 48 hours divided by the number of infected cells at 24 hours. Percent viral growth inhibition was calculated by $[1-(R-R_{tripledrug})/(R_{DMSO}-R_{tripledrug})]*100$. Compound potency IP or IC50 was determined by a 4-parameter dose response curve analysis.

Representative compounds of the present invention exhibit inhibition of HIV replication in this assay. For example, as shown by their ViKinG values (nm) in Table 2 below, the compounds set forth in the foregoing Examples were tested in this assay and found to exhibit inhibition of HIV-1 replication to varying degrees.

Example 21

InSTANT Assay

InSTANT is an integrase DNA strand transfer functional assay used to determine potency of InSTIs, which was carried out as described below. 8 μl of SPA buffer (27.8 mM Hepes, 27.8 mM $MgCl_2$, 111.1 μg/mL BSA, 5.56 mM βME, and 57.1 mM NaCl) containing 5 nM 3H-labeled target DNA (prepared separately) and 10 μl of assembled PVT SPA beads with WT-Integrase and boitinylated DNA (prepared separately) were added to the assay plate which contained 0.4 μl of test compound(s) or positive or negative control compound(s) per well. The assay plate was shaken for 1 minute on HT-91002 1.0 MM shaker and then was sealed and incubated for 15 minutes at 37° C. The assay reaction was quenched by adding 4 μl of 1.25 M EDTA to each well of the assay plate with mixing. After incubating the plate at room temperature for 1 hour, the quenched plate was spun at 200 g for 1 minute and read on TopCount (1 minute per well). Percent inhibition was calculated by [1−(Sample−Min)/(Max−Min)]*100. Compound potency IP or IC50 was determined by a 4-parameter dose response curve analysis.

TABLE 2

| Assay Data | | |
|---|---|---|
| Compound# | ViKinG (nM) $IC_{50}$ | Instant (nM) $IC_{50}$ |
| 1 | 347 | 58 |
| 2 | 76 | 11 |
| 3 | 241 | |
| 4 | 91 | 18 |
| 5 | 183 | |
| 6 | 492 | 21 |
| 7 | 461 | 13 |
| 8 | 507 | 28 |
| 9 | 961 | |
| 11 | 298 | |
| 12 | 1020 | |

TABLE 2-continued

| Assay Data | | |
|---|---|---|
| Compound# | ViKinG (nM) $IC_{50}$ | Instant (nM) $IC_{50}$ |
| 13 | 333 | 8 |
| 14 | 144 | 12 |
| 15 | 401 | |
| 16 | 487 | |
| 17 | >4200 | |
| 18 | 3655 | 20 |
| 19 | 82 | 10 |
| 20 | 286 | 20 |
| 21 | 155 | 2 |
| 22 | 456 | 1 |
| 23 | 273 | |
| 24 | 1123 | |
| 25 | 351 | 21 |
| 26 | 272 | |
| 27 | 672 | |
| 28 | 503 | |
| 29 | >4200 | |
| 30 | 3254 | |
| 31 | 2611 | 42 |
| 32 | 151 | 14 |
| 10 | 406 | |

What is claimed is:

1. A compound having the formula (I):

(I)

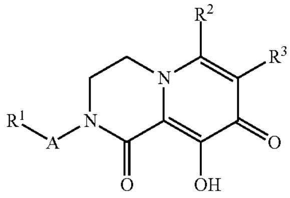

or a pharmaceutically acceptable salt thereof, wherein:

A is a bond or $C_1$-$C_3$ alkylene;

$R^1$ is $C_6$-$C_{10}$ aryl, 5- or 6-membered monocyclic heteroaryl or 9- to 11-membered bicyclic heteroaryl, wherein said $C_6$-$C_{10}$ aryl, 5- or 6-membered monocyclic heteroaryl or 9- to 11-membered bicyclic heteroaryl is optionally substituted with one or more halo, $C_1$-$C_6$ alkyl, $C_1$-$C_6$ haloalkyl, —CN, —$N(R^4)_2$, —OH, —O—($C_1$-$C_6$ alkyl), —O—($C_1$-$C_6$ haloalkyl), —OC(O)$R^7$, —C(O)$N(R^4)_2$, —NHC(O)$R^7$ or —C(O)$OR^7$;

$R^2$ is —$C(R^7)(R^8)N(R^4)_2$, or $C_1$-$C_6$ hydroxyalkyl;

$R^3$ is $C_2$-$C_6$ alkenyl, $C_1$-$C_6$ alkyl, $C_3$-$C_6$ cycloalkenyl or $C_3$-$C_7$ cycloalkyl; or $R^2$ and $R^3$, together with the carbon atoms to which they are attached, optionally form a cyclic group Y;

each occurrence of $R^4$ is independently H, $C_1$-$C_6$ alkyl, $C_3$-$C_7$ cycloalkyl, —($C_1$-$C_3$ alkylene)-O—($C_1$-$C_6$ alkyl) or —C(O)$R^{10}$;

$R^7$ is H, $C_1$-$C_6$ alkyl, $C_3$-$C_7$ cycloalkyl or phenyl;

$R^8$ is H, $C_1$-$C_6$ alkyl, $C_3$-$C_7$ cycloalkyl or phenyl; or $R^7$ and $R^8$, together with the carbon atom to which they are attached, form a carbonyl;

$R^{10}$ is $C_1$-$C_6$ alkyl, $C_6$-$C_{10}$ aryl, $C_3$-$C_7$ cycloalkyl, 5- or 6-membered monocyclic heteroaryl, 9- to 11-membered bicyclic heteroaryl, 4- to 8-membered monocyclic heterocycloalkyl, or 8- to 11-membered bicyclic heterocycloalkyl;

Y is selected from the group consisting of:

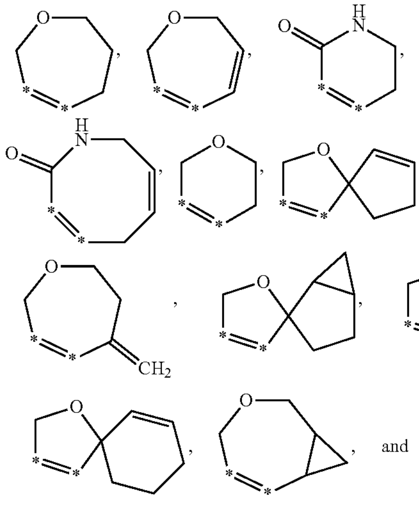

and

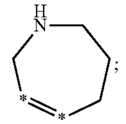

;

wherein Y is optionally substituted on one or more ring carbon atoms with one or more $C_1$-$C_6$ alkyl, $C_2$-$C_6$ alkenyl, —OH, —O—($C_1$-$C_6$ alkyl), —C(O)$OR^6$, —C(O)$N(R^9)_2$, $C_6$-$C_{10}$ aryl, 5- or 6-membered monocyclic heteroaryl or 9- to 11-membered bicyclic heteroaryl, and wherein Y is further optionally substituted on one or more ring nitrogen atoms with $C_1$-$C_6$ alkyl, —C(O)$OR^6$, —C(O)$N(R^4)_2$ or —C(O)—($C_1$-$C_3$ alkylene)-$N(R^4)_2$, wherein Y does not have the structure:

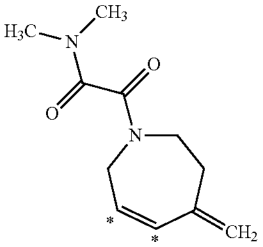

or

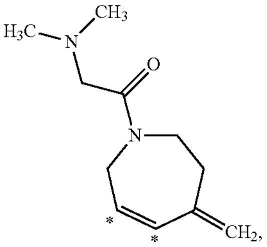

wherein the * symbols designate the point of attachment of $R^2$ and $R^3$ to the rest of the compound;

$R^6$ is H, $C_1$-$C_6$ alkyl, $C_3$-$C_7$ cycloalkyl, $C_6$-$C_{10}$ aryl, 5- or 6-membered monocyclic heteroaryl or 9- to 11-membered bicyclic heteroaryl; and each occurrence of $R^9$ is independently H, $C_1$-$C_6$ alkyl, $C_3$-$C_7$ cycloalkyl or —($C_1$-$C_3$ alkylene)-O—($C_1$-$C_6$ alkyl).

2. The compound of claim 1, having the formula (Ia):

(Ia)

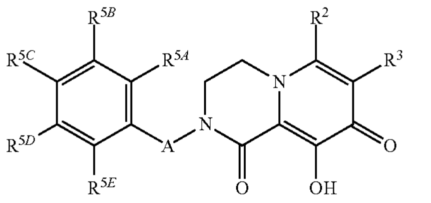

or a pharmaceutically acceptable salt thereof, wherein:

A is $C_1$-$C_3$ alkylene; and $R^{5A}$, $R^{5B}$, $R^{5C}$, $R^{5D}$, and $R^{5E}$ are each independently H, $C_1$-$C_6$ alkyl, halo, $C_1$-$C_6$ haloalkyl, —$N(R^4)_2$, —CN, $C(O)N(R^4)_2$, —O—($C_1$-$C_6$ alkyl), —$C(O)OR^7$ or —$NHC(O)R^7$.

3. The compound of claim 2, having the formula (Ib):

(Ib)

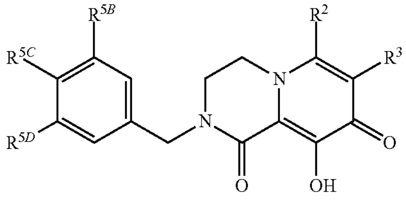

or a pharmaceutically acceptable salt thereof, wherein $R^{5B}$, $R^{5C}$, and $R^{5D}$, are each independently H, F, or Cl.

4. The compound of claim 3, wherein:

(a) $R^{5B}$ is H, $R^{5C}$ is F, and $R^{5D}$ is Cl;

(b) $R^{5B}$ is Cl, $R^{5C}$ is F, and $R^{5D}$ is H; or (c) $R^{5B}$ is H, $R^{5C}$ is F, and $R^{5D}$ is H.

5. The compound of claim 4, wherein:

$R^2$ is —$C(O)NHCH_2CH_2OCH_3$, —$CH_2OH$ or —$CH_2NH_2$; and $R^3$ is cyclopentenyl, cyclohexenyl, cyclopentyl, isopropyl, —$C(CH_3)$=$CH_2$, —$CH_3$ or —$CH_2CH_3$.

6. The compound of claim 4, wherein $R^2$ and $R^3$, together with the carbon atoms to which they are attached, form a cyclic group Y.

7. The compound of claim 6, wherein $R^2$ and $R^3$, together with the carbon atoms to which they are attached, form a cyclic group Y having the structure:

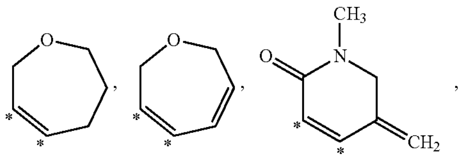

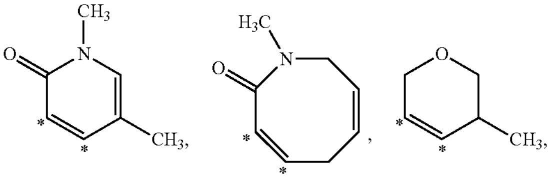

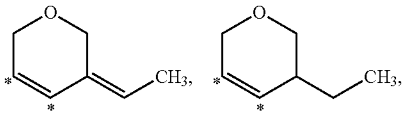

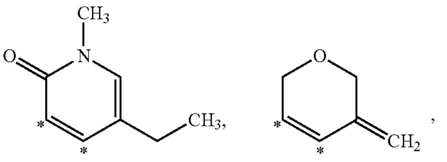

-continued

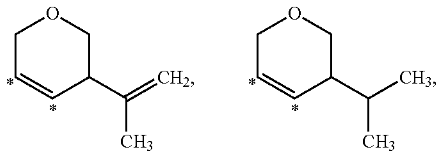

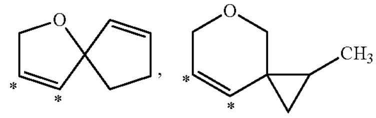

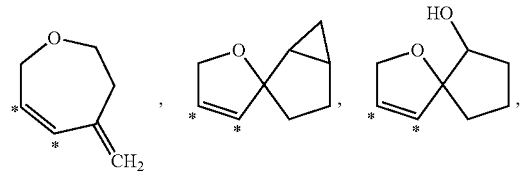

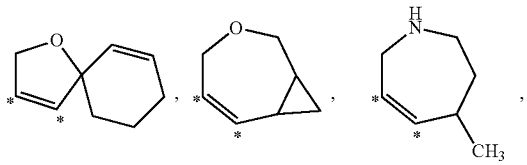

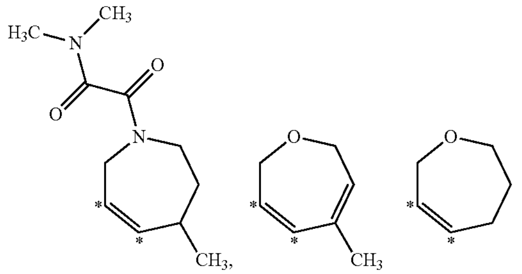

or

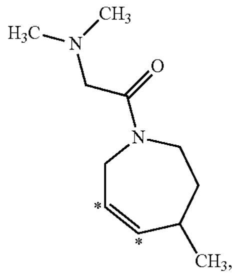

wherein the * symbols designate the point of attachment of $R^2$ and $R^3$ to the rest of the compound.

8. The compound of claim 2, wherein up to two of $R^{5A}$, $R^{5B}$, $R^{5C}$, $R^{5D}$, and $R^{5E}$ are independently H or halo.

9. The compound of claim 1, having the structure:

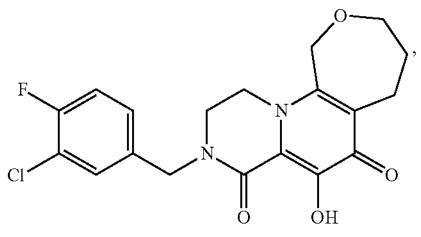

-continued
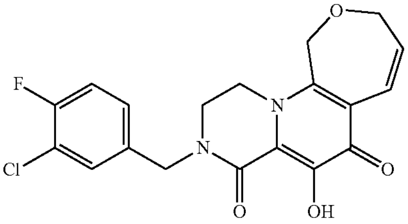,
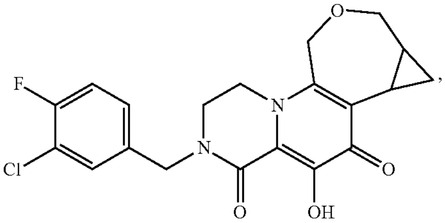,
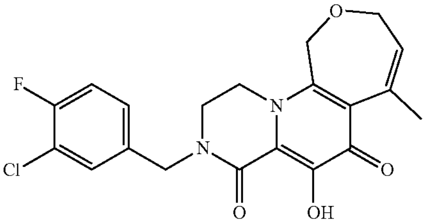,
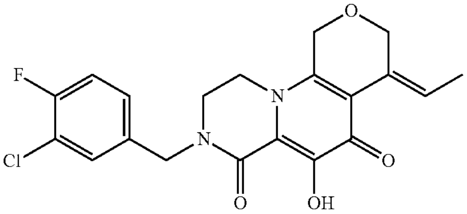,
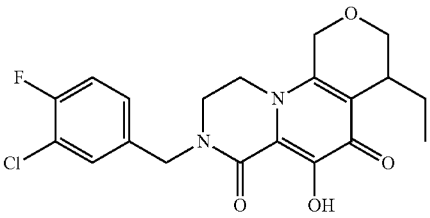,
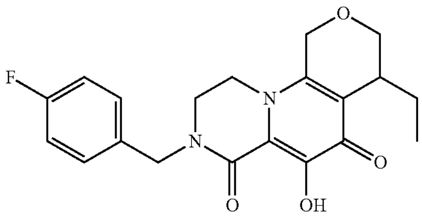,
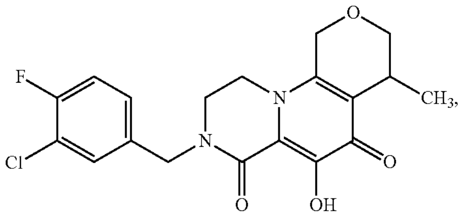
-continued
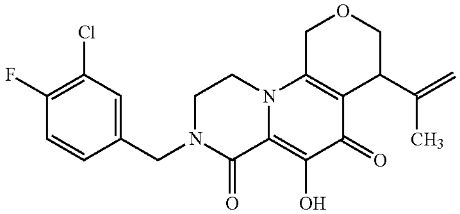,
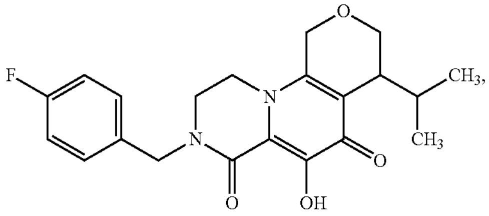
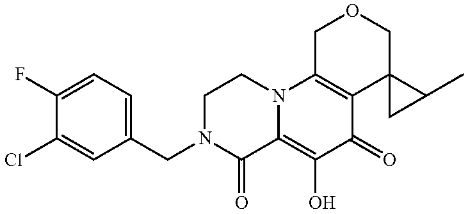,
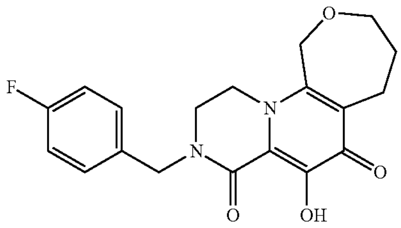,
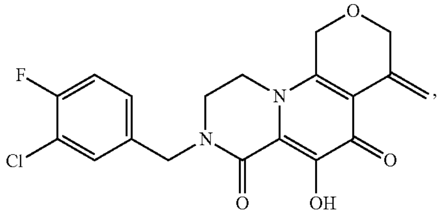,
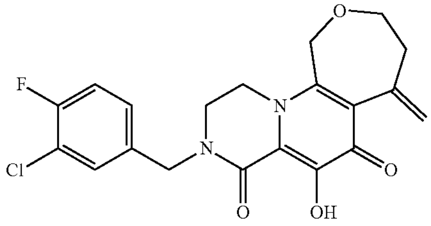,
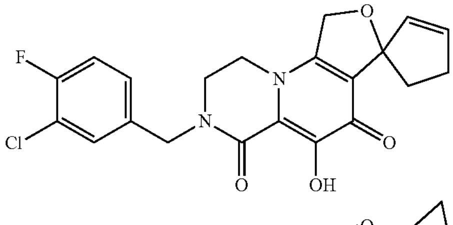,
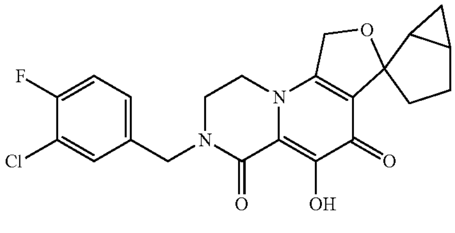, -continued
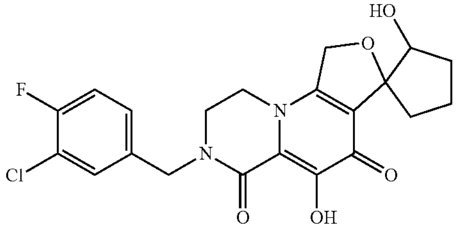
,
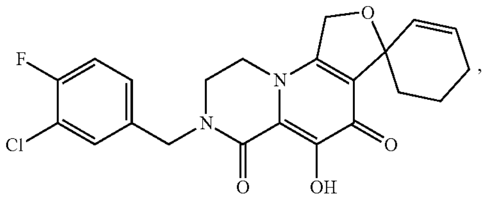
,
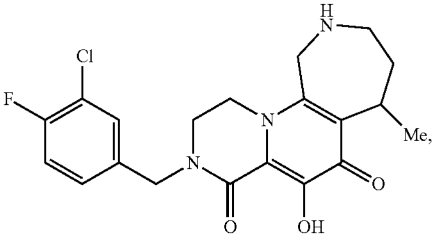
,
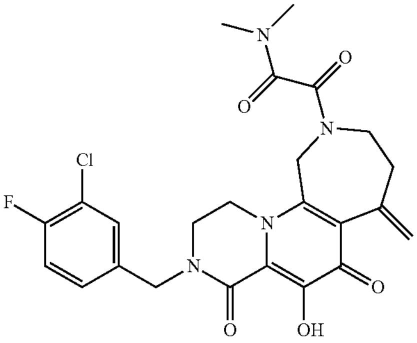
,
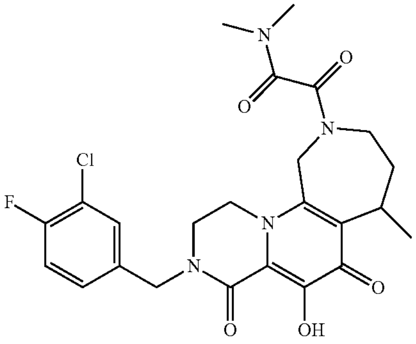
,
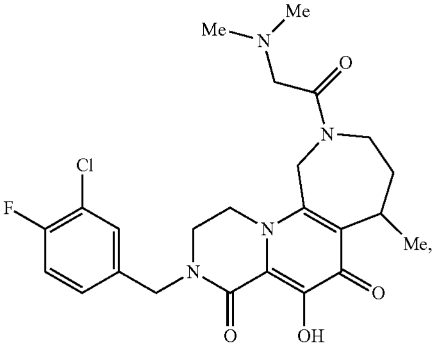
,
-continued
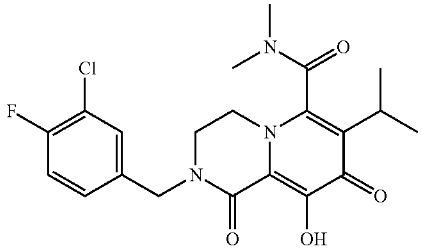
,
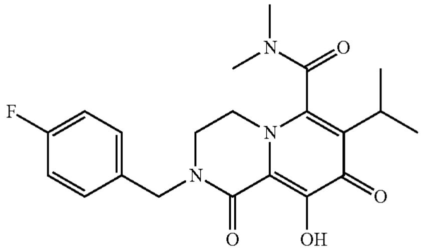
,
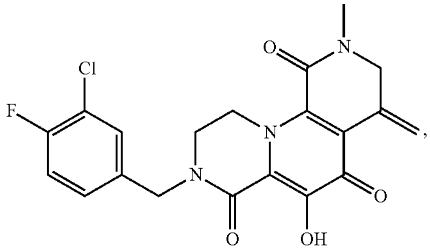
,
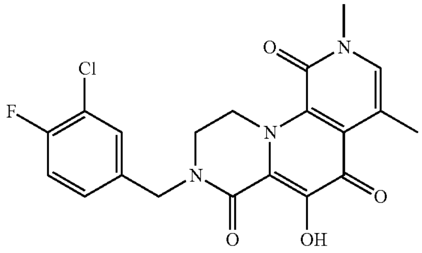
,
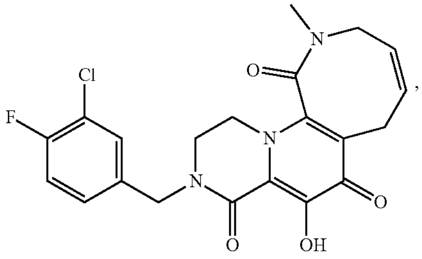
,
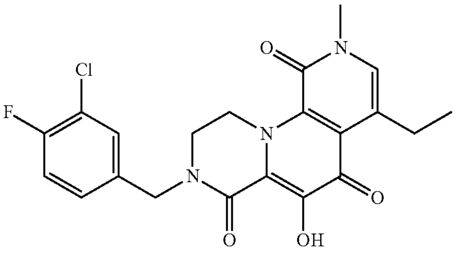
, -continued

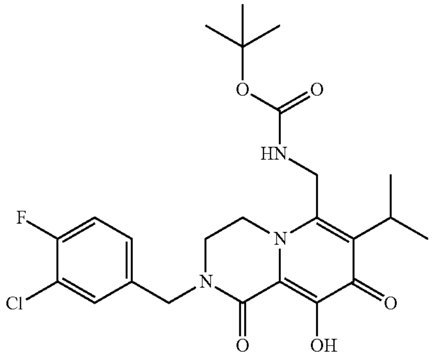

,

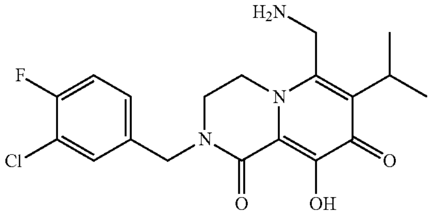

, or

-continued

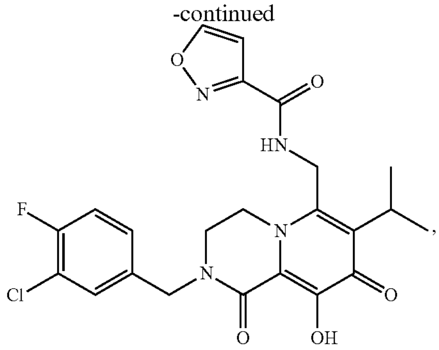

, or a pharmaceutically acceptable salt thereof.

10. A pharmaceutical composition comprising an effective amount of a compound according to claim 1, or a pharmaceutically acceptable salt thereof, and a pharmaceutically acceptable carrier.

11. The pharmaceutical composition of claim 10, further comprising one or more additional therapeutic agents selected from the group consisting of raltegravir, lamivudine, abacavir, ritonavir, dolutegravir, arunavir, atazanavir, emtricitabine, tenofovir, elvitegravir, rilpivirine and lopinavir.

12. A method for the inhibition of human immunodeficiency virus integrase in a subject in need thereof, which comprises administering to the subject an effective amount of the compound according to claim 1, or a pharmaceutically acceptable salt thereof.

* * * * *